US005654333A

United States Patent [19]
Samid

[11] Patent Number: 5,654,333
[45] Date of Patent: Aug. 5, 1997

[54] METHODS FOR PREVENTION OF CANCER USING PHENYLACETIC ACIDS AND DERIVATIVES THEREOF

[75] Inventor: Dvorit Samid, Rockville, Md.

[73] Assignee: The United States of America as represented by the Department of Health and Human Services, Washington, D.C.

[21] Appl. No.: 465,941

[22] Filed: Jun. 6, 1995

Related U.S. Application Data

[60] Division of Ser. No. 135,661, Oct. 12, 1993, which is a continuation-in-part of Ser. No. 779,744, Oct. 21, 1991.

[51] Int. Cl.$^6$ .................. A01N 37/12; A01N 37/44; A61K 31/24
[52] U.S. Cl. .................. 514/538; 514/563; 514/567
[58] Field of Search .................. 514/538, 563, 514/567

[56] References Cited

U.S. PATENT DOCUMENTS

| | | | |
|---|---|---|---|
| 3,973,022 | 8/1976 | Goschke | 514/311 |
| 3,976,673 | 8/1976 | Pifferi | 514/568 |
| 3,998,966 | 12/1976 | Fried et al. | 514/510 |
| 4,028,404 | 6/1977 | Bays et al. | 514/570 |
| 4,282,214 | 8/1981 | Flora et al. | 514/108 |
| 4,457,942 | 7/1984 | Brusilow | 424/317 |
| 4,470,970 | 9/1984 | Burzynski | 424/177 |
| 4,702,506 | 10/1987 | Munakata et al. | 514/538 |
| 5,244,922 | 9/1993 | Burzynski | 514/561 |

FOREIGN PATENT DOCUMENTS

| | | |
|---|---|---|
| 1511645 | 5/1978 | United Kingdom . |

OTHER PUBLICATIONS

Timothy J. Ley, et al., "5–Azacytidine Selectively Increases γ–globin Synthesis in a Patient with β$^+$ Thalassemia", New England Journal of Medicine, vol. 307:1469–1475 (Dec. 9, 1982).
Michael B. Sporn, et al., "Chemoprevention of Cancer with Retinoids", Federation Proceedings, vol. 38:2528–2534 (Oct. 1979).
Richard L. Momparler, et al., "Clinical Trial on 5–AZA–2'–Deoxycytidine in Patients with Acute Leukemia", Pharmac. Ther., vol. 30:277–286 (1985).
Gary J. Kelloff, et al., "Chemoprevention Clinical Trials", Mutation Research, vol. 267:291–295 (1992).
I. Bernard Weinstein, "Cancer Prevention: Recent Progress and Future Opportunities", Cancer Research, vol. 51:5080s–5085s (1991).
Olli Simell, et al, "Waste Nitrogen Excretion Via Amino Acid Acylation: Benzoate and Phenylacetate in Lysinuric Protein Intolerance", Pediatr. Res., vol. 20:1117–1121 (1986).
Neish, et al., "Phenylacetic Acid as a Potential Therapeutic Agent for the Treatment of Human Cancer", Experimentia, vol. 27:860–861 (1971).

J.A. Stamatoyannopoulos, et al., "Therapeutic Approaches to Hemoglobin Switching in Treatment of Hemoglobinopathies", Annu. Rev. Med., vol. 43:497–521 (1992).
Dvorit Samid, et al., "Selective Growth Arrest and Phenotypic Reversion of Prostate Cancer Cells In Vitro by Non-Toxic Pharmacological Concentrations of Phenylacetate", The Journal of Clinical Investigation, vol. 91:2288–2295 (1993).
Dvorit Samid, et al., "Induction of Erythroid Differentiation and Fetal Hemoglobin Production in Human Leukemic Cells Treated with Phenylacetate", Journal of the Amiercan Society of Hematology, vol. 80:1576–1581 (1992).
Dvorit Samid, et al., "Phenylacetate: A Novel Nontoxic Inducer of Tumor Cell Differentiation", Cancer Research, vol. 52:1988–1992 (1992).
George J. Dover, et al., "Increased Fetal Hemoglobin in Patients Receiving Sodium 4–Phenylbutyrate", The New England Journal of Medicine, vol. 327:569–570 (1992).
Burzynski, S.R. et al., Preclinical Studies on antineoplaston AS2–1 and Antineoplaston AS2–5, Drugs Exptl. Clin. Res., Supplemental 1, XII:11–16 (1986).
Leary, Cancer Drug Also Helps in Treating Sickle Cell Anemia, Researchers Say, Atlanta Journal–Constitution, Thursday, Aug. 20, 1992.
Smigel, K., "Non–toxic drug being tested to treat cancer and anemias (news)", J. Natl. Cancer Inst., 84(18):1398 (Sep. 16, 1992).
Ross, Philip D. and Subramanian, S., Inhibition of sickle cell hemoglobin gelation by some aromatic compounds, Briochem. Biophys. Res. Commun., 77:1217–1223 (1977).
Jones, G.L., Anti sickling effects of Betw Di Ethylaminoethyldiphenylpropyl acetate SFK–525–A, Pharmacologist, 20(3):204 (1978).
Erhum, Wilson O., Acetonyl esters of hydroxybenzoic acids as potential antisickling agents, Niger. J. Pharm., 12:285–287 (1981).
Abemayor, E. et al., Effects of retinoic acid on the in vivo growth of human neuroblastoma cells,Cancer Lett. (Netherlands), 70(1–2):15–24 (Jun. 15, 1993).
Cinatl, J. et al., In vitro differentiation of human neuroblastoma cells induced by sodium phenylacetate, Cancer Lett. (Netherlands), 70(1–2):15–24 (Jun. 15, 1993).
Gorski, G.K. et al., Synergistic inhibition of human rhabdomyosarcoma cells by sodium phenylacetate and tretinoin, In Vitro Cell. Dev. Biol., 29A:189–191 (Mar. 1993).

Primary Examiner—Nathan M. Nutter
Attorney, Agent, or Firm—Needle & Rosenberg, P.C.

[57] ABSTRACT

Compositions and methods of treating anemia, cancer, AIDS, or severe β-chain hemoglobinopathies by administering a therapeutically effective amount of phenylacetate or pharmaceutically acceptable derivatives thereof or derivatives thereof alone or in combination or in conjunction with other therapeutic agents. Pharmacologically-acceptable salts alone or in combinations and methods of preventing AIDS and malignant conditions, and inducing cell differentiation are also aspects of this invention.

30 Claims, 25 Drawing Sheets

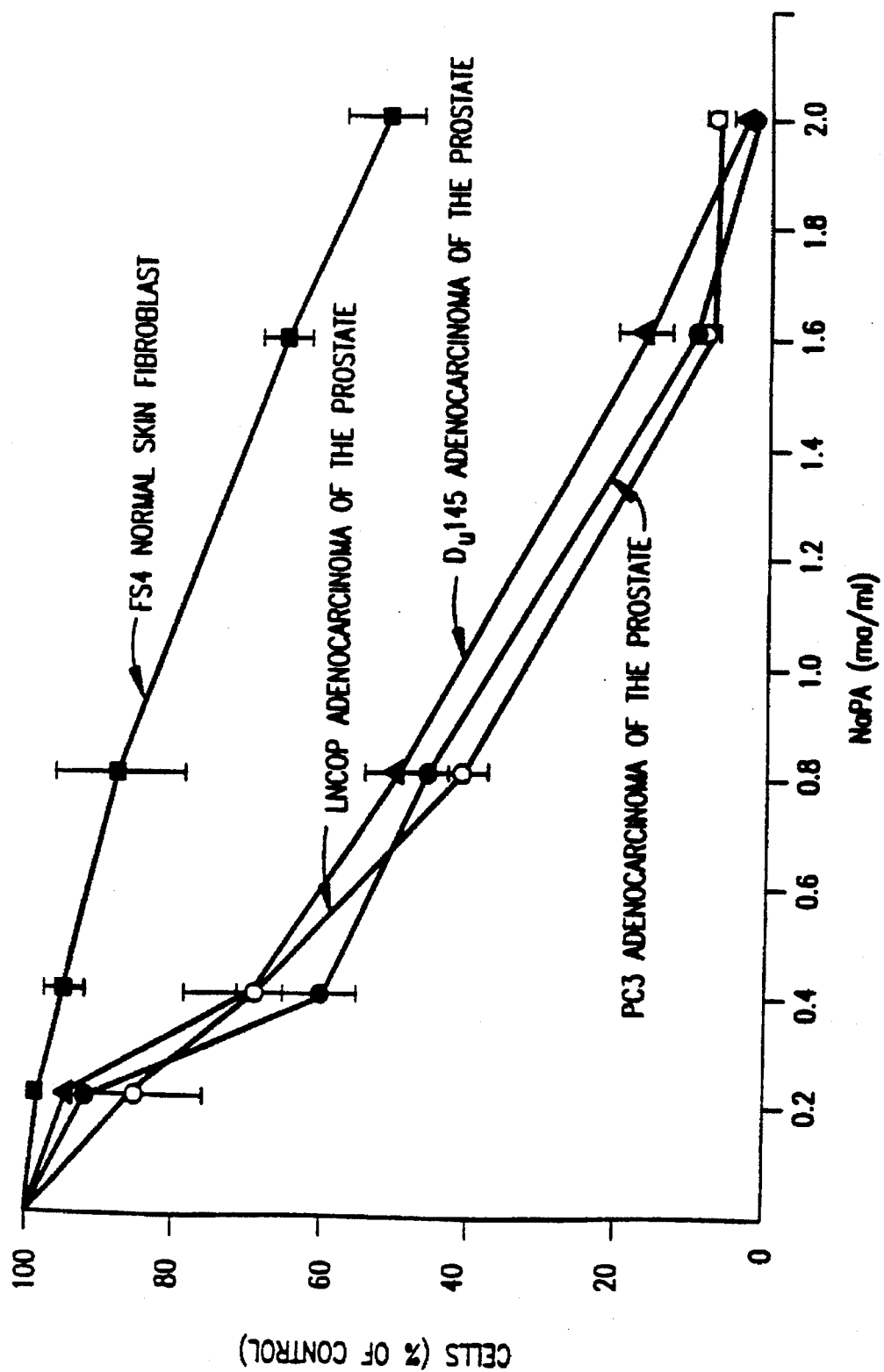

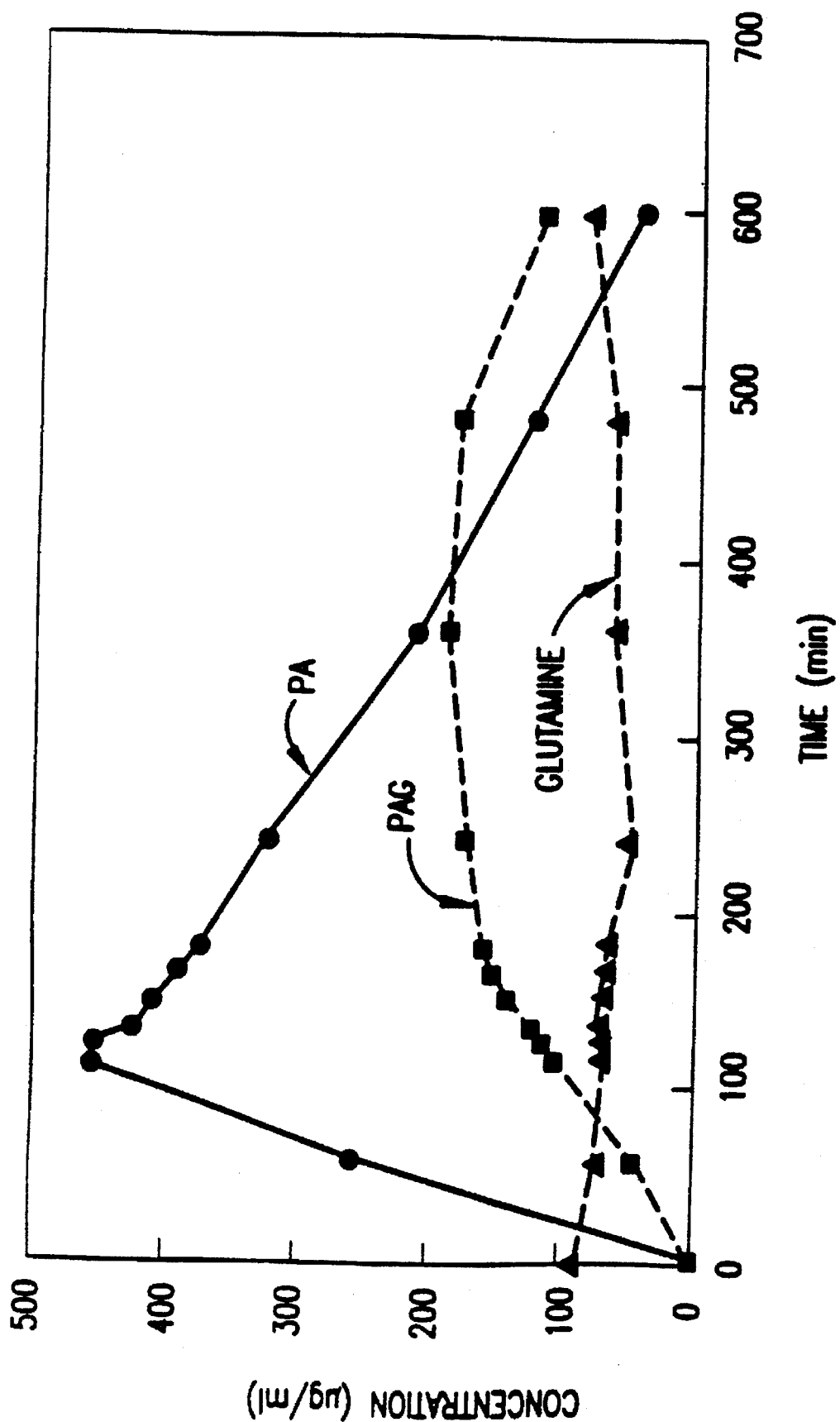

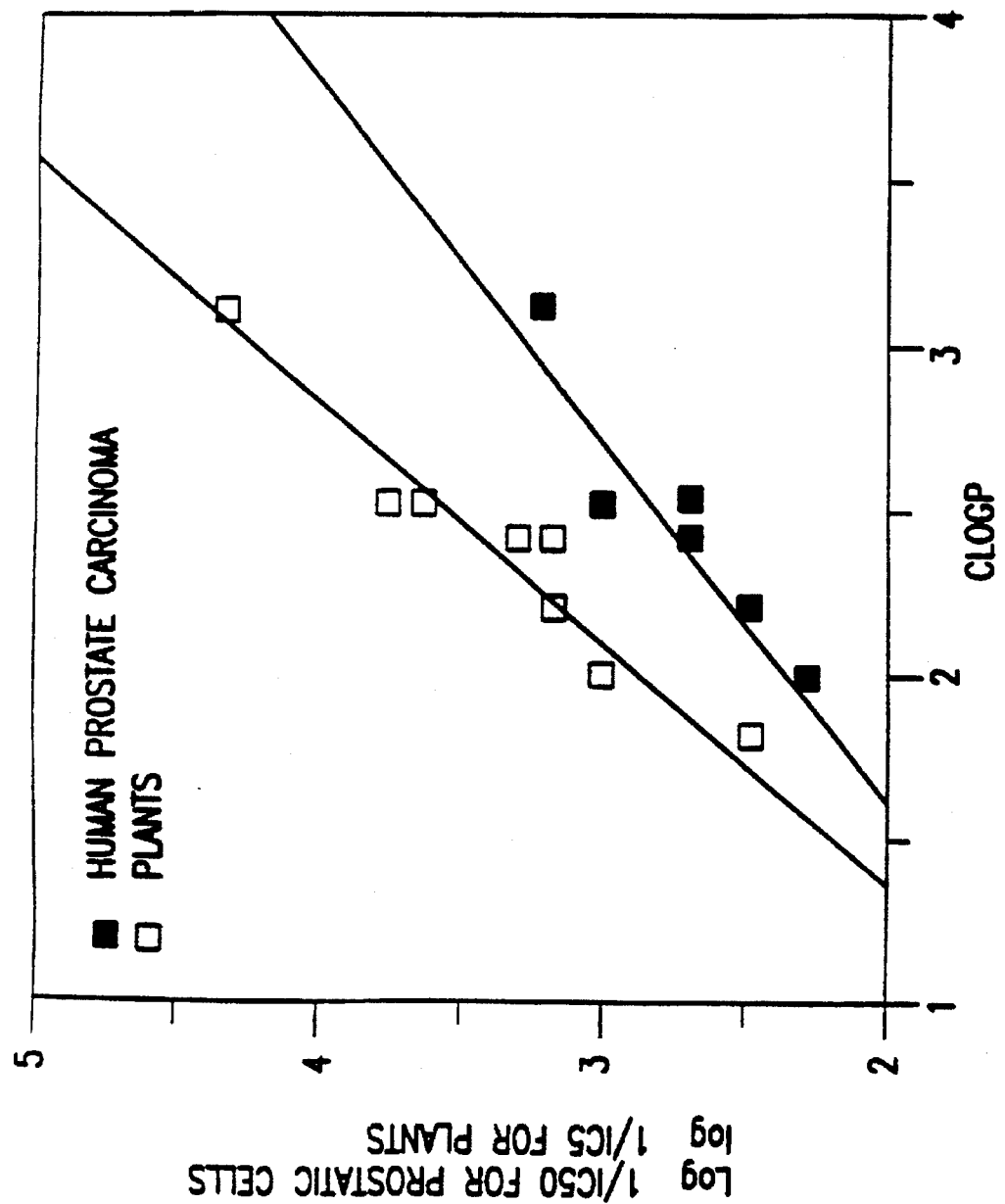

METHODS FOR PREVENTION OF CANCER USING PHENYLACETIC ACIDS AND DERIVATIVES THEREOF

This application is a division of applicant's Ser. No. 08/135,661, filed on Oct. 12, 1993, which, in turn, is a Continuation-In-Part of applicant's copending U.S. Ser. No. 07/779,744, filed Oct. 21, 1991, the contents of which are hereby incorporated by reference.

FIELD OF THE INVENTION

This invention relates to methods of using phenylacetic acid and its pharmaceutically acceptable derivatives to treat and prevent pathologies and to modulate cellular activities. In particular, this invention relates to A) phenylacetate and its derivatives in cancer prevention and maintenance therapy, B) phenylacetate and its derivatives in the treatment and prevention of AIDS, C) induction of fetal hemoglobin synthesis in β-chain hemoglobinopathy by phenylacetate and its derivatives, D) use of phenylacetic acid and its derivatives in wound healing, E) use of phenylacetic acid and its derivatives in treatment of diseases associated with interleukin-6, F) use of phenylacetic acid and its derivatives in the treatment of AIDS-associated CNS dysfunction, G) use of phenylacetic acid and its derivatives to enhance immunosurveillance, H) methods of monitoring the dosage level of phenylacetic acid and its derivatives in a patient and/or the patient response to these drugs, I) the activation of the PPAR by phenylacetic acid and its derivatives, J) use of phenylacetic acid and its derivatives in treatment of cancers having a multiple-drug resistant phenotype, and K) phenylacetic acid and its derivatives, correlation between potency and lipophilicity.

BACKGROUND OF THE INVENTION

Phenylacetic acid (PAA) is a protein decomposition product found throughout the phylogenetic spectrum, ranging from bacteria to man. Highly conserved in evolution, PAA may play a fundamental role in growth control and differentiation. In plants, PAA serves as a growth hormone (auxin) promoting cell proliferation and enlargement at low doses ($10^{-5}$–$10^{-7}$M), while inhibiting growth at higher concentrations. The effect on animal and human cells is less well characterized. In humans, PAA is known to conjugate glutamine with subsequent renal excretion of phenylacetylglutamine (PAG). The latter, leading to waste nitrogen excretion, has been the basis for using PAA or preferably its salt sodium phenylacetate (NaPA, also referenced herein as that active anionic meoity, phenylacetate or "PA") in the treatment of hyperammonemia associated with inborn errors of ureagenesis. Clinical experience indicates that acute or long-term treatment with high NaPA doses is well tolerated, essentially free of adverse effects, and effective in removing excess glutamine. [Brusilow, S. W., Horwich, A. L. Urea cycle enzymes. Metabolic Basis of Inherited Diseases, Vol. 6:629–633 (1989)]. These characteristics should be of value in treatments of cancer and prevention of cancer, treatments which inhibit virus replication and treatments of severe beta-chain hemoglobinopathies.

Glutamine is the major nitrogen source for nucleic acid and protein synthesis, and a substrate for energy in rapidly dividing normal and tumor cells. Compared with normal tissues, most tumors, due to decreased synthesis of glutamine along with accelerated utilization and catabolism, operate at limiting levels of glutamine availability, and consequently are sensitive to further glutamine depletion. Considering the imbalance in glutamine metabolism in tumor cells and the ability of PAA to remove glutamine, PAA has been proposed as a potential antitumor agent; however, no data has previously been provided to substantiate this proposal. [Neish, W. J. P. "Phenylacetic Acid as a Potential Therapeutic Agent for the Treatment of Human Cancer", *Experentia*, Vol. 27, pp. 860–861 (1971)].

Despite these efforts to fight cancer, many malignant diseases that are of interest in this application continue to present major challenges to clinical oncology. Prostate cancer, for example, is the second most common cause of cancer deaths in men. Current treatment protocols rely primarily on hormonal manipulations. However, in spite of initial high response rates, patients often develop hormone-refractory tumors, leading to rapid disease progression with poor prognosis. Overall, the results of cytotoxic chemotherapy have been disappointing, indicating a long felt need for new approaches to treatment of advanced prostatic cancer. Other diseases resulting from abnormal cell replication, for example metastatic melanomas, brain tumors of glial origin (e.g., astrocytomas), and lung adenocarcinoma, are also highly aggressive malignancies with poor prognosis. The incidence of melanoma and lung adenocarcinoma has been increasing significantly in recent years. Surgical treatments of brain tumors often fail to remove all tumor tissues, resulting in recurrences. Systemic chemotherapy is hindered by blood barriers. Therefore, there is an urgent need for new approaches to the treatment of human malignancies including advanced prostatic cancer, melanoma, brain tumors.

The development of the methods and pharmaceuticals of the present invention was guided by the hypothesis that metabolic traits that distinguish tumors from normal cells could potentially serve as targets for therapeutic intervention. For instance, tumor cells show unique requirements for specific amino acids such as glutamine. Thus, glutamine may be a desired choice because of its major contribution to energy metabolism and to synthesis of purines, pyrimidines, and proteins. Along this line, promising antineoplastic activities have been demonstrated with glutamine-depleting enzymes such as glutaminase, and various glutamine antimetabolites. Unfortunately, the clinical usefulness of these drugs has been limited by unacceptable toxicities. Consequently, the present invention focuses on PAA, a plasma component known to conjugate glutamine in vivo, and the pharmaceutically acceptable derivatives of PAA.

In addition to its ability to bind gluatamine to form glutamine phenylacetate, PAA can induce tumor cells to undergo differentiation. (See examples 1–5, 7–9, 11–13, and 16 herein). Differentiation therapy is a known, desirable approach for cancer intervention. The underlying hypothesis is that neoplastic transformation results from defects in cellular differentiation. Inducing tumor cells to differentiate would prevent tumor progression and bring about reversal of malignancy. Several differentiation agents are known, but their clinical applications have been hindered by unacceptable toxicities and/or deleterious side effects.

Accordingly, the present invention provides methods and compositions for treating various pathologies with PAA and its pharmaceutically acceptable salts, derivatives, and analogs.

BRIEF SUMMARY OF THE INVENTION

The invention provides a method of treating various pathologies in a subject. The invention also provides for the modulation of various cellular activities in a subject. The pathologies and cellular activities are treated and modulated utilizing a compound having the formula:

$$R_1-\underset{\underset{R_0}{|}}{\overset{\overset{R_2}{|}}{C}}-\left[\underset{\underset{R_4}{|}}{\overset{\overset{R_3}{|}}{C}}\right]_n-\overset{\overset{O}{\|}}{C}-OH;$$

wherein $R_0$=aryl, phenoxy, substituted aryl or substituted phenoxy;

$R_1$ and $R_2$=H, lower alkoxy, lower straight and branched chain alkyl or halogen;

$R_3$ and $R_4$=H, lower alkoxy, lower straight and branched chain alkyl or halogen; and n=an integer from 0 to 2.

Specifically, the invention provides a method of treating or preventing various neoplastic conditions. Relatedly, a method of inducing differentiation of a cell is provided. The invention also provides a method of inducing the production of fetal hemoglobin and treating pathologies associated with abnormal hemoglobin activity or production.

The invention also provides a method of treating or preventing a viral infection in a subject. Relatedly, the invention provides a method of treating an AIDS-associated dysfunction of the central nervous system in a subject.

Also provided is a method of modulating the production of IL-6 or TGFα and TGF-β2 both in vitro and in vivo. Typically, IL-6 and TGF-β2 are inhibited while TGFα is induced.

The invention also provides a method of enhancing immunosurveillance and promoting wound healing in a subject.

Also provided is a method of monitoring the bioavailability of a compound for treatment of a pathology not associated with hemoglobin. The method comprises administering to a subject the compound and measuring the level of fetal hemoglobin TGF-β2, IL-6 or TGFα.

Finally, a method of treating a neoplastc condition in cells resistant to radiation and chemotherapy is provided. Specifically, multiple drug resistant cells are particularly sensitive to the compounds of this invention.

BRIEF DESCRIPTION OF THE DRAWINGS

FIG. 6 shows key steps of the MVA pathway discussed in text.

FIG. 11 shows the effect of NaPA on cell proliferation. PC3; DU145; LNCaP; and FS4 cultures were treated with NaPA or PAG for four days.

FIG. 13 shows serum concentrations of PA ( ) and PAG ( ) and plasma concentrations of glutamine ( ) following a 150 mg/kg i.v. bolus of PA over 2 hours.

FIG. 14 shows declining phenylacetate concentrations over time during CIVI (250 mg/kg/day) in one patient, suggestive of clearance induction.

FIG. 16 shows a simulation of a q 12 hour PA regimen (200 mg/kg/dose, 1 hour infusion) in a pharmacokinetically average patient. For simplicity, induction of clearance was not factored in.

FIG. 26 shows the relationship between lipophilicity and the cytostasis induced by phenylacetate derivatives in prostate carcinoma cells and in plants. The log 1/IC$_{50}$ values for prostatic cells (calculated from data presented in Table 21), were compared with the 1/IC$_5$ for rapidly developing plant tissues. Tested compounds, listed in an increasing order of their CLOGPs, included 4-hydroxy-PA, PA, 4-fluoro-PA, 3-methyl-PA, 4-methyl-PA, 4-chloro-PA, 3-chloro-PA, and 4-iodo-PA.

DETAILED DESCRIPTION OF THE INVENTION

Figure 1:
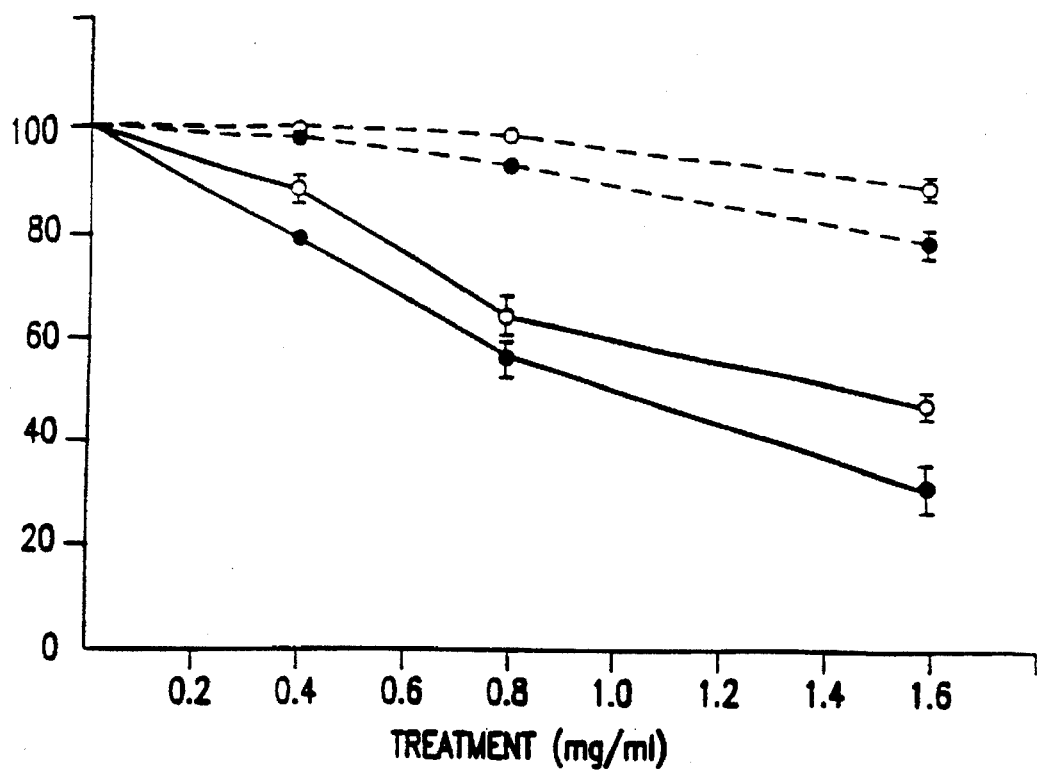
FIG. 1 shows the inhibition of HL-60 leukemia and premalignant 10T1/2 cell proliferation by NaPA.

As used herein, the term "phenylacetic acid derivative" (or "phenylacetic acid analog") refers to a compound of the formula:

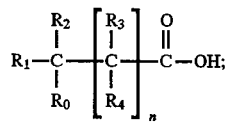

wherein

R$_0$ is aryl (e.g., phenyl, napthyl), phenoxy, substituted aryl (e.g., one or more halogen [e.g., F, Cl, Br, I], lower alkyl [e.g., methyl, ethyl, propyl, butyl] or hydroxy substituents) or substituted phenoxy (e.g., one or more halogen [e.g., F, Cl, Br, I], lower alkyl [e.g., methyl, ethyl, propyl, butyl] or hydroxy substituents);

R$_1$ and R$_2$ are each H, lower alkoxy (e.g., methoxy, ethoxy), lower straight and branched chain alkyl (e.g., methyl, ethyl, propyl, butyl) or halogen (e.g., F, Cl, Br, I);

R$_3$ and R$_4$ are each H, lower straight and branched chain alkyl (e.g., methyl, ethyl, propyl, butyl), lower alkoxy (e.g., methoxy, ethoxy) or halogen (e.g., F, Cl, Br, I); and n is an integer from 0 to 2;

salts thereof (e.g., Na⁺, K⁺ or other pharmaceutically acceptable salts); stereoisomers thereof; and mixtures thereof.

When n is equal to 2, each of the two R$_3$ substituents and each of the two R$_4$ substituents can vary independently within the above phenylacetic acid derivative definition. It is intended that this definition includes phenylacetic acid (PAA) and phenylbutyric acid (PBA). Mixtures according to this definition are intended to include mixtures of carboxylic acid salts, for instance, a mixture of sodium phenylacetate and potassium phenylacetate. Because the carboxylic portion of these compounds is the primarily active portion, references herein to a carboxylate, such as phenylacetate (PA) or phenylbutyrate (PB), are intended to refer also to an appropriate counter cation, such as Na⁺, K⁺ or another pharmaceutically acceptable cation such as an organic cation (e.g., arginine). Thus, as used herein, a PA or PB derivative or analog refers to the phenylacetic acid derivatives of this definition. Some of these derivatives can be interconverted when present in a biological system. For instance, PA can be enzymatically converted to PB within an animal and, similarly, PB can be converted to PA.

Thus, phenylacetic acid derivatives include, without limitation, phenylacetic acid, phenylpropionic acid, phenylbutyric acid, 1-naphthylacetic acid, phenoxyacetic acid, phenoxypropionic acid, phenoxybutyric acid, 4-chlorophenylacetic acid, 4-chlorophenylbutyric acid, 4-iodophenylacetic acid, 4-iodophenylbutyric acid, α-methylphenylacetic acid, α-methoxyphenylacetic acid, α-ethylphenylacetic acid, α-hydroxyphenylacetic acid, 4-fluorophenylacetic acid, 4-fluorophenylbutyric acid, 2-methylphenylacetic acid, 3-methylphenylacetic acid, 4-methylphenylacetic acid, 3-chlorophenylacetic acid, 3-chlorophenylbutyric acid, 2-chlorophenylacetic acid, 2-chlorophenylbutyric acid and 2,6-dichlorophenylacetic acid, and the sodium salts of the these compounds.

The compounds of the present invention can be administered intravenously, enterally, parenterally, intramuscularly, intranasally, subcutaneously, topically or orally. The dosage amounts are based on the effective inhibitory concentrations observed in vitro and in vivo in antitumorigenicity studies. The varied and efficacious utility of the compounds of the present invention is further illustrated by the findings that they may also be administered concomitantly or in combination with other antitumor agents (such as hydroxyurea, 5-azacytidine, 5-aza-2'-deoxycytidine, and suramin); retinoids; hormones; biological response modifiers (such as interferon and hematopoietic growth factors); and conventional chemo- and radiation therapy or various combinations thereof.

The present invention also provides methods of inducing tumor cell differentiation in a host comprising administering to the host a therapeutically effective amount of PAA or a pharmaceutically acceptable derivative thereof.

The present invention also provides methods of preventing the formation of malignancies by administering to a host a prophylactically effective amount of PAA or a pharmaceutically acceptable derivative thereof.

The present invention also provides methods of treating malignant conditions, such as prostatic cancer, melanoma, adult and pediatric tumors, e.g., brain tumors of glial origin, astrocytoma, Kaposi's sarcoma, lung adenocarcinoma and leukemias, as well as hyperplastic lesions, e.g., benign hyperplastic prostate and papillomas by administering a therapeutically effective amount of PAA or a pharmaceutically acceptable derivative thereof.

In addition, the present invention provides methods of treating conditions such as neuroblastoma, promyelocytic leukemia, myelodisplasia, glioma, prostate cancer, breast cancer, melanoma, and non-small cell lung cancer.

It is understood that the methods and compositions of this invention can be used to treat animal subjects, including human subjects.

According to the present invention, phenylacetic acid derivatives, and in particular NaPA and NaPB, have been found to be excellent inhibitors of the growth of specific tumor cells, affecting the proliferation of the malignant cells while sparing normal tissues. Also, according to the present invention, NaPA and its analogs have been found to induce tumor cell differentiation, thus offering a very desirable approach to cancer prevention and therapy. Additionally, NaPA and its analogs have been found to be of value for the treatment of viral indications such as AIDS. NaPA is also implicated in the treatment of severe beta-chain hemoglobinopathies. The exact mechanisms by which the compounds used in the methods of this invention exert their effects are uncertain. One potential mechanism may involve depletion of plasma glutamine. Based on the data reported herein, it is believed that glutamine depletion alone cannot explain the molecular and phenotypic changes observed in vitro following exposure to NaPA. It will be understood, however, that the present invention is not to be limited by any theoretical basis for the observed results.

EXAMPLES

The herein offered examples, including experiments, provide methods for illustrating, without any implied limitation, the practice of this invention focusing on phenylacetic acid and its derivatives directed to A. Cancer therapy and prevention; B. Treatment and prevention of AIDS; C. Induction of fetal hemoglobin synthesis in β-chain hemoglobinopathies; D. Use of phenylacetic acid and its derivatives in wound healing; E. Use of phenylacetic acid and its derivatives in treatment of diseases associated with interleukin-6; F. Use of phenylacetic acid and its derivatives in the treatment of AIDS-associated CNS dysfunction; G. Use of phenylacetic acid and its derivatives to enhance immunosurveillance; H. Method of monitoring the dosage level of phenylacetic acid and its derivatives in a patient and/or the patient's response to these drugs; I. The activation of the PPAR by phenylacetic acid and its derivatives; J. Use of phenylacetic acid and its derivatives in treatment of cancers having a multiple-drug resistant phenotype; and K. phenylacetic acid and its derivatives, dorrelation between potency and lipophilicity.

Section A: Phenylacetate in Cancer Prevention and Maintenance Therapy

Recent advances in molecular techniques enable the detection of genetic disorders associated with a predisposition to cancer. Consequently, it is now possible to identify high-risk individuals as well as patients in a state of remission but afflicted with a residual disease. Despite such remarkable capabilities, there is still no acceptable preventive treatment. Chemopreventive drugs are also needed for adjuvant therapy, to minimize the carcinogenic effects of the prevailing anticancer agents and yet maintain tumor responses.

To qualify for use in chemoprevention, a potential drug should have antitumor activities, be non-toxic and well tolerated by humans, easy to administer (e.g., orally or intravenously), and inexpensive. We suggest that NaPA possesses all of the above characteristics.

1. Prevention of Neoplastic Transformation—Oncogene Transfer Studies

NIH 3T3 cells carrying activated Ejras oncogene (originally isolated from human bladder carcinoma) were used as a model to study the potential benefit of NaPA treatment to high risk individuals, in whom predisposition is associated with oncogene activation. Cell treatment with NaPA was initiated 24–48 hours after oncogene transfer. Results, scored 14–21 days later, show dose-dependent reduction in the formation of ras-transformed foci in cultures treated with NaPA. Molecular analyses indicated that the drug did not interfere with oncogene uptake and transcription, but rather prevented the process of neoplastic transformation. The effect was reversible upon cessation of treatment. In treated humans, however, the fate of the premalignant cells may be substantially different due to involvement of humoral and cellular immunity (see discussion below).

2. Prevention of tumor progression by genotoxic chemotherapy

Current approaches to combat cancer rely primarily on the use of chemicals and radiation, which are themselves carcinogenic and may promote recurrences and the development of metastatic disease. One example is the chemotherapeutic drug 5-aza-2'-deoxycytidine (5AzadC). While this drug shows promise in treatment of some leukemias and severe inborn anemias, the clinical applications have been hindered by concerns regarding toxicity and carcinogenic effects. However, for the first time the data indicate that NaPA can prevent tumor progression induced by treatment with 5AzadC.

The experimental model involved nonmalignant 4C8a10 cells (revertants of Ha-ras-transformed NIH 3T3 fibroblasts). Transient treatment of the premalignant cells with 5AzadC resulted in malignant conversion evident within 2 days, as determined by cell morphology, loss of contact inhibition and anchorage dependent growth in culture, and acquired invasive properties and tumorigenicity in recipient athymic mice. Remarkably, NaPA prevented the development of these malignant phenotypes in the 5AzadC treated cultures (Table 1).

TABLE 1

| Treatment | Tumor Formation[a] | | Growth on matrigel[b] |
|---|---|---|---|
| | Incidence | Size (mm) | |
| None | 3/8 | 1 (0.5–2) | – |
| 5AzadC (0.1 uM) | 8/8 | 11.5 (4–19) | + |
| NaPA (1.5 mg/ml) | 0/8 | | – |
| 5AzadC + NaPA (0.1 uM) (1.5 mg/ml) | 0/8 | 0 | – |

[a]Cells protected in culture were injected s.c. (5 × 10$^5$ cells per site) into 1 month old female athymic nude mice (Division of Cancer Treatment, NCI Animal Program, Frederick Cancer Research Facility). Results indicate the incidence (tumor bearing/injected animals), as well as tumor size as mean (range), determined after 3 weeks.
[b]Cells were plated on top of matrigel (reconstituted basement membrane) and observed for malignant growth pattern, i.e., active replication, development of characteristic processes, and invasion.

3. Activity in Humans.

In terms of cancer prevention, the beneficial effect of NaPA to humans may be even more dramatic than that observed with the experimental models. In humans, NaPA is known to deplete circulating glutamine, an amino acid critical for the development and progression of cancer. The enzymatic reaction leading to glutamine depletion takes place in the liver and kidney. It is not clear whether or not glutamine depletion occurs in the cultured tumor cells. Moreover, molecular analysis revealed that NaPA induced the expression of histocompatibility class I antigens, which are localized on the surface of tumor cells and affect the immune responses of the host. While the therapeutic benefit of NaPA observed in cultures is in some cases reversible upon cessation of treatment, in patients the residual tumor cells would eventually be eliminated by the immune system. Even if chemoprevention will require continuous treatment with NaPA, such treatment would be acceptable considering the lack of toxicity.

Pharmaceutical compositions containing phenylacetate have been shown to cause reversal of malignancy and to induce differentiation of tumor cells. To demonstrate the capacity of drugs to induce differentiation of tumor cells, three in vitro differentiation model systems and one in vivo phase I clinical trial were used (further described herein). The first system used a human promyelocytic leukemia cell line HL-60. This cell line represents uncommitted precursor cells that can be induced to terminally differentiate along the myeloid or monocytic lineage. In the second system, immortalized embryonic mesenchymal C3H 10T1/2 cells were used which have the capability of differentiating into myocytes, adipocytes, or chondrocytes. In the third system, human erythroleukemia K562 cells were used because they can be induced to produce hemoglobin. Finally, the in vivo experiments demonstrated the efficacy of NaPA in inducing terminal differentiation in humans and animals.

NaPA and NaPB have also been shown to affect tumor growth in vitro and in animal models at pharmacological, non-toxic concentrations. These aromatic fatty acids induced cytostasis and promoted maturation of various human malignant cells, including hormone-refractory prostatic carcinoma, glioblastoma, malignant melanoma, and lung carcinoma. The marked changes in tumor biologoy were associated with alterations in the expression of genes implicated in tumor growth, invasion, anglogenesis, and immunogenicity. Multiple mechansims of drug action appear to be involved. These mechanisms include (a) modification of lipid metabolism, (b) regulation of gene expression through DNA hypomethylation and transcriptional activation, and (c) inhibition of protein isoprenylation. Phase I clinical trials confirmed the efficacy of these novel, non-toxic differentiation inducers (see Example 15).

Example 1:

HL-60 and 10T1/2 cells—PAG and NaPA treatment

Referring now to the data obtained using the first system (results illustrated in FIG. 1), logarithmically growing HL-60 [-•-] and 10T1/2 [-o-] cells were treated for four days with NaPA [solid line] or phenylacetylglutamate (PAG) [dashed line]. The adherent cells were detached with trypsin/ EDTA and the cell number determined using a hemocytometer. Data points indicate the mean±S.D. of duplicates from two independent experiments. The cell lines were obtained from the American Type Culture Collection and maintained in RPMI 1640 (HL-60) or Dulbecco's Modified Eagle's Medium (10T1/2) supplemented with 10% heat inactivated fetal calf serum (Gibco Laboratories), 2 mM L-Glutamine, and antibiotics. PAA (Sigma, St. Louis Mo.) and PAG were each dissolved in distilled water, brought to pH 7.0 by the addition of NaOH, and stored in −20° C. until used. As demonstrated in FIG. 1, NaPA treatment of the HL-60 and 10T1/2 cultures was associated with dose dependent inhibition of cell proliferation.

Example 2:

HL-60 cells—induction of granulocyte differentiation

Figure 2:
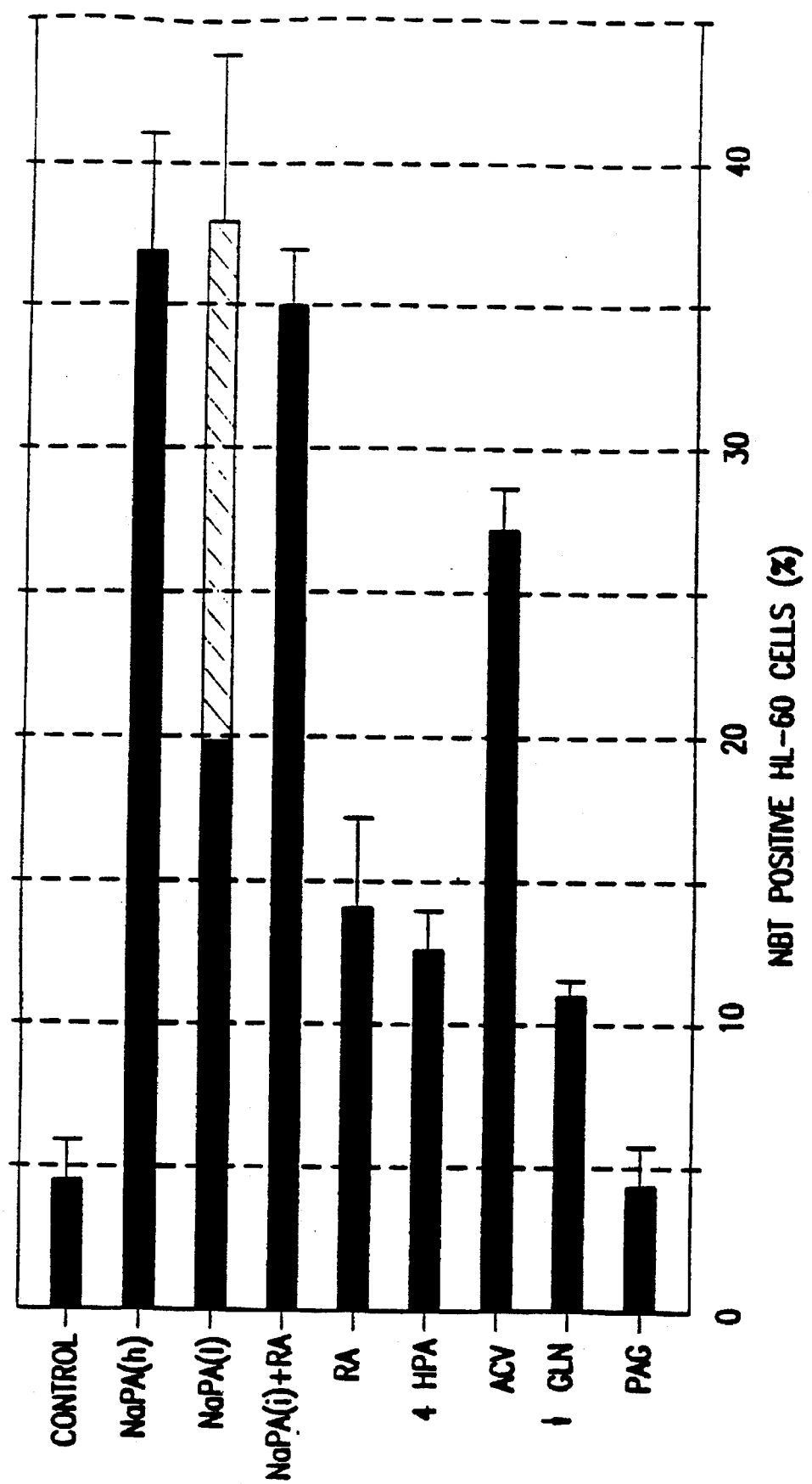
FIG. 2 shows the inducation of HL-60 cell differentiation. The number of NBT positive cells was determined after 4 [solid bars] or 7 days [hatched bars] of treatment. NaPA (h), 1.6 mg/ml; NaPA (1), 0.8 mg./ml. 4-hydroxyphenylacetate and PAG were used at 1.6 mg./ml. Potentiation by RA 10 nM was comparable to that by IFN gamma 300 IU/ml, and the effect of acivicin 3 μg/ml similar to DON 30 μg/ml. Glutamine Starvation (Gln, <0.06 mM) was as described. Cell viability was over 95% in all cases, except for DON and acivicin (75% and 63%, respectively).

To further evaluate the effectiveness of NaPA as an inducer of tumor cell differentiation, the ability of NaPA to induce granulocyte differentiation in HL-60 was investigated. The ability of cells to reduce nitroblue tetrazolium (NBT) is indicative of oxidase activity characteristic of the more mature forms of human bone marrow granulocytes. NBT reduction thus serves as an indicator of granulocyte differentiation. In FIG. 2, the number of NBT positive cells was determined after 4 days [solid bars] or 7 days [hatched bar] of treatment. NaPA (h), 1.6 mg/ml; NaPA (1), 0.8 mg/ml. 4-hydroxyphenylacetate (4HPA) and PAG were used at 1.6 mg/ml. Potentiation by retinoic acid (RA) 10 nM was comparable to that by interferon gamma 300 IU/ml. The direction of differentiation towards granulocytes in cultures treated with NaPA, whether used alone or in combination with RA, was confirmed by microscopic evaluation of cells stained with Wright Stain and the lack of nonspecific esterase activity. The effect of acivicin (ACV) 1 μg/ml was similar to 6-diazo-5-oxo-L-norleucine (DON) 25 μg/ml. Glutamine starvation (Gln, <0.06 mM) was as described. Cell viability determined by trypan blue exclusion was over 95% in all cases, except for DON and ACV which were 75% and 63%, respectively. DON, ACV and HPA are glutamine antagonists. As illustrated in FIG. 2, it is clear that NaPA is capable of inducing granulocyte differentiation in HL-60. As further illustrated in FIG. 2, differentiation of HL-60, assessed morphologically and functionally, was sequential and could be further enhanced by the addition of low doses of retinoic acid IRA, 10 nM) or interferon gamma (300

IU/ml). After seven days of NaPA treatment, or four days, when combined with RA, the HL-60 cultures were composed of early stage myelocytes and metamyelocytes (30–50%), as well as banded and segmented neutrophils (30–40%) capable of NBT.

Pharmacokinetics studies in children with urea cycle disorders indicate that infusion of NaPA 300–500 mg/kg/day, a well tolerated treatment, results in plasma levels of approximately 800 µg/ml. [Brusilow, S. W. et al. Treatment of episodic hyperammonemia in children with inborn errors of urea synthesis. *The New England Journal of Medicine*. 310:1630–1634 (1984).] This same concentration was shown to effectively induce tumor cell differentiation in the present experimental system.

Example 3:

10T1/2 cells—NaPA induction of adipocyte conversion

Figure 3:
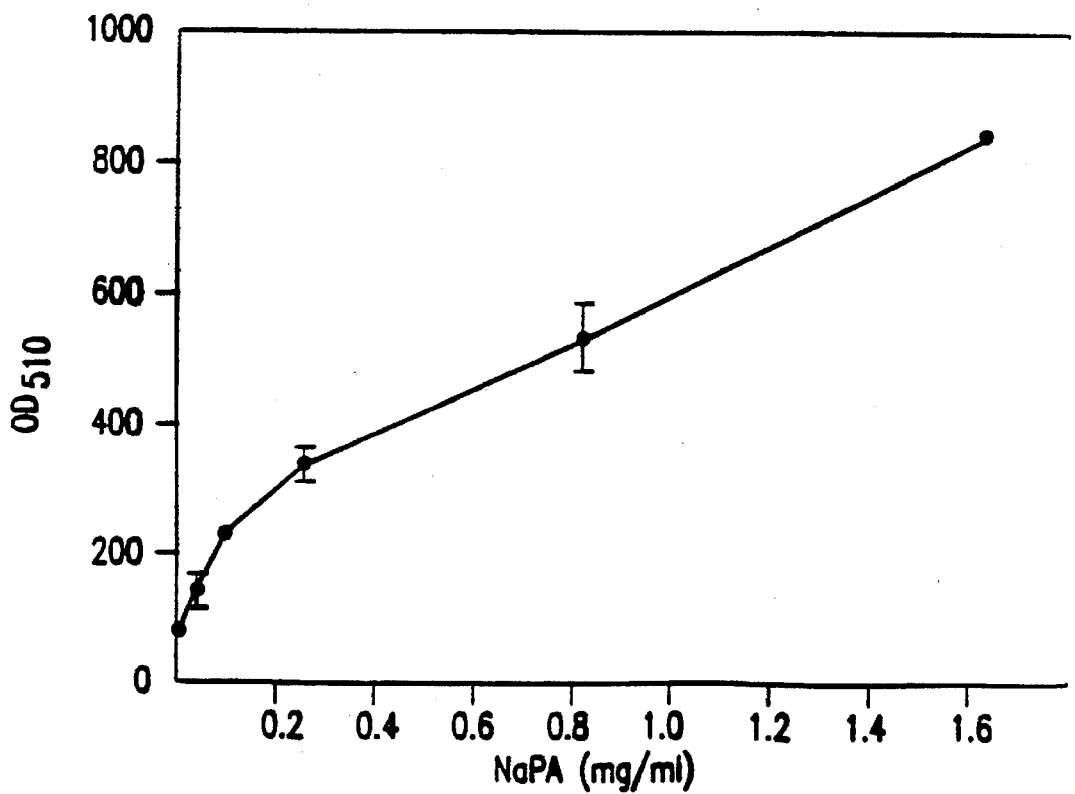
FIG. 3 shows adipocyte conversion in 10T1/2 cultures.

FIG. 3 illustrates that NaPA is capable of inducing adipocyte conversion in 10T1/2 cultures. Confluent cultures were treated with NaPA for seven days. Lower: Quantitation of adipocytosis. Cells were fixed with 37% formaldehyde and stained with Oil-Red O. The stained intracellular lipid was extracted with butanol, and the optical density was determined using a Titertek Multiskan MC, manufactured by Flow Laboratories, at a wavelength 510 nm. Increased lipid accumulation was evident in cells treated with as little as 0.024 mg/ml of NaPA. The results in FIG. 3 show that differentiation was dose- and time-dependent, and apparently irreversible upon cessation of treatment. NaPA at 800 µg/ml was efficient and totally free of cytotoxic effect. In the 10T1/2 model, adipocyte conversion involved over 80% of the cell population. It was noted that higher drug concentrations further increased the efficiency of differentiation as well as the size of lipid droplets in each cell.

It is known that glutamine conjugation by NaPA is limited to humans and higher primates and that in rodents NaPA instead binds glycine. [James, M. O. et al. The conjugation of phenylacetic acid in man, sub-human primates and some non-primate species. *Proc. R. Soc. Lond. B.* 182:25–35 (1972).] Consequently, the effect of NaPA on the mouse 10T1/2 cell line could not be explained by an effect on glutamine. In agreement, neither glutamine starvation nor treatment with glutamine antagonists such as DON and ACV resulted in adipocyte conversion.

Example 4:

Induction of lipid accumulation and adipocyte differentiation

4. Clinical use of phenylacetate and derivatives

TABLE 2

Phenylacetate and Derivatives: Induction of cellular differentiation in premalignant 10T1/2 cells

| Compounds (sodium salts) | Differentiation at 1 mM (%) | DC$_{50}$* (mM) |
| --- | --- | --- |
| Phenylacetate | 65 | 0.7 |
| 1-naphthylacetate | >95 | <0.1 |
| 3-chlorophenylacetate | 80 | 0.5 |
| 4-chlorophenylacetate | 50 | 1.0 |
| 2,6-dichlorophenylacetate | 75 | 0.5 |
| 4-fluorophenylaceatae | 65 | 0.7 |

*DC$_{50}$, concentration of compound causing 50% differentiation

As shown in Table 2, phenylacetate and its derivatives efficiently induced lipid accumulation and adipocyte differentiation in premalignant cells. These and other results indicate that the tested compounds might be of value in:

A. Cancer prevention. Non-replicating, differentiated tumor cells are not likely to progress to malignancy.

B. Differentiation therapy of malignant and pathological nonmalignant conditions.

C. Treatment of lipid disorders, in which patients would benefit from increased lipid accumulation.

D. Wound healing. This is indicated by the ability of phenylacetate to induce collagen synthesis in fibroblasts (see and Section D herein).

Studies in plants have revealed that NaPA can interact with intracellular regulatory proteins and modulate cellular RNA levels. In an attempt to explore the possible mechanism of action, Northern blot analysis of HL-60 and 10T1/2 cells was performed according to conventional methods. Cytoplasmic RNA was extracted, separated and analyzed (20 µg/lane) from confluent cultures treated for 72 hours with NaPA or PAG (mg/ml); C is the untreated control. The aP2 cDNA probe was labeled with [32P]dCTP (New England Nuclear) using a commercially available random primed DNA labeling kit. Ethidium bromide-stained 28S rRNA indicates the relative amounts of total RNA in each lane.

The results of the Northern blot analysis of HL-60 and 10T1/2 cells, showed marked changes in gene expression shortly after NaPA treatment. Expression of the adipocyte-specific aP2 gene was induced within 24 hours in treated 10T1/2 confluent cultures reaching maximal mRNA levels by 72 hours.

Example 5:

HL-60 Cells—myc down regulation

In HL-60, cell transformation has been linked to myc amplification and over-expression, and differentiation would typically require down regulation of myc expression. [Collins, S. J. The HL-60 promyelocytic leukemia cell line: Proliferation, differentiation, and cellular oncogene expression. *Blood.* 70:1233–1244 (1987)]. To demonstrate the kinetics of myc inhibition and HLA-A induction, Northern blot analysis of cytoplasmic RNA (20 µg/lane) was carried out on cells treated with NaPA and PAG for specified durations of time and untreated controls (−). The dose-dependency and specificity of the effect of NaPA was observed. Two concentrations of NaPA, 1.6 mg/ml (++) and 0.8 mg/ml (+), and PAG at 1.6 mg/ml were investigated. The $^{32}$P-labeled probes used were myc 3rd exon (Oncor) and HLA-A3 Hind III/EcoRI fragment. NaPA caused a rapid decline in the amounts of myc mRNA. This occurred within 4 hours of treatment, preceding the phenotypic changes detectable by 48 hours, approximately two cell cycles, after treatment. Similar kinetics of myc inhibition have been reported for other differentiation agents such as dimethyl sulfoxide, sodium butyrate, bromodeoxyuridine, retinoids, and 1,25-dihydroxyvitamin D$_3$. The results observed suggest that down regulation of oncogene expression by NaPA may be responsible in part for the growth arrest and induction of terminal differentiation. In addition, it is evident that NaPA treatment of the leukemic cells was associated with time- and dose-dependent accumulation of HLA-A mRNA coding for class major histocompatibility antigens. This enhances the immunogenicity of tumors in vivo.

Example 6:

K562 cells—NaPA promotes hemoglobin biosynthesis

Further support for the use of NaPA as a non-toxic inducer of tumor cell differentiation is found in the ability of NaPA to promote hemoglobin biosynthesis in erythroleukemia cells. K562 leukemic cells have a nonfunctional beta-globin gene and, therefore, do not normally produce significant amounts hemoglobin. When K562 human erythroleukemia cells were grown in the presence of NaPA at 0.8 and 1.6 mg/ml concentrations, hemoglobin accumulation, a marker of differentiation, was found to increase 4 to 9 fold over that of control cells grown in the absence of NaPA. Hemoglobin accumulation was determined by Benzidine staining of cells for hemoglobin and direct quantitation of the protein. The results of this study are reported in Table 16.

It has been shown that high concentrations of NaPA inhibit DNA methylation in plants. [Vanjusin, B. J. et al. Biochemia 1, 46:47–53 (1981)]. Alterations in DNA methylation can promote oncogenesis in the evolution of cells with metastatic capabilities. [Rimoldi, D. et al. Cancer Research. 51:1–7 (1991)]. These observations prompted some concerns regarding potential long-term adverse effects with the use of NaPA. To determine the potential tumorigenicity of NaPA, a comparative analysis was performed using NaPA and the known hypomethylating agent 5-aza-2'-deoxycytidine (5AzadC).

Premalignant cells ($3-4 \times 10^5$) were plated in 75 cm$^2$ dishes and 5AzadC 0.1 µM was added to the growth medium at 20 and 48 hrs after plating. The cells were then subcultured in the absence of the nucleoside analog for an additional seven weeks. Cells treated with NaPA at 1.6 mg/ml were subcultured in the continuous presence of the drug. For the tumorigenicity assay, 4–5 week-old female athymic nude mice were inoculated s.c. with $1 \times 10^6$ cells and observed for tumor growth at the site of injection.

The results set forth in Table 3 show that NaPA, unlike the cytosine analog, did not cause tumor progression.

TABLE 3

Tumorigenicity of C3H 10T1/2 Cells in Athymic Mice

| Treatment | Tumors | | |
|---|---|---|---|
| | Incidence (positive/ injected mice) | Diameter (mm ± S.D.) | Time (weeks) |
| None | 0/8 | 0 | 13 |
| 5AzadC | 8/8 | 5.5 ± 2.5 | 8 |
| NaPA | 0/8 | 0 | 13 |

The transient treatment of actively growing 10T1/2 cells with 5AzadC resulted in the development of foci of neoplastically transformed cells with a frequency of about $7 \times 10^{-4}$. These foci eventually became capable of tumor formation in athymic mice. By contrast, actively replicating 10T1/2 cultures treated for seven weeks with NaPA, 800–1600 µg/ml, differentiated solely into adipocytes, forming neither neoplastic foci in vitro nor tumors in vivo in recipient mice.

Furthermore, experiments have demonstrated that NaPA can prevent spontaneous or 5AzadC-induced neoplastic transformation, thus demonstrating its novel role in cancer prevention. It is known that the treatment of premalignant 4C8 and 10T1/2 cells with carcinogens such as 5AzadC produces malignant conversion of the respective cells. When 4C8 [Remold: et al., Cancer Research, 51:1–7 (1990)] and 10T1/2 cells were exposed to 5AzadC, malignant conversion became evident in two days and two weeks, respectively. NaPA (0.8–1.6 mg/ml) prevented the appearance of the malignant phenotype, as determined by cell morphology, contact inhibition and anchorage dependent growth in culture.

Example 7:

Growth arrest in malignant gliomas

In addition, Phenylacetate has been implicated in damage to immature brain in phenylketonuria. Because of similarities in growth pattern and metabolism between the developing normal brain and malignant central nervous system tumors, phenylacetate may be detrimental to some brain cancers. Phenylacetate can induce cytostasis and reversal of malignant properties of cultured human glioblastoma cells, when used at pharmacological concentrations that are well tolerated by children and adults. Interestingly, treated tumor cells exhibited biochemical alterations similar to those observed in phenylketonuria-like conditions, including selective decline in de novo cholesterol synthesis from mevalonate. Since gliomas, but not mature normal brain cells, are highly dependent on mevalonate for production of sterols and isoprenoids vital for cell growth, phenylacetate would be expected to affect tumor growth in vivo, while sparing normal tissues. Systemic treatment of rats bearing intracranial gliomas resulted in significant tumor suppression with no apparent toxicity to the host. The experimental data, which are consistent with clinical evidence for selective activity against undifferentiated brain, suggest that phenylacetate may offer a safe and effective novel approach to treatment of malignant gliomas.

Clinical experience, obtained during phenylacetate treatment of children with urea cycle disorders, indicates that millimolar levels can be achieved without significant adverse effects. The lack of neurotoxicity in these patients is, however, in marked contrast to the severe brain damage documented in phenylketonuria (PKU), an inborn error of phenylalanine metabolism associated with excessive production of phenylacetate, microcephaly, and mental retardation. [Scriver, C. R., and C. L. Clow. 1980. Phenylketonuria: epitome of human biochemical genetics. New Engl. J. Med. 303: 1394–1400.] The differences in clinical outcome can be explained by the fact that, although phenylacetate readily crosses the blood-brain barrier in both prenatal and postnatal life, neurotoxicity is limited to the immature brain. Compelling evidence for a developmentally restricted window of susceptibility is provided by the phenomenon of "maternal PKU syndrome": PKU females who are diagnosed early and maintained on a phenylalanine-restricted diet, develop normally and subsequently tolerate a regular diet. These women often give birth to genetically normal, yet mentally retarded infants due to the untreated maternal PKU. The elevated levels of circulating phenylacetate, while sparing the mature tissues of the mother, are detrimental to the fetal brain. The primary pathological changes in PKU involve rapidly developing glial cells and are characterized by alterations in lipid metabolism and myclination with subsequent neuronal dysfunction. The vulnerable fetal glial tissues resemble neoplastic glial cells in numerous molecular and biochemical aspects, including unique dependence upon mevalonate (MVA) metabolism for synthesis of sterols and isoprenoids critical to cell replication [Kandutsch, A. A., and S. E. Saucier. 1969. Regulation of sterol synthesis in developing brains of normal and jimpy mice. Arch. Biochem. Biophys. 135: 201–208; Fumagalli, R., E. Grossi, P. Paoletti, and R.

Paoletti. 1964. Studies on lipids in brain tumors. I. Occurrence and significance of sterol precursors of cholesterol in human brain tumors. *J. Neurochem.* 11: 561–565; Grossi, E., P. Paoletti, and R. Paoletti. 1958. An analysis of brain cholesterol and fatty acid biosynthesis. *Arch. Int. Physiol. Biochem.* 66: 564–572], and on circulating glutamine as the nitrogen donor for DNA, RNA and protein synthesis [Perry, T. L., S. Hasen, B. Tischler, R. Bunting, and S. Diamond. 1970. Glutamine depletion in phenylketonuria, a possible cause of the mental defect. *New Engl. J. Med.* 282: 761–766; Weber, G. 1983. Biochemical strategy of cancer cells and the design of chemotherapy: G.H.A. Clowes Memorial Lecture. *Cancer Res.* 43: 3466–3492]. The hypothesis underlying these studies was that phenylacetate, known to conjugate and deplete serum glutamine in humans, and to inhibit the MVA pathway in immature brain [Castillo, M., M. F. Zafra, and E. Garcia-Peregrin. 1988. Inhibition of brain and liver 3-hydroxy-3-methylglutaryl-CoA reductase and mevalonate-5-pyrophosphate decarboxylase in experimental hyperphenylalaninemia. *Neurochem. Res.* 13: 551–555; Castillo, M., J. Iglesias, M. F. Zafra, and E. Garcia-Peregrin. 1991. Inhibition of chick brain cholesterogenic enzymes by phenyl and phenolic derivatives of phenylalanine. *Neurochem. Int.* 18: 171–174; Castillo, M., M. Martinez-Cayuela, M. F. Zafra, and E. Garcia-Peregrin. 1991. Effect of phenylalanine derivatives on the main regulatory enzymes of hepatic cholestrogenesis. *Mol. Cell. Biochem.* 105: 21–25], might attack these critical control points in malignant gliomas. The efficacy of phenylacetate was demonstrated using both in vitro and in vivo tumor models.

Cell Cultures and Reagents. Human glioblastoma cell lines were purchased from the American Type Culture Collection (ATCC, Rockville, Md.), and maintained in RPMI 1640 supplemented with 10% heat inactivated fetal calf serum, antibiotics and 2 mM L-glutamine, unless otherwise specified. Human umbilical vein endothelial cells, isolated from freshly obtained cords, were provided by D. Grant and H. Kleinman (NIH, Bethesda Md.). Sodium salts of phenylacetic acid and of phenylbutyric acid were provided by Elan Pharmaceutical Corporation (Gainseville, Ga.). Phenylacetylglutamine was a gift from S. Brusilow (Johns Hopkins, MD).

Evaluation of Cell Replication and Viability. Growth rates were determined by an enzymatic assay using 3-[4,5-dimethylthiazol-2-yl]-2,5-diphenyltertrazolium bromide (Sigma, St. Louis, Mo.) [Alley, M. C., D. A. Scudiero, A. Monks, M. L. Hursey, M. J. Czerwinski, D. L. Fine, B. J. Abbott, J. G. Mayo, R. H. Schoemaker, and M. R. Boyd. 1988. Feasibility of drug screening with panels of human tumor cell lines using a microculture tetrazolium assay. *Cancer Res.* 48: 589–601], cell enumeration with a hemocytometer following detachment with trypsin/EDTA, and by thymidine incorporation into DNA. The different assays produced essentially the same results. Cell viability was assessed by trypan blue exclusion.

Colony Formation in Semi-Solid Agar. Tumor cells were detached with trypsin/EDTA, re-suspended in growth medium containing 0.36% agar, and placed onto a base layer of solid agar (0.9%) in the presence or absence of drugs. Colonies composed of 30 or more cells were scored after three weeks.

Immunocytochemistry. Cells were immunostained with anti-vimentin monoclonal antibodies using Dako PAP kit K537 (Dako Corporation, CA).

Measurement of Cholesterol, Protein and DNA Synthesis. For studies of steroid synthesis, cells were labeled for 24 hours with $5 \times 10^6$ DPM [5-$^3$H]-mevalonate (35 Ci/mmol) (New England Nuclear, Boston, Mass.) in growth medium containing 3 µM lovastatin and 0.5 mM unlabeled mevalonate, in the presence or absence of 5 mM phenylacetate or 2.5 mM phenylbutyrate. Cellular steroids were extracted with hexane and separated by silica thin layer chromatography. The $R_f$ of the hexane-soluble radiolabled product was identical to that of a radiolabled cholesterol standard in three different solvent systems. Similarly treated cells were tested for de novo protein and DNA synthesis by metabolic labeling with [$^3$H]-leucine (158 Ci/mmol) or [3H]-deoxythymidine (6.7 Ci/mmol)(New England Nuclear). Measurements of $^{14}CO_2$ released from [1-$^{14}$C]-mevalonate (49.5 mCi/mmol) (Amersham, Chicago, Ill.) in cell homogenates incubated with phenylacetate/phenylbutyrate were performed with minor modifications to established procedures.

Analysis of Protein Isoprenylation. Cell cultures were incubated with 10 mM phenylacetate or 2.5 mM phenylbutyrate for 24 hours in complete growth medium, and labeled with RS-[2-$^{14}$C]-mevalonate (16 µCi/ml, specific activity 15 µCi/mmol) (American Radiolabeled Chemicals, Inc. St. Louis, Mo.) during the final 15 hours of treatment. Whole cell proteins were extracted, resolved on 10% SDS-polyacrylamide gels, and stained with Commassie Brilliant Blue. Gels were then dried and exposed to Kodak X-Omat film for 4 days.

Animal Studies. To determine the effect of phenylacetate on the tumorigenic phenotype of human glioblastoma cells, cultures were pre-treated for one week and then harvested, resuspended in medium containing 30% matrigel (Collaborative Biomedical Products, Bedford, Mass.), and transplanted s.c. ($2.5 \times 10^6$ cells per site) into 5-week old female athymic mice (Division of Cancer Treatment, NCI Animal Program, Frederick Cancer Research Facility). The animals were then observed for tumor growth at the site of injection. To further evaluate drug efficacy in vivo, Fisher 344 rats received a stereotaxic inoculation of syngeneic 9L gliosarcoma cells ($4 \times 10^4$) into the deep white matter of the right cerebral hemisphere, as previously described [Weizsaecker, M., D. F., Deen, M. L. Rosenblum, T. Hoshino, P. H. Gutin, and M. Baker. 1981. The 9L rat brain tumor: description and application of an animal model. *J. Neurol.* 224: 183–192; Culver, K. W., Z. Ram, S. Walbridge, H. Ishii, E. H. Oldfield, and R. M. Blaese. 1992. In vivo gene transfer with retrovital vector producer cells for treatment of experimental brain tumors. *Science.* 256: 1550–1552]. The animals were then subjected to two weeks of continuous treatment with sodium phenylacetate (550 mg/kg/day, s.c.), using osmotic minipumps transplanted subcutaneously. In control rats the minipumps were filled with saline. Statistical analysis of data employed the Fisher's Exact Test.

Figure 4:
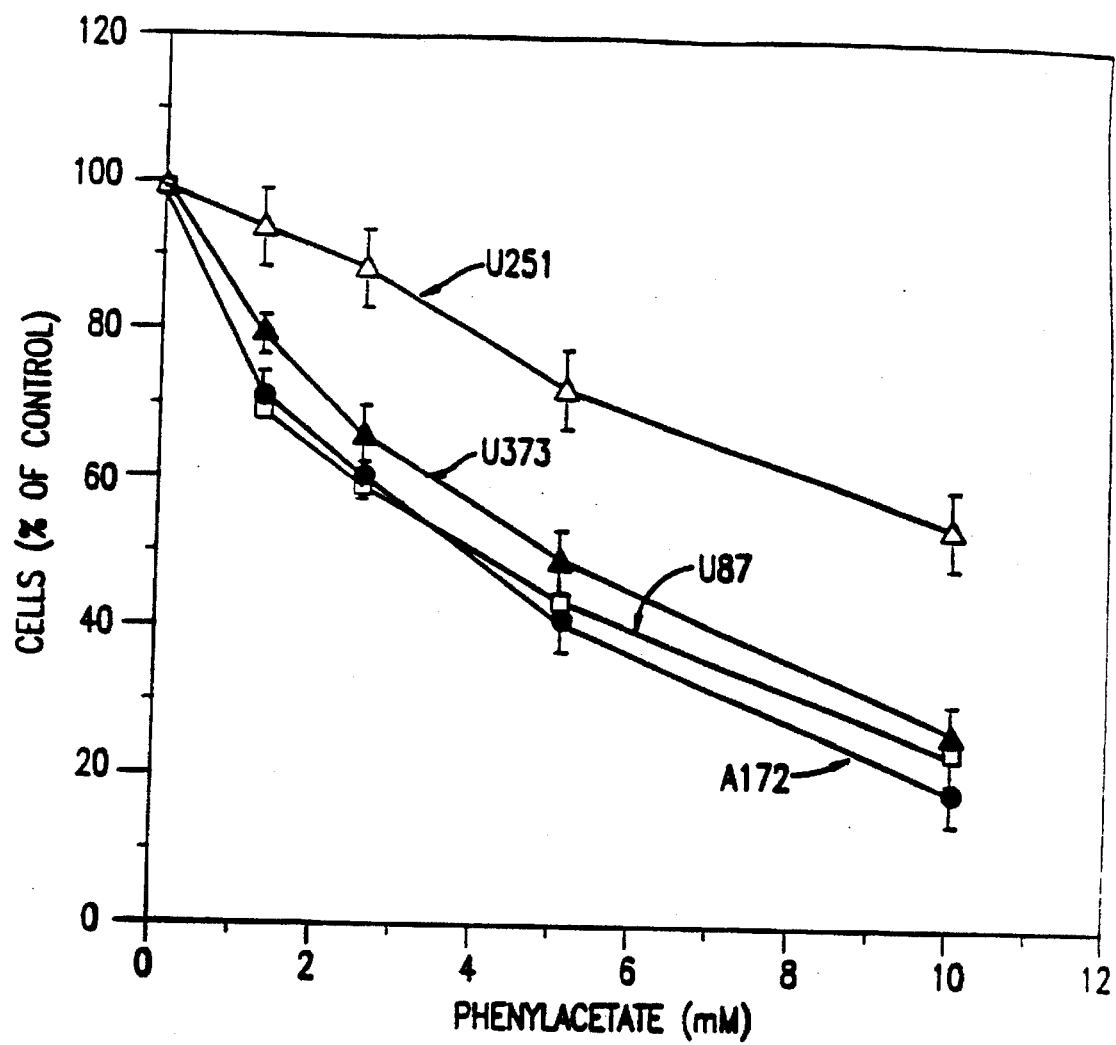
FIG. 4 shows NaPA's ability to invoke growth arrest of human glioblastoma cells. Dose-dependent inhibition of human glioblastoma cell proliferation by sodium phenylacetate. Growth rates were determined, after 4–5 days of continuous treatment, by an enzymatic assay using 3-[4,5-dimethylthiazol-2-yl]-2,5-diphenyltertrazolium bromide and confirmed by cell enumeration with a hemocytometer. Reduction in cell number paralleled changes in de novo DNA synthesis (not shown).
Figure 5:
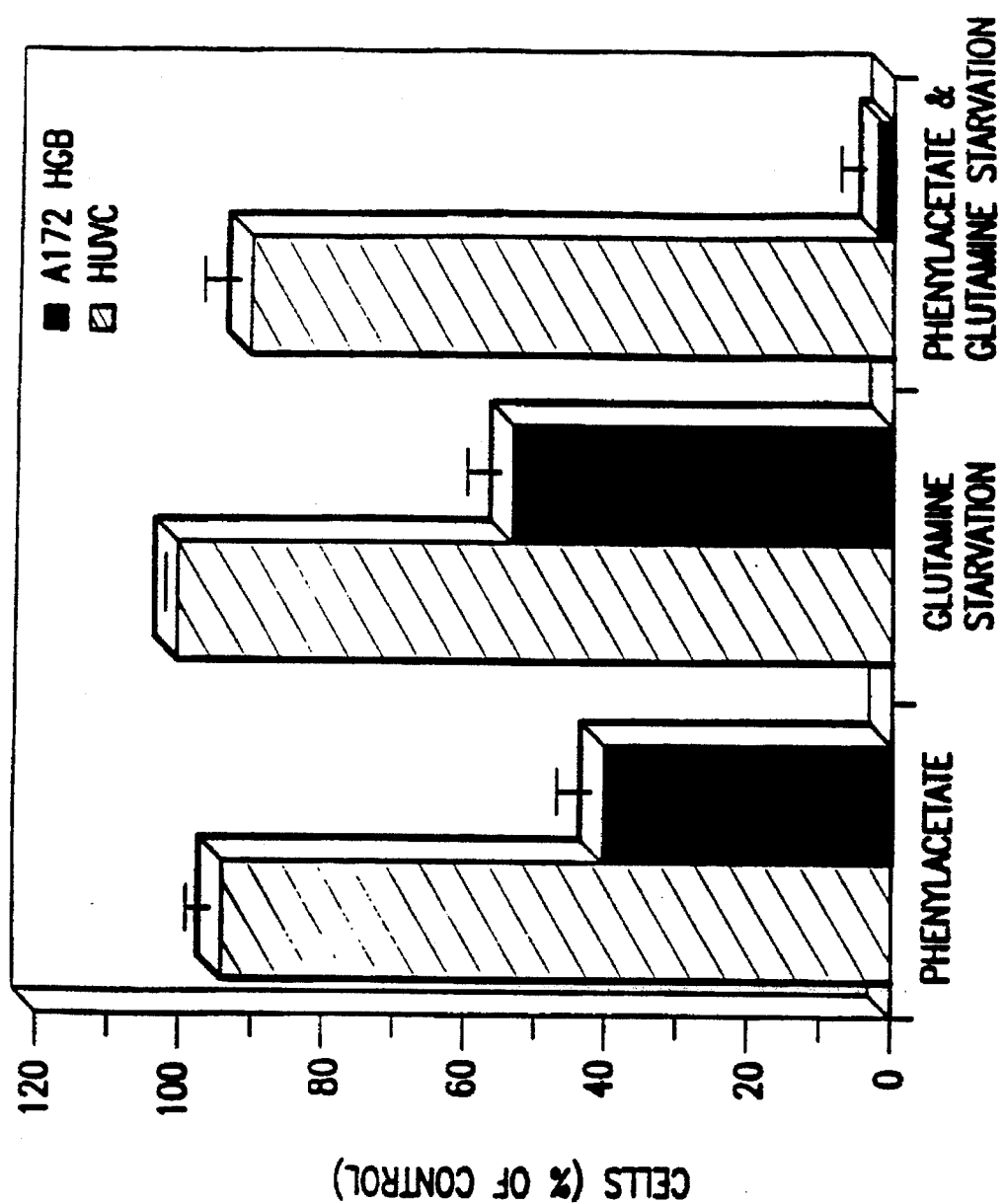
FIG. 5 shows selective cytostatis induced by phenylacetate (5 mM) combined with glutamine starvation (0.2 mM glutamine, i.e., 2–3 fold below the normal plasma levels). The results indicate increased vulnerability of glioblastoma A172 when compared to actively replicating normal human umbilical vein endothelial cells (HUVC). Cell viability was over 95% in all cases.

Induction of cytostasis and phenotypic reversion in cultured human glioblastoma cells. Treatment of glioblastoma cells with phenylacetate resulted in time- and dose-dependent growth arrest (FIG. 4), accompanied by similarly diminished DNA synthesis. After 4–6 days of continuous treatment with 4 mM phenylacetate, there was approximately 50% inhibition of growth in U87, A172, U373, U343, and HS683 cultures ($IC_{50}$ 4.4±0.6 mM). Reflecting on the heterogenous nature of tumor cell responses, glioblastoma U251 and U138 cells were less sensitive with $IC_{50}$ values of 8–10 mM. Further studies, mimicking pharmacological conditions that are expected in patients, involved exposure of cells to phenylacetate in glutamine-depleted medium. These conditions completely blocked glioblastoma cell growth, but had little effect on the replication of normal endothelial cells (FIG. 5). Phenylbutyrate, an intermediate metabolite of phenylacetate formed in the brain by fatty acid elongation, also inhibited tumor cell replication ($IC_{50}$ 2.2±0.2 mM in A172, U87 and U373), while the end metabolite, phenylacetylglutamine, was inactive. In addition to inducing selective tumor cytostasis, both phenylacetate and phenylbutyrate promoted cell maturation and reversion to a nonmalignant phenotype, manifested by an altered pattern of cytoskeletal intermediate filaments, loss of anchorage-independence, and reduced tumorigenicity in athymic mice (Table 4). Immunocytocemical analysis of vimentin in phenylacetate-treated human glioblastoma U87 cells showed altered morphology and cytoskeletal filament pattern. These changes, confirmed by immunolabeling for glial fibrillary acidic protein are consistent with cell maturation and correlate with reduced proliferative capacity and regained contact inhibition of growth. These profound changes in tumor behavior were accompanied by alterations in the expression of genes implicated in growth control, angiogenesis, and immunosuppression (e.g., TGFα, HbF, and TGF-β2).

TABLE 4

Reversal of Malignancy of Human Glioblastoma Cells

| Treatment | Clonogenicity in Soft Agar[1] (%) | Tumor Incidence[2] Positive/Injected Sites |
|---|---|---|
| None | 8.1 | 9/10 |
| Phenylacetate | | |
| 2.5 mM | 0.5 | ND |
| 5 mM | >0.01 | 2/10 |
| Phenylbutyrate | | |
| 1.25 mM | 0.15 | ND |
| 2.5 mM | >0.01 | 1/10 |

[1]U87 cells were detached with trypsin/EDTA, resuspended in growth medium containing 0.36% agar, and placed onto a base layer of solid agar (0.9%) in the presence or absence of drugs. Colonies composed of 30 or more cells were scored after three weeks.
[2]U87 cells pre-treated in culture for one week, were harvested, resuspended in medium containing 30% matrigel, and transplanted s.c. into 5-week old female athymic mice (2.5 × 10⁶ cells per mouse). Data were recorded 5 weeks after cell inoculation.
ND = not determined.

Figure 6:
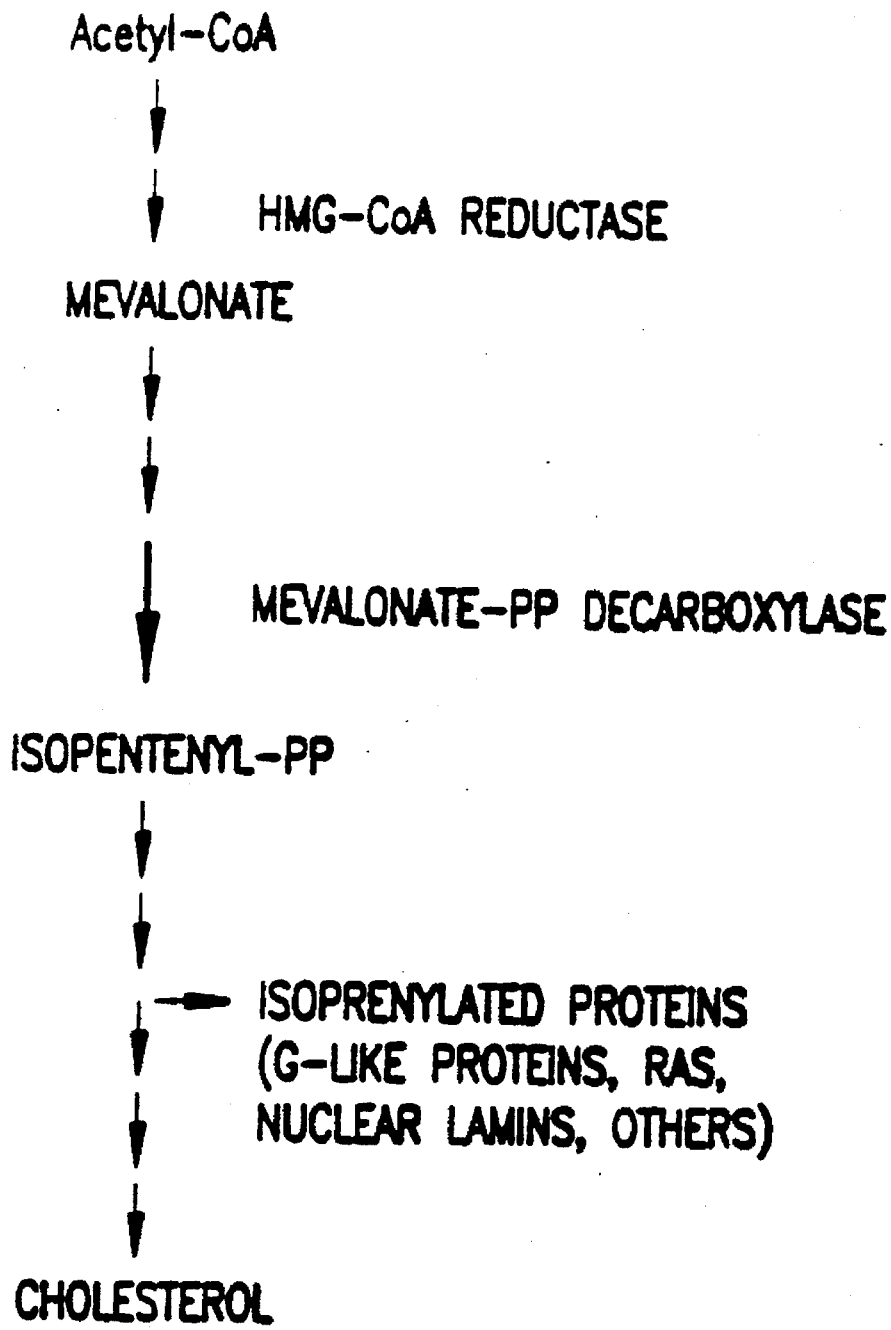
FIG. 6 shows that phenylacetate inhibits the mevalonate pathway of cholesterol synthesis in glioblastoma cells.
Figure 7:
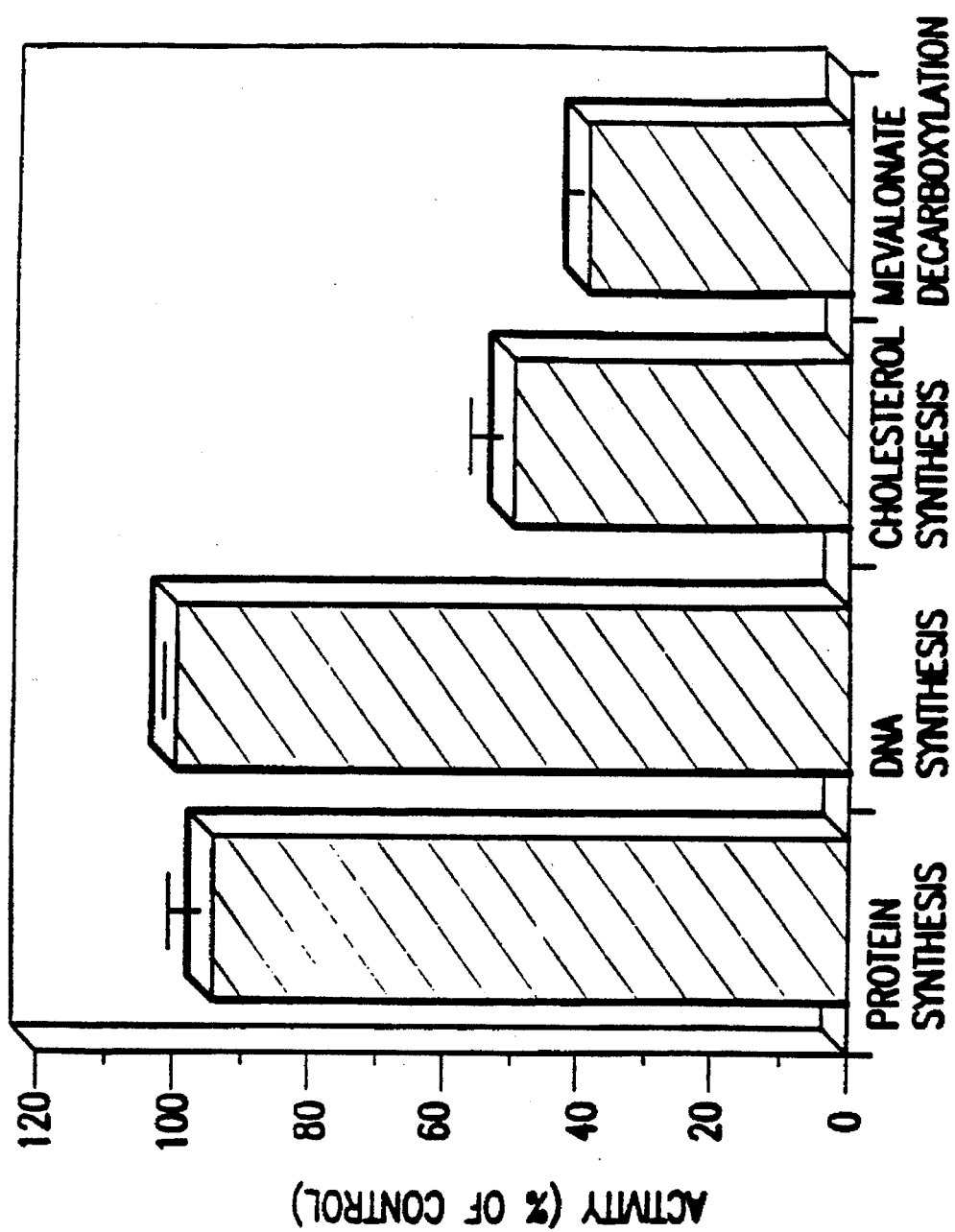
FIG. 7 shows the selective inhibition of cholesterol synthesis from mevalonate in phenylacetate-treated glioblastoma U87 cells, and enzymatic inhibition of mevalonate decarboxylation in cell homogenates. For analysis of steroid synthesis, logarithmically growing cells were labeled with tritiated MVA in the presence or absence of 5 mM phenylacetate, and their steroids were separated by silica thin layer chromatography. MVA decarboxylation was measured in cell homogenates. The effect of phenylacetate on cholesterol synthesis and MVA decarboxylation was selective as, under the experimental conditions used, total protein and DNA synthesis levels were unaffected.

Phenylacetate inhibits the mevalonate pathway and protein isoprenylation. The most consistent biochemical change observed in glial cells exposed to phenylacetate involved alterations in lipid metabolism and inhibition of the MVA pathway (FIG. 6). Active de novo synthesis of cholesterol and isoprenoids from precursors such as acetyl-CoA and MVA is an important feature of the developing brain (but not the mature brain), coinciding with myclination. It is also a hallmark of malignant gliomas [Azarnoff, D. L., G. L. Curran, and W. P. Williamson. 1958. Incorporation of acetate-1-$^{14}$C into cholesterol by human intracranial tumors in vitro. *J. Nat. Cancer Inst.* 21: 1109–1115; Rudling, M. J., B. Angelin, C. O. Peterson, and V. P. Collins. 1990. Low density lipoprotein receptor activity in human intracranial tumors and its relation to cholesterol requirement. *Cancer Res.* 50 (suppl): 483–487]. Cholesterol production and protein isoprenylation diminished within 24 hours of glioblastoma treatment with either phenylacetate or phenylbutyrate (FIG. 7), preceding changes in DNA and total protein synthesis, which were detectable after 48 hours. The reduction in isoprenylation was paralleled by a decrease in MVA decarboxylation (to less than 50% of control), an effect previously observed in embryonic brain in PKU-like conditions. MVA-5-pyrophosphate decarboxylase, a key enzyme regulating cholesterol synthesis in brain, is inhibited by phenylacetate under conditions in which MVA kinase and MVA-5-phosphate kinase are only minimally affected. Phenylacetate might also interfere with MVA synthesis from acetyl-CoA. Glioblastoma cells could not, however, be rescued by exogenous MVA (0.3–3 mM), suggesting that MVA utilization, rather than its synthesis, is the prime target. The decline in MVA decarboxylation and protein isoprenylation in phenylacetate-treated cells could be mimicked by using 1–2.5 mM phenylbutyrate.

Mevalonate is a precursor of several isopentenyl moieties required for progression through the cell cycle such as sterols, dolichol, the side chains of ubiquinone and isopentenyladenine, and prenyl groups that modify a small set of critical proteins [Goldstein, J. L., and M. S. Brown. 1990. Regulation of the mevalonate pathway. *Nature*. 343: 425–430; Marshall, C. J. 1993. Protein prenylation: A mediator of protein-protein interactions. *Science*. 259: 1865–1866; Braun, P. E., D. De Angelis, W. W. Shtybel, and L. Bernier. 1991. Isoprenoid modification permits 2',3'-cyclic nucleotide 3'-phosphodiesterase to bind to membranes. *J. Neurosci. Res.* 30: 540–544]. The latter include plasma membrane G and G-like proteins (e.g., ras) involved in mitogenic signal transduction (molecular weight 20–26 kDa), the myelination-related enzyme 2',3'-cyclic nucleotide 3'-phosphodiesterase, and nuclear envelope lamins that play a key role in mitosis (44–74 kDa). Inhibition of sterol and isoprenoid synthesis during rapid development of the brain could lead to the microcephaly and impaired myelination seen in untreated PKU. Targeting MVA in dedifferentiated malignant gliomas, on the other hand, would be expected to inhibit tumor growth in vivo without damaging the surrounding normal tissues, as the MVA pathway is significantly less active in mature brain.

Activity of phenylacetate in experimental gliomas in rats. To evaluate the in vivo antitumor effect of phenylacetate, Fisher rats were inoculated with stereotaxic intracerebral injection of syngeneic 9L gliosarcoma cells. This tumor model is known for its aggressive growth pattern that results in nearly 100% mortality of rats within 3 to 4 weeks. Phenylacetate was continuously administered by implanted subcutaneous osmotic minipumps to deliver a clinically-achievable dose of 550 mg/kg/day. Systemic treatment for two weeks of rats bearing intracranial glioma cells markedly suppressed tumor growth (p<0.05, Table 5) with no detectable adverse effects. Further studies in experimental animals indicate that phenylacetate (plasma and cerebrospinal fluid levels of 2–3 mM) induces tumor cell maturation in vivo and significantly prolongs survival.

TABLE 5

Phenylacetate Activity in Experimental Brain Cancer

| Treatment[1] | No. of animals | Brain Tumors[2] Macro-scopic | Micro-scopic | Tumor Free |
|---|---|---|---|---|
| Saline | 10 | 8 | 1 | 1 |
| Phenylacetate | 15 | 3 | 4 | 8 |

[1]Fisher 344 rats received a stereotaxic inoculation of syngeneic 9L gliosarcoma cells into the deep white matter of the right cerebral hemisphere, as described in Material and Methods. Animals were then subjected to two weeks of continuous treatment with either sodium phenylacetate (550 mg/kg/day, s.c.) or saline, using osmotic minipumps transplanted subcutaneously.
[2]Animals were sacrificed 23 days after tumor inoculation to determine antitumor effects. Findings were confirmed by histological evaluation of the inoculated site.

Summary and Prospective. Phenylacetate has long been implicated in damage to the developing fetal brain. As primary CNS tumors are highly reminiscent of immature fetal brain, malignant gliomas should be equally vulnerable. Moreover, viewing maternal PKU syndrome as a natural human model, phenylacetate would be expected to suppress the growth of brain neoplasms without harming normal tissues. Experimental data supports this hypothesis. Phenylacetate induced selective cytostasis and promoted maturation of glioma cells in vitro and in vivo. Premature growth arrest and differentiation could also underlie the damage to fetal brain in PKU. Multiple mechanisms of action are involved, including inhibition of protein isoprenylation and depletion of plasma glutamine in humans. The demonstrable antitumor activity, lack of toxicity, and ease of administration (oral or intravenous), demonstrate the clinical efficacy of phenylacetate in management of malignant gliomas, and perhaps of other neoplasms as well. Previously, phenylacetate showed activity in prostate cancer in vitro. Phase I clinical studies with phenylacetate in the treatment of adults with cancer confirmed that therapeutic levels can be achieved in the plasma and cerebrospinal fluid with no significant toxicities, and provide preliminary evidence for benefit to prostatic carcinoma and glioblastoma patients (see Example 18).

Phenylacetate was used to treat human solid tumors, including prostatic carcinoma, glioblastomas, and malignant melenoma. Treatment resulted in selective cytostasis and phenotypic reversion, as indicated by the restored anchorage-dependence, reduced invasiveness and loss of tumorigenicity in athymic-mice. Molecular analysis of brain and hormone-refractory prostate cancer cells revealed marked decline in the production and secretion of TGFβ, a protein implicated in growth control, angiogenesis, and immunosuppression. Treated prostatic cells exhibited decreased proteolytic activity mediated by urokinase-plasminogen activator, a molecular marker of disease progression in man.

Example 8:

Growth arrest, tumor maturation, and extended survival in brain tumors treated with NaPA In Vitro Studies.

Cell proliferation. The effect of NaPA on cell proliferation was evaluated using tritiatedthymidine incorporation assay on cultured 9L gliosarcoma cells and cell enumeration using a hemocytometer following detachment with trypsin/EDTA. 9L is a syngeneic malignant glial tumor derived from Fischer 344 rats and is associated with 100% mortality within three to four weeks after intracerebral inoculation [Weizsaecker M, Deen D F, Rosenblum M L, et al. The 9L rat brain tumor: description and application of an animal model. *J Neuol.* 1981; 224: 183–192]. Tumor cells were plated at $5 \times 10^4$ tumor cells/well in 24-well plates (Costar, Cambridge, Mass.) in Dulbecco Modified Eagle's medium (DMEM) with 10% fetal bovine serum (Hyclone Laboratories Inc., Logan, Utah), 2 mM L-glutamine (GIBCO BRL, Gaithersburg, Md.), 50 U/ml penicillin (GIBCO) and 50 µg/ml streptomycin (GIBCO) and 2.5 µg/ml Fungizone (ICN Biomedicals Inc., Costa Mesa, Calif.). After 24 hours, the medium was changed and NaPA (Elan Pharmaceutical Research Corp., Gainesville, Ga.) added to the medium at 0, 2.5, 5, and 10 mM concentration for 5 days. Six hours before harvest, 0.5 mCi tritiatedthymidine (ICN Radiochemicals, Irvine, Calif.) was added to each well. Thymidine incorporation was determined by scintillation counting in triplicates.

Colony formation in semi-solid agar. Anchorage independent growth (the ability of cells to form colonies in semi-solid agar) is characteristic of malignant glial cells. 9L cells were harvested with trypsin/EDTA and resuspended at $1.0 \times 10^4$ cells/ml in growth medium containing 0.36% agar (Difco). Two ml of the cell suspension was added to 60 mm plates (Costar, Cambridge, Mass.) which were precoated with 4 ml of solid agar (0.9%). Phenylacetate was added to the agar at different concentrations (0, 1.25, 2.5, and 5 mM). In a second experiment, 9L cells were grown for 7 days in tissue culture containing 5 mM NaPA. The cells were then transferred, as described, to agar plates without NaPA. Colonies composed of 30 or more cells were counted after 3 weeks.

9L brain tumor inoculation and phenylacetate administration. Fisher 344 rats (n=50) weighing 230–350 grams were anesthetized using intraperitoneal (i.p.) Ketamine (90 mg/Kg, Fort Dodge Laboratories, Inc., Fort Dodge, Iowa) and Xylazine (10 mg/Kg, Mobay Corporation, Shawnee, Kans.) and placed in a steriotaxic apparatus (David Kopf Instruments, Tujunga, Calif.). $4 \times 10^4$ syngeneic 9L gliosarcoma cells in 5 µL (Hank's) balanced salt solution were injected into the deep white matter (depth of inoculation—3.5 mm) of the right cerebral hemisphere using a 10 µL Hamilton syringe connected to the manipulating arm of the sterotaxic apparatus. In 10 rats, phenylacetate was administered by continuous subcutaneous (s.c.) release of the drug using two 2ML2 osmotic pumps release rate of 5 µl/hr for 14 days (Alza Corporation, Palo Alto, Calif.). On the day of tumor inoculation the pumps were implanted in the subcutaneous tissue of both flanks. The concentration of the drug in the pumps was 650 mg/ml (total of 2600 mg for both pumps) for a daily dose of 550 mg/kg per rat. The minipumps were replaced after 14 days for a total treatment of 28 days. Fifteen additional rats received NaPA, as described, starting 7 days after intracerebral inoculation of the tumor. In these rats, an additional daily injection of NaPA (300 mg/kg, i.p.) was given for 28 days. Control rats (n=25) received continuous saline from two s.c. 2ML2 osmotic pumps. Perioperative penicillin (100,000 u/kg, i.m.) was given to all rats before implantation of the minipumps. Survival was recorded in each group. Three rats treated for established tumors and two control rats were sacrificed 7 days after initiation of NaPA (14 days after tumor inoculation). These were used for electron microscopic studies of treated tumors, in vivo proliferation assays, and measurement of NaPA levels in the serum and CSF. Peripheral organs (heart, lung, spleen, liver, kidney, bowel, adrenal, and gonads) were harvested and subjected for a routine histological examination. Brain specimens were sectioned and stained for routine hematoxylin and eosin (H&E) and myelin stains (Luxol-fast blue) for evidence of drug-related toxicity.

Electron microscopy. Animals were sacrificed by intracardiac perfusion with 1% paraformaldehyde and 2.5% gluteraldehyde in 0.1M sodium cacodylate buffer at pH 7.4. Two hours later the fixed brains were washed in buffer and sliced into 1 mm thick coronal sections. The areas containing tumors were further dissected into 1 mm$^3$ cubes, post-fixed with 2% osmium tetroxide in 0.1M sodium cacodylate buffer for 2 hours, washed in buffer, mordanted en block with 1% uranyl acetate at pH 5 overnight, then washed, dehydrated and embedded in Epon. Thin sections were cut at several levels into each block to ensure greater sampling. Electron micrographs of tumor cells were taken at random for morphology.

In vivo proliferation assay. One NaPA-treated and one saline-treated rat received an i.p. injection of 9 mg/3 ml of BrdU (Amersham, Ill.) 14 days after tumor inoculation and 7 days after initiation of treatment. Two hours later the rats were sacrificed and the brains were removed and sectioned. Mouse anti-BrdU monoclonal antibodies were used for immunostaining of the tissues which were then counterstained with hematoxylin. Tumor cells in 10 high-power fields were enumerated in each tumor specimen and the percent of positively staining cells (indicating incorporation of BrdU during active cell division) was recorded.

Measurement of NaPA levels in serum and CSF. Three NaPA-treated and 2 saline-treated rats were sacrificed after 7 days of combined s.c. and i.p. NaPA or saline administration. Blood was drawn from the heart and CSF was aspirated from the cisterna magna. Due to volume limitations of CSF, pooled serum and CSF samples were assessed in a similar fashion. Protein extraction of a 200 μl aliquot of biological fluid was carried out with 100 μl of a 10% perchloric acid solution. 150 μl of supernate was neutralized with 25 μl of 20% potassium bicarbonate and centrifuged. 125 μl of supernate was then pipetted into sampling tubes. Chromatography was performed on a Gilson 715 HPLC system using a 30 cm Waters C18 column (i.d. 3.9 mm) at 60° C.. A 75 μl injectate was eluted with an acetonitrile/water gradient ranging from 5 to 30% over 20 minutes and flowing at 1 ml/min. UV-monitoring was performed at a wavelength of 20 nm. Elution time for phenylacetate was 14.8 minutes.

Statistical analysis. The Chi-square test was used to compare proportions of BrdU-positive cells. The Mantel-Haenzel test was used to compare survival between NaPA-treated and saline-treated rats in the survival experiments.

In Vitro Results

Figure 8:
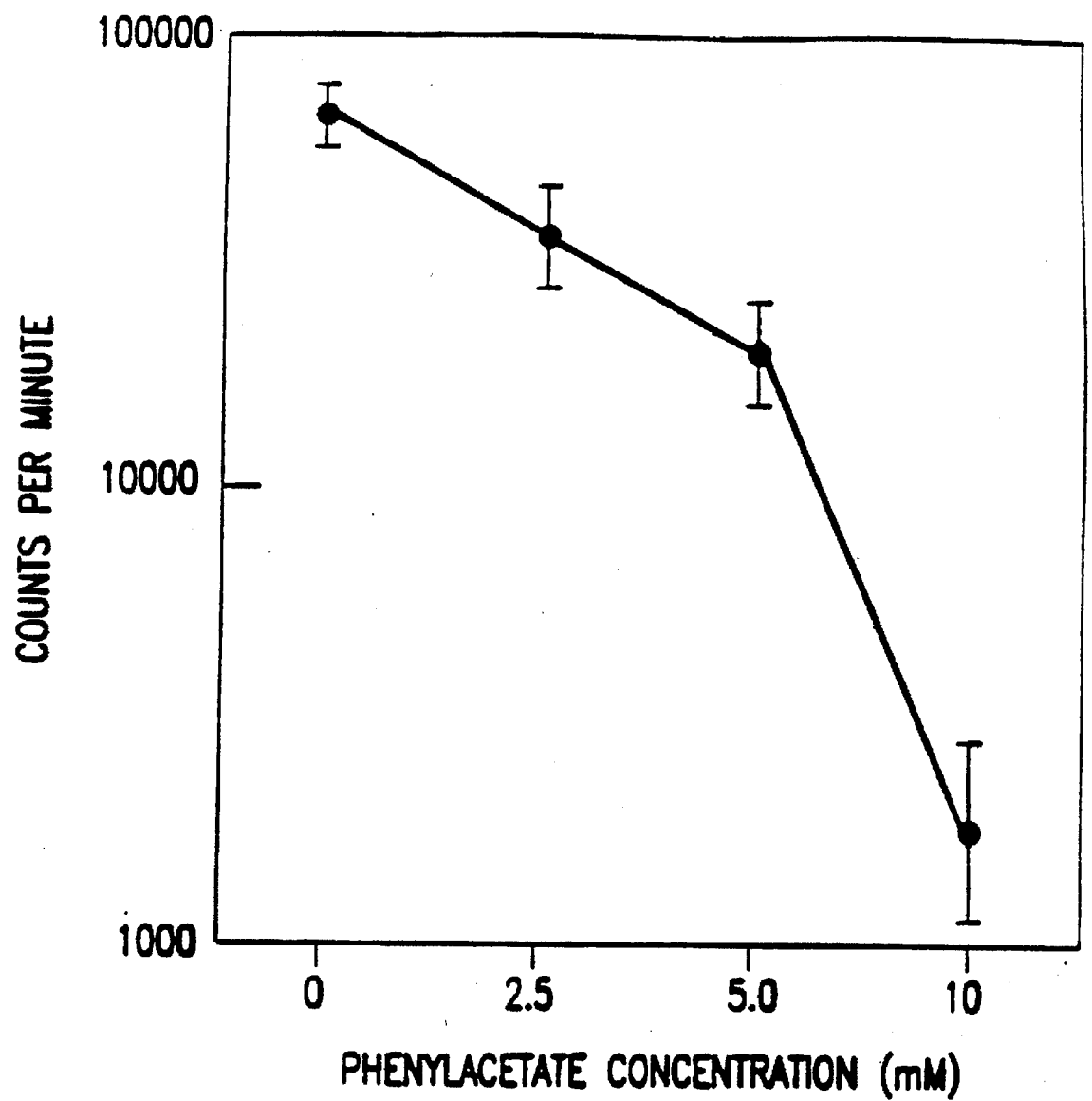
FIG. 8 shows the effects of phenylacetate on rate of proliferation after in vitro exposure of 9L tumor cells to various concentrations of phenylacetate for 5 days. Significant decline in DNA-synthesis was observed. Data are expressed as means±S.D. counts per minute (cpm).

In vitro Effect of NaPA on cell proliferation and anchorage dependency. Treatment of 9L cells with NaPA for 5 days resulted in dose-dependent decrease in cell number with $IC_{50}$ at 6.0±0.5 mM. This was accompanied with a decrease in tritiated-thymidine incorporation (FIG. 8). In addition, phenylacetate induced a dose-dependent restoration of anchorage dependency, indicating a reversion of the malignant phenotype (Table 19). 9L cells that were exposed to NaPA for 7 days before plating in agar (not containing NaPA) still showed >40% inhibition in colony formation (Table 19).

TABLE 19

Phenylacetate Inhibits
Anchorage-Independent Growth of 9L Gliosarcoma Cells

| Treatment in Culture | PA in Agar (mM) | Colony Formation | |
|---|---|---|---|
| | | # Colonies | % Inhibition |
| none | 0 | 628 ± 50 | — |
| none | 5 | 8 ± 4 | 98.7 |
| | 2.5 | 111 ± 13 | 82.4 |
| | 1.25 | 326 ± 20 | 48.0 |
| *Phenylacetate | 0 | 375 ± 25 | 40.3 |

*9L cells were treated with 5 mM phenylacetate in culture for 7 days before being plated on soft agar.

In Vivo Studies

In vivo proliferation assay and electron microscopy findings. Treatment of established brain tumors with NaPA resulted in a significant decrease in the rate of proliferation. 285 of 1283 treated tumor cells stained for BrdU compared to 429 of 1347 saline-treated tumor cells (mitotic index of 0.22 in NaPA-treated vs. 0.33 in saline-treated tumors7 p<0.0001).

Electron microscopy of these tumors showed a striking abundance of well-organized rough endoplasmic reticulum in the NaPA-treated tumor cells, indicating a higher degree of cell differentiation [Ghadially F N. Endoplasmic reticulum and ribosomes in cell differentiation and neoplasia. In: eds. *Ultrastructural Pathology of the Cell and Matrix*. Third, London:Buttorworths; 1992:450–454]. By contrast, untreated tumors generally had scant rough endoplasmic reticulum and numerous polyribosomes, which are characteristics of highly malignant cells.

In addition, mitotic cells were more frequently found in untreated tumors.

Serum and CSF levels of NaPA. Assays of pooled serum and CSF from 3 treated and 2 control rats, obtained after 7 days of combined s.c. and i.p. NaPA (total daily dose of 850 mg/kg) or saline administration, revealed a mean phenylacetate level of 2.45 mM in the serum and 3.1 mM in the CSF. No phenylacetate was detected in the serum of CSF samples from saline-treated rats.

Survival Experiments

Figure 9:
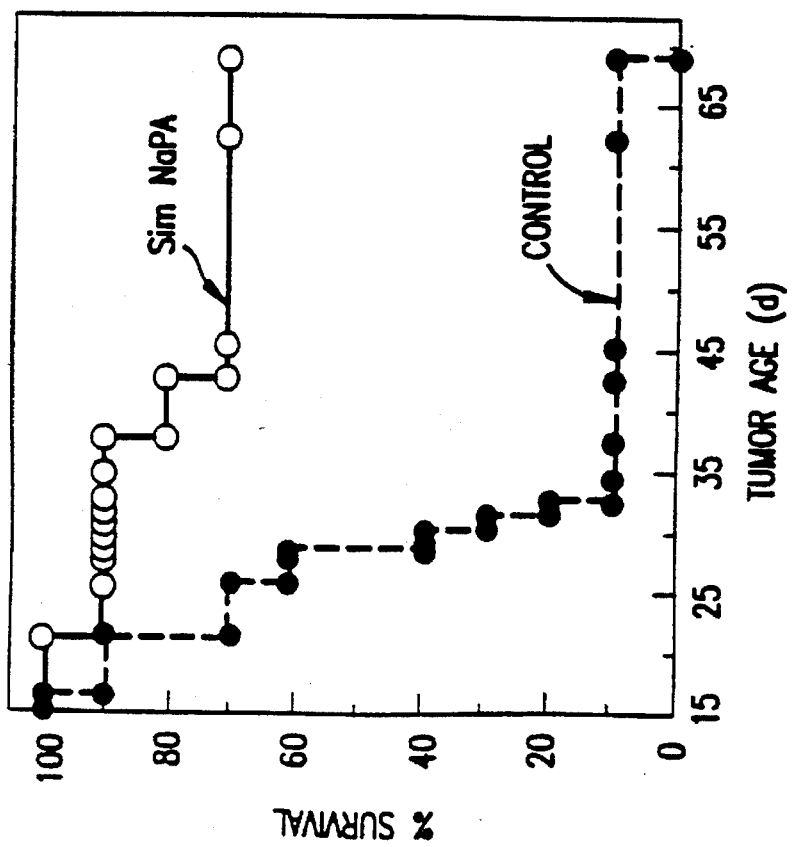
FIG. 9 shows the treatment with phenylacetate from the day of intracerebral tumor inoculation extended survival compared with treatment with saline (p<0.01; Mantel-Haenzel test).

Simultaneous tumor inoculation and administration of NaPA. Seven of 10 NaPA-treated rats survived for >90 days after tumor inoculation when NaPA was administered for 4 weeks starting on the day of tumor inoculation. Nine of 10 control rats died within 34 days after tumor inoculation (p<0.01, Mantel-Haenzel test) (FIG. 9).

Figure 10:
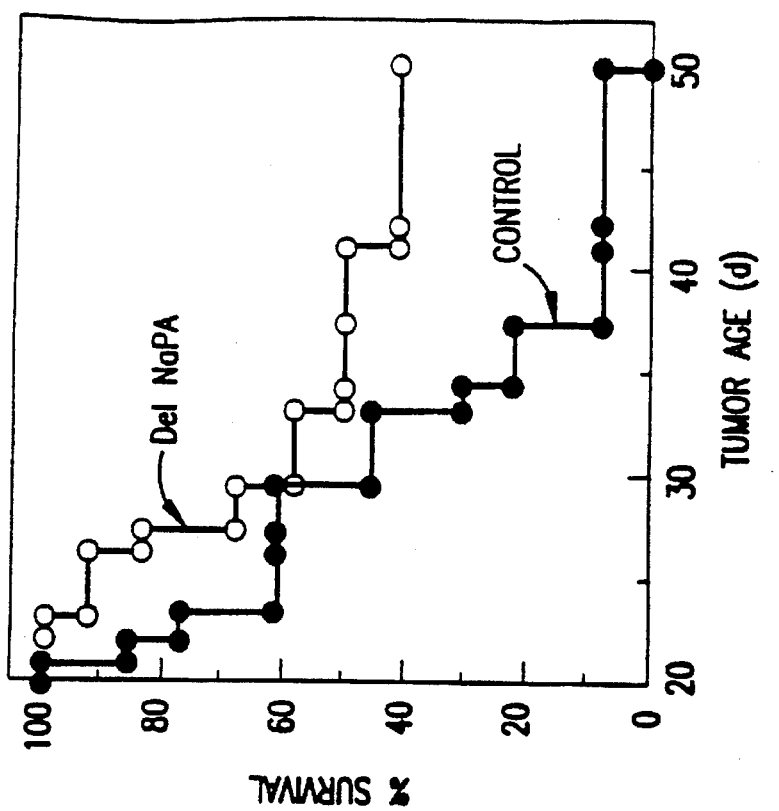
FIG. 10 shows the treatment of established tumors with phenylacetate extended survival compared to treatment with saline (p<0.03; Mantel-Haenzel test).

Treatment of established tumors with NaPA. Five of 12 rats treated with s.c. and j.p. NaPA for 4 weeks (starting 7 days after tumor inoculation) are still alive 50 days after tumor inoculation, while 12 of 13 saline-treated rats died by day 36 (p<0.03 Mantel-Haenzel test) (FIG. 10).

Toxicity. No adverse effects of NaPA treatment were detected in any treated rats. Histological evaluation of the major peripheral organs and non-tumoral brain showed no abnormalities.

Discussion. Phenylacetate induced a potent cytostatic and antitumor effect in the in vitro and in vivo brain tumor models used in these studies. This effect extended beyond the duration of drug administration, indicated by the long-term survival and apparent cure of rats which received NaPA either simultaneously with tumor inoculation or after tumors were established. This extended effect of NaPA shows that the malignant phenotype of treated tumor cells reverted, perhaps irreversibly in some animals, to one that was more benign and differentiated. Anchorage independence, i.e., the ability of cells to form colonies in semi-solid agar, is characteristic of malignant glioma cells. Phenylacetate caused a dose-dependent restoration of anchorage dependency, indicating reversion of the glioma cells to a non-malignant phenotype. More than 80% inhibition of colony formation was achieved at NaPA concentration in the agar plate of 2.5 mM, similar to the serum and CSF levels measured in treated rats. In addition, after one week of exposure to NaPA, more than 40% of tumor cells maintained a benign growth pattern despite the absence of NaPA in the agar plates (Table 19). A significant in vivo indicator of cell differentiation was observed in our study in the subcellular organelles of treated brain-tumor cells. The disorganized cytoplasmic polyribosomes in the saline-treated tumor cells were transformed by NaPA to a hyperplastic, well organized, rough endoplasmic reticulum. The endoplasmic reticulum is a highly specialized structure that performs many distinct functions. Hence a well-developed endoplasmic reticulum represents cell differentiation and functional activity. An inverse relationship has been noted between the amount of rough endoplasmic reticulum and the growth rate and degree of malignancy of tumors [Ghadially F N. Diagnostic Electron Microscopy of Tumours. eds. 2. London:Butterworth; 1985]. The numerous polyribosomes in the untreated tumor cells correlated well with the number of mitoses seen by light microscopy and were confirmed by the BrdU proliferation assay. These changes underscore the differentiating effect of NaPA on the malignant glial cells and correlate with the in vivo decrease in cell proliferation and extended survival that occurred in treated animals with brain tumors.

Therapeutic blood and CSF NaPA levels were reached in the treated rats. The high CSF levels indicate good penetration of NaPA into the central nervous system and into the developing tumor. The doses used are well below the known toxic levels of NaPA in children with inborn errors of urea synthesis (2.5 g/kg/d) or rats (1.6 g/kg/d) and indicate that NaPA can be given safely at a higher doses, possibly with enhancement of antitumor efficacy. These data indicate that phenylacetate, given to rats at a non-toxic dose, has a profound effect on tumor growth regulation and cell maturation.

Example 9:

Suppression of 5-Aza-2'-deoxycytidine induced carcinogenesis

Differentiation inducers selected for their low cytotoxic and genotoxic potential could be of major value in chemoprevention and maintenance therapy. Specifically, the ability of phenylacetate to prevent carcinogenesis by the chemotherapeutic hypomethylating drug, 5-aza-2'-deoxycytidine (5AzadC), was tested in vitro and in mice. Transient exposure of immortalized, but non-tumorigenic ras-transformed 4C8 fibroblasts to 5AzadC resulted in neoplastic transformation manifested by loss of contact inhibition of growth, acquired invasiveness, and tumorigenicity in athymic mice. The latter was associated with increased ras expression and a decline in collagen biosynthesis. These profound phenotypic and molecular changes were prevented by a simultaneous treatment with phenylacetate. Protection from 5AzadC carcinogenesis by phenylacetate was: (a) highly efficient despite DNA hypomethylation by both drugs; (b) free of cytotoxic and genotoxic effects; (c) stable after treatment was discontinued, and; (d) reproducible in vivo. Whereas athymic mice bearing 4C8 cells developed fibrosarcomas following a single i.p. injection with 5AzadC, tumor development was significantly inhibited by systemic treatment with nontoxic doses of phenylacetate. Phenylacetate and its precursor suitable for oral administration, phenylbutyrate, may thus represent a new class of chemopreventive agents, the efficacy and safety of which should be further evaluated.

The multi-step nature of neoplastic transformation makes this disease process amendable to chemopreventive intervention. Several agents have been shown to inhibit carcinogenesis and thereby prevent the development of primary or secondary cancers [Kelloff, G. J., C. W. Boone, W. F., Malone, and V. E. Steele. 1992. Chemoprevention clinical trials. *Mutation Res.*, 267: 291–295; Weinstein, B. I. 1991. Cancer prevention: Recent progress and future opportunities. *Cancer Res.*, 51:5080s–5085s; Wattenberg, L. W. Inhibition of carcinogenesis by naturally occurring and synthetic compounds. In: Y. Kuroda, D. M. Shankel and M. D. Waters (eds), Antimutagenesis and Anticarcinogenesis, Mechanisms II, pp. 155–166. New York: Plenum Publishing Corp., 1990; Sporn, M. B., and D. L. Newton. 1979. Chemoprevention of cancer and retinoids. *Fed. Proc.* 38:2528–2534]. Of major interest are natural products and their analogs, including vitamins (A, B12, C, D3, and E), retinoids, and terpenes. These agents can suppress neoplastic transformation subsequent to a carcinogenic insult by regulating cell growth and differentiation. One such growth regulator is phenylacetate.

The efficacy of phenylacetate as a chemopreventive agent was tested using in vitro and in vivo models of 5AzadC-induced carcinogenesis. Despite the promise of 5AzadC in the treatment of cancer and of beta-chain hemoglobinopathies, its clinical applications have been hindered by concerns regarding carcinogenic potential. The model used in the present studies involved premalignant murine fibroblasts (cell lines 4C8 and PR4), which express a transcriptionally activated c-Ha-ras protooncogene. These non-tumorigenic cells are highly susceptible to malignant conversion by pharmacological doses of 5AzadC. However, Phenylacetate can protect such vulnerable cells from 5AzadC-induced carcinogenesis both in culture and in mice.

Cell Cultures and Reagents. The subclones of mouse NIH 3T3 fibroblasts, PR4N and 4C8-A10 (designated here PR4 and 4C8) have been previously described [Wilson, V. L., R. A. Smith, H. Autrup, H. Krokan, D. E. Musci, N- N- T. Le, J. Longoria, D. Ziska, and C. C. Harris. 1986. Genomic 5-methylcytosine determination by ]$^{32}$P-postlabeling analysis. *Anal. Biochem.*, 152:275–284; Dugaiczyk, A., J. J. Haron, E. M. Ston, O. E. Dennison, K. N. Rothblum, and R. J. Schwartz. 1983. Cloning and sequencing of a deoxyribonucleic acid copy of glyceraldehyde-3-phosphate dehydrogenase messenger ribonucleic acid isolated from chicken muscle. *Biochem.* 22:1605–1613]. Both cell lines are phenotypic revertants isolated from LTR/c-Ha-ras1-transformed 3T3 cells after long-term treatment with murine interferon $\alpha/\beta$. Cultures were maintained in Dulbecco's modified Eagle's medium (DMEM) supplemented with 10% heat inactivated fetal calf serum (Gibco) and antibiotics. The sodium salts of phenylacetic and phenylbutyric acids (Elan Pharmaceutical Corporation) were dissolved in distilled water. 5AzadC (Sigma St. Louis Mo.) was dissolved in phosphate buffered saline (PBS) and stored in aliquots at $-20°$ C. until use. Exposure of 5AzadC to direct light was avoided at all times to prevent drug hydrolysis.

Treatments with 5AzadC. For treatment in culture, cells were plated at $1-2\times10^5$ cells in 100 mm dishes and the drugs added to the growth medium at 20 and 48 hrs later. The cells were subsequently subcultured in the absence of the nucleoside analogs and observed for phenotypic alterations. For in vivo treatment with 5AzadC, 6–9 week-old female athymic nude mice (Division of Cancer Treatment, NCI Animal Program, Frederick Cancer Research Facility) were inoculated subcutaneously (s.c.) with $0.5\times10^6$ cells. Twenty four hours later 400 µg of freshly prepared 5AzadC in 200 µl of PBS was administered intraperitoneally (j.p.) into each animal (approximately 20 mg/kg). Systemic treatment with NaPA is described in the text.

Growth on Matrigel. The ability of cells to degrade and cross tissue barriers was assessed by a qualitative in vitro invasion assay that utilize matrigel, a reconstituted basement membrane (Collaborative Research). Cells were exposed for 48 hrs in T.C. plastic dishes with 5AzadC alone or in combination with NaPA. NaPA treatment continued for additional 1–2 weeks. Cells were then replated (at $5\times10^4$ per point) onto 16 mm dishes (Costar, Cambridge, Mass.), which were previously coated with 250 µl of matrigel (10 mg/ml). NaPA was either added to the dishes or omitted in order to determine the reversibility of effect. Net-like formation characteristic of invasive cells occurred within 12 hours; invasion into the matrigel was evident after 6–9 days.

Tumor Formation in Athymic Mice. Cells were injected s.c. ($5\times10^5$ cells per site) into 4–6 week old female athymic nude mice (Division of Cancer Treatment, NCI animal Program, Frederick Cancer Research Facility). The number, size, and weight of tumors were recorded after 3–4 weeks.

For histological examination, tumors were excised, fixed in Bouin's solution (picric acid: 37% formaldehyde: glacial acetic acid, 15:5:1 vol/vol), and stained with H&E.

Measurement of DNA Methylation. To determine the 5-methylcytosine content, samples of cultures were taken 24 hours after the second 5AzadC treatment. The cell pellets were lysed in 0.5% SDS, 0.1M NaCl, 10 mM EDTA pH 8.0, added with 400 μg/ml of proteinase K (Boehringer Mannheim), and stored at −70° C. until DNA isolation and analysis. The content of methylated/unmethylated cytosine residues in the cellular DNA was measured by a $^{32}$P-postlabeling technique as previously described.

Northern Blot Analysis and DNA Probes. Cytoplasmic RNA was extracted from exponentially growing cells and separated by electrophoresis in 1.2% agarose-formaldehyde gels. RNA preparation, blotting onto nylon membranes (Schleicher and Schuell), hybridization with radiolabeled DNA probes, and autoradiography were performed as described [Rimoldi, D., V. Srikantan, V. L. Wilson, R. H. Bassin, and D. Samid. 1991. Increased sensitivity of non-tumorigenic fibroblasts expressing ras or myc oncogenes to malignant transformation induced by 5-aza-2'-deoxycytidine. *Cancer Res.*, 51:324–330]. The DNA probes included: 6.2 kb EcoRI fragment of v-Ki-ras1, 2.9kb SacI fragment of the human c-Ha-ras1 gene, and a BamHI 4.5 kb fragment of the c-myc gene. Glyceraldehyde phosphate dehydrogenase cDNA [Dugaiczyk, A., J. J. Haron, E. M. Ston, O. E. Dennison, K. N. Rothblum, and R. J. Schwartz. 1983. Cloning and sequencing of a deoxyribonucleic acid copy of glyceraldehyde-3-phosphate dehydrogenase messenger ribonucleic acid isolated from chicken muscle. *Biochem.* 22:1605–1613] was provided by M. A. Tainsky (University of Texas, Houston), and a mouse transin cDNA by G. T. Bowden (University of Arizona, Tucson). The cDNA probe for mouse histocompatibility class I antigens was a gift from G. Jay (NIH, Bethesda). Radiolabeled probes were prepared with [$^{32}$P]dCTP (NEN) using a random primed DNA labeling kit (Boehringer Mannheim, Germany).

In Vitro Carcinogenesis Induced by 5AzadC and Its Prevention by Phenylacetate. Untreated 4C8 and PR4 formed contact-inhibited monolayers composed of epithelial-like cells. In agreement with previous observations, transient exposure of these cultures to 0.1 uM 5AzadC during logarithmic phase of growth resulted in rapid and massive neoplastic transformation. Within one week of 5AzadC treatment, the great majority of the cell population became refractile and spindly in shape, and formed multilayered cultures with increased saturation densities (Table 7), indicative of loss of contact inhibition of growth. These phenotypic changes could be prevented by the addition of 5–10 mM NaPA (Table 7). Several different regimens of NaPA treatment were found to be similarly effective. These included: (a) pre-treatment with NaPA, starting one day prior to the addition of 5AzadC; (b) simultaneous exposure to both drugs, and; (c) addition of NaPA one day after 5AzadC. In all cases, cells were subsequently subjected to continuous treatment with NaPA for at least one week. Cells cultured under these conditions, like those treated with NaPA alone, formed contact-inhibited monolayers resembling untreated controls. These cells maintained the benign growth pattern for at least three weeks after NaPA treatment was discontinued.

That NaPA prevents neoplastic transformation was further indicated by the inability of cells to invade reconstituted basement membranes (matrigel), and form tumors in athymic mice. When plated onto matrigel, 5AzadC-transformed 4C8 and PR4 cells developed net-like structures characteristic of highly malignant cells, and eventually degraded the extracellular matrix components. In marked contrast, NaPA-treated cultures formed small, non-invasive colonies on top of the matrigel, as previously observed with normal fibroblasts. Untreated parental cells exhibited an intermediate phenotype, as their colonies were slow growing and non-invasive, yet irregular in shape possibly due to increased cell motility. The chemopreventive effect of phenylacetate could be mimicked by its precursor, phenylbutyrate. Cells exposed to 5AzadC in the presence of sodium phenylbutyrate (NaPB, 1.5–3 mM) maintained contact inhibited growth and exhibited a benign phenotype when placed onto matrigel (Table 7).

TABLE 7

Effect of 5AzadC and NaPA on DNA Methylation

| Cells | Treatment[a] | DNA Methylation | |
|---|---|---|---|
| | | % 5mC[b] | % of Control |
| 4C8 | none | 3.49 ± 0.06 | 100 |
| | 5AzadC | 1.52 ± 0.27 | 43 |
| | NaPA | 2.22 ± 0.10 | 63 |
| | 5AzadC + NaPA | 1.62 ± 0.18 | 46 |
| PR4 | none | 2.72 ± 0.16 | 100 |
| | 5AzadC | 1.11 ± 0.22 | 41 |
| | NaPA | 1.25 ± 0.08 | 46 |
| | 5AzadC + NapA | 1.06 ± 0.11 | 39 |

[a]Cells were treated with 0.1 uM 5AzadC and/or 10 mM NaPA and the percentage of 5mC was determined as described in "Materials and Methods".
[b]Data indicate the mean ± S.D. (n = 4) of two experiments.

The in vitro growth characteristics of cells correlated with their behavior in athymic mice. 5AzadC-treated 4C8 cells developed rapidly growing fibrosarcomas within 2 weeks of s.c. transplantation into mice. Consistent with their behavior in vitro, the parental cells were far less aggressive, forming small lesions after 3–4 weeks in three of eight recipient animals. However, no tumors developed in animals injected with 4C8 cells that had been pre-treated for one week in culture with the combination of 5AzadC and NaPA (Table 7). There was also no tumor formation in mice injected with 4C8 treated with NaPA alone. Therefore it follows that NaPA induced phenotypic reversion of the premalignant fibroblasts and prevented their malignant conversion by the cytosine analog.

Modulation of Gene Expression by NaPA. The NIH 3T3-derived cells lines, 4C8 and PR4, carry an LTR-activated c-Ha-ras protooncogene. Northern blot analysis of 5AzadC-treated 4C8 revealed a significant increase in ras mRNA levels and a decline in the differentiation marker, collagen α (type I) transcripts. No such changes in gene expression occurred in cultures to which NaPA was added. Withdrawal of NaPA after one week of continuous treatment did not cause restoration of ras expression, confirming that the therapeutic benefit of NaPA is stable in the absence of further treatment.

Effect of Phenylacetate and 5AzadC on DNA methylation. 5AzadC is a potent inhibitor of DNA methylation, an epigenetic mechanism implicated in the control of gene expression and cell phenotype. Hypomethylation may underlay the therapeutic effect of 5AzadC in cancer and in severe inborn anemias [Momparler, R. L., G. E. Rivard, and M. Gyger. 1985. Clinical trial on 5-aza-2'-deoxycytidine in patients with acute leukemia. *Pharmac. Ther.*, 30:277–286; Stamatoyannopoulos, J. A., and A. W. Nienhuis. 1992.

Therapeutic approaches to hemoglobin switching in treatment of hemoglobinopathies. *Annu. Rev. Med.*, 43:497–521; Ley, T. J., J. DeSimone, N. P. Anagnou, G. H. Keller, R. K. Humphries, P. H. Turner, P. H., N. S. Young, P. Heller, and A. W. Nienhuis. 1982. 5-Azacytidine selectively increases gamma-globin synthesis in a patient with beta+ thalassemia. *N. Engl. J. Med.* 307:1469–1475]. However, changes in DNA methylation could also be responsible for its carcinogenic potential. It was of interest therefore to determine the degree of DNA methylation in cells protected by phenylacetate. As would be expected, 5AzadC caused a significant decrease in the content of 5-methylcytosine (5mC) (Table 6). There was, however, a comparable decline in 5mC in cells treated with 5AzadC in combination with NaPA, as well as in those treated with NaPA alone (Table 6).

TABLE 6

In vitro Prevention by
Phenylacetate of 5AzadC-Induced Carcinogenesis

| Cell Treatment | Saturation | | Tumorigenicity in Mice[c] | |
| --- | --- | --- | --- | --- |
| | Density[a] (cells/cm² × 10⁻⁵) | Invasiveness[b] | Incidence | Tumor Size (mm) |
| None | 3.9 | – | 3/8 | 1.0 (0.5–2) |
| 5AzadC | 7.0 | + | 8/8 | 11.5 (4–19) |
| 5 AzadC + NaPA | 1.6 | – | 0/8 | 0 |
| 5 AzadC + NaPB | 1.1 | – | ND | |
| NaPA | ND | – | 0/8 | 0 |
| NaPB | 1.3 | – | ND | |

[a]Cell were treated simultaneously with the indicated drugs and kept in culture for 5 days post confluency at which time they were detached and counted. Exposure to 5AzadC was transient as described in Materials and Methods, while treatment with NaPA and NaPB continued throughout the experiment. Similar results were obtained when NaPA treatment was initiated one day prior or after cell exposure to 5AzadC (data not shown).
[b]Cells were plated on top of a matrigel layer and observed for malignant growth pattern, i.e., development of characteristic processes and degradation of the reconstituted basement membrane and invasion towards the plastic surface below.
[c]Cells pretreated in culture were injectd s.c (5 × 10⁵ cells per site) into 2 month old female athymic nude mice. Results determined after 3 weeks indicate tumor incidence (tumor bearing, injected animals) and size. The values of tumor size are mean (range).
ND = not determined.

In Vivo Chemoprevention by NaPA. To determine the efficacy of NaPA in vivo, studies were extended to include an animal model involving athymic mice bearing the non-tumorigenic 4C8 cells transplanted subcutaneously. A single i.p. injection of mice with 5AzadC (20 mg/kg) resulted in tumor development at the site of 4C8 cell inoculation. However, when mice were pre-treated with NaPA 1.5 hr prior to 5AzadC injection, and NaPA treatment continued for 22 days thereafter, the incidence of tumor formation was significantly decreased (Table 8). There were no adverse effects associated with NaPA treatment as indicated by animal weight and behavior. Further more, despite causing DNA hypomethylation NaPA did not induce neoplastic transformation of transplanted 4C8 cells. Animals protected by NaPA either failed to develop tumors or formed slow-growing lesions at the site of 4C8 inoculation. The animal data is consistent with the in vitro findings, indicating that NaPA can prevent 5AzadC-induced neoplastic transformation without producing significant toxicities.

TABLE 8

In vivo Chemoprevention
by Phenylacetate

| Group | Animal Treatment[a] | Tumor Incidence[b] positive/total | Tumor Size[c] mean (range) |
| --- | --- | --- | --- |
| A | PBS | 0/4 | 0 |
| B | NaPA | 0/4 | 0 |
| C | 5AzadC + PBS | 9/9 | 12 (2–29) |
| D | 5AzadC + NaPA | 4/10 | 3 (0–10) |

[a]4C8 cells (5 × 10⁵ per site) were transplanted s.c. into athymic mice. The next day, the animals in were treated i.p. with 400 mg/kg NaPA, and 1.5 hr later with 20 mg/kg 5AzadC. NaPA treatment was repeated at 4.5 hours following 5AzadC injection. Subsequent treatments involved NaPA injections twice daily for 8 days, and once a day for additional 2 weeks. PBS was used as a control.
[b]Data indicates tumor growth at 4 weeks after 5AzadC treatment. Spontaneous tumors developed thereafter in control animals receiving PBS, and subsequently in those treated with NaPA.
[c]Tumor diameter in millimeters.

There is considerable interest in the use of nontoxic differentiation inducers in cancer chemoprevention. Drug toxicity is particularly important considering the overall health condition and variable life-span of candidate populations, i.e., high-risk individuals and patients in remission. The differentiation inducer phenylacetate can prevent 5AzadC-induced carcinogenesis both in vitro and in vivo when used at nontoxic doses.

Chemoprevention can be accomplished by either blocking the "initiation" step of carcinogenesis (i.e., mutagenesis), or by suppressing "promotion" and progression to malignancy. The current studies, using premalignant cells with an activated ras oncogene as a model, examined the efficacy of phenylacetate as an anti-promotional drug. Other well characterized chemopreventive agents that block promotion include vitamin A and its synthetic retinoids; like phenylacetate, these compounds are also regulators of cell growth and differentiation.

The current studies exploited in vitro and in vivo models involving fibroblasts (designated 4C8 and PR4) that are highly vulnerable to malignant conversion by the DNA hypomethylating agents 5AzadC and 5AzaC (16,17). Transient exposure of these cells to 5AzadC, either in culture or in recipient athymic mice, caused rapid neoplastic transformation. Malignant conversion was associated with an increase in ras mRNA levels and down-regulation of collagen type I expression, indicating loss of cell differentiation. These profound biological and molecular changes brought about by 5AzadC are prevented by a simultaneous treatment with non-cytotoxic concentrations of phenylacetate and its precursor, phenylbutyrate. Phenylacetate's anti-tumor activity and lack of toxicity were confirmed in athymic mice. In the in vivo model, mice bearing the susceptible 4C8 cells transplanted s.c. were injected i.p. with 5AzadC. All mice so treated developed rapidly growing fibrosarcomas; however, the incidence of tumor formation was markedly reduced by systemic treatment with NaPA.

The mechanism by which NaPA prevented the 5AzadC induced malignant conversion is unclear. Like other chemopreventive agents that block promotion, phenylacetate may act by inducing cytostasis and tumor maturation. There is a growing body of evidence indicating that phenylacetate can cause selective growth arrest and tumor differentiation in vitro and in rodent models. In some cases, e.g., promyelocytic leukemia, differentiation induced by phenylacetate was linked to a decline in myc oncogene expression. In NaPA-treated 4C8, protection from de-differentiation (evidenced by growth characteristics and collagen expression), was associated with inhibition of ras overexpression. Down-regulation of oncogene expression may thus be responsible in part for the chemopreventive activity of NaPA. In addition to affecting ras at the mRNA levels, phenylacetate, an inhibitor of the mevalonate pathway of cholesterol synthesis [Castillo, M., J. Iglesias, M. F. Zafra, and E. Garcia-Peregrin. 1991. Inhibition of chick brain cholesterolgenic enzymes by phenyl and phenolic derivatives of phenylalanine. Neurochem. Int., 18: 171–174], could also block the post-translational modification of the ras-encoded protein, p21. Limonene, an inhibitor of p21 prenylation, is a chemopreventive agent as well.

Phenylacetate blocked carcinogenesis by 5AzadC despite the decline in 5mC content. In fact, NaPA itself was found to inhibit DNA methylation; yet, in contrast to 5AzadC, NaPA was not carcinogenic. Correlations between carcinogenic potential and DNA hypomethylating activities of chemical agents have been previously documented in tissue culture models, and alterations in DNA 5mC patterns were proposed to contribute and enhance the initiation of carcinogenesis. However, the present data indicate that quantitative changes in DNA methylation alone are not sufficient to affect cell phenotype and thus, hypomethylating activity is not sufficient to induce the tumorigenic phenotype in these in vitro and animal models.

The selective induction of specific genes by intracellular factors and chemical agents subsequent to demethylation has been reported by several laboratories. For example, an increase in human gamma-globin gene expression in vitro was found to require activation by hexamethylenebisacetamide following treatment with 5AzaC [Ley J. T., Y. L. Chiang, D. Haidaris, N. P. Anagnou V. L. Wilson, and W. F. Anderson. 1984. DNA methylation and regulation of the human β-globin like genes in mouse erythroleukemia cells containing human chromosome 11. Proc. Natl. Acad. Sci. USA. 81:6618–6622]; demethylation of the gene by 5AzaC was not sufficient for gene expression. By contrast, phenylacetate and phenylbutyrate induced gamma-globin gene expression with subsequent accumulation of fetal hemoglobin in cultured erythroid progenitors and in humans. In addition to affecting DNA methylation, NaPA and NaPB also activate a nuclear receptor that functions as a transcriptional factor (the peroxisome proliferator receptor is discussed herein). Thus, one possible explanation for the differences in carcinogenic opposing activities between NaPA/NaPB and 5AzadC seen here may be the ability of the aromatic fatty acids to induce the expression of genes critical to growth control. Phenylacetate and related compounds can possibly reverse the methylation-mediated state of repression of silent anti-oncogenes. The finding of DNA hypomethylation by NaPA in mammalian cells does not come as a surprise in view of previous studies demonstrating that, at millimolar concentrations, phenylacetate inhibits DNA methylation in plant. Interestingly, at such high concentrations, phenylacetate also inhibits plant tumor cell proliferation. Therefore, the effect of phenylacetate on DNA methylation and its role in regulating growth and differentiation have been conserved in evolution.

The outcome of combining NaPA with 5AzadC (or 5AzaC) is of particular interest. The cytosine analogs have been shown to benefit patients with severe blood disorders such as leukemia, sickle cell anemia, and β-thalassemia. There is now experimental data suggesting that 5AzadC may be active also in some solid tumors, including malignant melanoma (Weber et al, submitted) and prostate carcinoma. Unfortunately, the clinical application of 5AzadC has been limited by concerns regarding carcinogenesis. The data indicate that NaPA can minimize the carcinogenic risk, while both preserving and potentiating the therapeutic effects of 5AzadC. Studies with human leukemic cells and with erythroid progenitors derived from patients with β-hemoglobinopathies revealed that NaPA can enhance the efficacy of 5AzadC, causing superinduction fetal hemoglobin production. Moreover, the addition of NaPA/NaPB to nontoxic, yet sub-optimal concentrations of 5AzadC, induced complete growth arrest and promoted apoptosis in cultured hormone-refractory prostatic carcinoma cells (unpublished data).

It appears therefore that phenylacetate, a common amino acid derivative, may be of value as an antitumor and chemopreventive agent. NaPA, which has an unpleasant odor, can be substituted by its precursor, NaPB (or a derivative or analog of NaPB), for oral administration. Upon ingestion by humans, phenylbutyrate undergoes β-oxidation to phenylacetate. Like NaPA, NaPB exhibits antitumor and chemopreventive activities in experimental models, and both drugs already proved safe for long-term oral treatment of children with urea cycle disorders. More recent clinical studies involving adults with cancer have confirmed that millimolar plasma levels of phenylacetate and phenylbutyrate can be achieved with no significant adverse effects. NaPB/NaPA will benefit high risk individuals predisposed to cancer development, be applied in combination with other anticancer therapeutics to enhance efficacy and minimize adverse effects, and perhaps be used in maintenance therapy to prevent disease relapse.

Example 10:

HbF induction in K562 cells by NaPA and derivatives

The K562 erythroleukemia line serves as a model for inherited anemias that are associated with a genetic defect in the beta globin gene leading to severe β-chain hemoglobinopathies.

The results reported in Table 9 also show that there is a synergistic affect when leukemia cells are exposed NaPA in combination with interferon alpha, a known biological response modifier or with the chemotherapeutic drug hydroxyurea (HU).

TABLE 9

Induction of Hemoglobulin Synthesis in Erythroleukemia K562 cells*

| TREATMENT | BENZIDINE | |
|---|---|---|
| | POSITIVE CELLS (%) | CELL VIABILITY (%) |
| Control | 1.8 | >95 |
| NaPA | | |
| 0.8 mg/ml | 6.0 | |
| 1.6 mg/ml | 17.1 | |
| Interferon 500 IU/ml | 13.5 | |
| HU 100 uM | 17.2 | |
| NaPA (0.8 mg/ml) + HU or IFN | 40–42 | |

*Results at seven days of treatment.

Analysis of gene transcripts showed accumulation of mRNA coding for gamma globin, the fetal form of globin. This was confirmed at the protein level.

Using the erythroleukemia K562 cell line described above it was found that 4-hydroxyphenylacetate was as effective as NaPA in inducing fetal hemoglobin accumulation, but was less inhibitory to cell proliferation. In contrast, some other analogs such as 2,4- or 3,5-dihydroxyphenylacetate were found to be highly toxic.

Example 11:

PC3 and DU145 cells—NaPA as an antitumor agent

The effectiveness of NaPA as an antitumor agent was further evaluated in a variety of experimental models. Studies in depth were performed with two androgen-independent human prostate adenocarcinoma cell lines, PC3 and DU145, established from bone and brain metastases, respectively, as well as hormone responsive LNCaP cultures. NaPA treatment of the prostatic cells resulted in concentration-dependent growth arrest, accompanied by cellular swelling and accumulation of lipid that stained positive with Oil-Red O. The results of this study are shown in FIG. 11. As illustrated therein, an $IC_{50}$ for NaPA occurred at 600–800 µg/ml. Significantly higher doses were needed to affect the growth of actively replicating normal human FS4 skin fibroblasts or normal endothelial cells ($IC_{50}$ from 12–15 µM), indicating a selective cytostatic effect of the drug.

Example 12:

PC3 cells—non-invasiveness after NaPA treatment

It is known that PC3 cells are invasive in vitro and metastatic in recipient athymic mice. [Albini, A. et al. A rapid in vitro assay for quantitating the invasive potential of tumor cells. Cancer Res. 47:3239–3245 (1987)]. The invasiveness of PC3 cells which is indicative of their malignant phenotype can be assessed by their ability to degrade and cross tissue barriers such as matrigel, a reconstituted basement membrane. Untreated PC3 cells and PC3 cells treated with NaPA for 4 days in culture were quantitatively analyzed in a modified Boyden chamber containing a matrigel-coated filter with FS4 conditioned medium as a chemoattractant. After 4 days of treatment with 800 µg/ml of NaPA in T.C. plastic dishes, $5 \times 10^4$ cells were replated onto 16 mm dishes (Costar, Cambdrige, Mass.) coated with 250 µl of matrigel 10 mg/ml. Controls showed the characteristic growth pattern of untreated cells, i.e, formation of net-like structures composed of actively replicating cells which eventually degraded the matrigel and formed monolayers on the plastic surface beneath. In contrast to the controls, the NaPA treated cells formed isolated small colonies which resembled normal human FS4 cells 8 days after plating. The NaPA treated cells failed to degrade the matrigel barrier. The formation of small noninvasive colonies on top of the matrigel is indicative of loss of malignant properties following treatment. Results of the in vitro invasion assays correlate highly with the biological behavior of cells in vivo.

Example 13:

PC3 cells—PAG treatment did not hinder invasiveness

PC3 cells treated with NaPA for one week in culture, in contrast to untreated cells or those treated with PAG, failed to form tumors when transplanted s.c. into athymic mice. These results are shown in Table 10.

TABLE 10

Tumorigenicity of Prostatic PC3 Cells in Nude Mice

| TREATMENT (mg/ml) | Incidence | Diameter (mm ± S.D.) | Weight (mg ± S.D.) |
|---|---|---|---|
| None | 7/7 | 9 ± 3 | 285 ± 60 |
| NaPA 0.8 | 1/7 | 2 | 50 |
| PAG 0.8 | 3/4 | 8 ± 2 | 245 ± 35 |

PC3 cells were pretreated for 1 week in culture and then injected ($2 \times 10^5$ cells/animal) s.c. into 4–5 week-old female athymic nude mice. The results in Table 10 indicate the incidence of tumor bearing animals/injected animals as well as tumor size measured as mean diameter±S.D. 8 weeks later.

Example 14:

Phenylacetate in combination with suramin

To further substantiate the phenotypic changes observed in the NaPA treated prostatic PC3 cells, Northern blot analysis revealed that NaPA inhibited the expression of collagenase type IV, one of the major metalloproteases implicated in degradation of basement membrane components, tumor cell invasion, and metastasis. Furthermore, it was found that NaPA treated prostatic PC3 cells showed an increase in the level of HLA-A mRNA which codes for major histocompatibility class I antigen known to affect tumor immunogenicity in vivo.

The malignant prostatic cell lines exhibit numerous abnormalities in gene expression, including increased production of autocrine tumor growth factor-β (TGF-β) and elevated activity of urokinase plasminogen activator (uPA). Members of the TGF-β family have been implicated in tumor growth control, anglogenesis, and immunosuppression. uPA, in contrast, is a serine protease involved in degradation of extracellular stroma and basal lamina structures, with the potential to facilitate tumor invasion and metastasis. It was of interest, therefore, to examine the effect of NaPA on TGF-β and uPa expression in the prostatic tumor cells. Northern blot analysis of PC3 after 72 h treatment revealed a decrease in TGF-β2 mRNA levels; the effect was specific for TGF-β2 as there was no change in the expression of TGF-β1. The decrease in TGF-β2 was accompanied by approximately a twofold increase in the levels of HLA-A3 mRNA, as previously observed in treated human leukemic HL-60 cells.

Preliminary analysis of uPA transcript levels showed no significant change after NaPA treatment. There was, however, a reduction cell-surface uPA activity. The hormone-refractory malignant PC3 and DU145 cells, but not the more indolent hormone-responsive LNCaP, displayed high cell-bound uPA activity. Because the parental PC3 cultures are composed of highly heterogenous cell populations with respect to uPA production, more homogeneous subclones were established by limiting dilutions and single-cell cloning. A subclone designated PC3-1, which resembled the parental PC3 cells in its invasive capacity and surface-localized uPA activity ($2.2 \pm 0.3 \times 10^{-6}$ Plau units per cell), was chosen for further studies. After 3 d of treatment of PC3-1 with NaPA 5 mM there was over 50% reduction in cell-associated uPA activity; the effect was dose-dependent and reversible upon cessation of treatment. Similar results were obtained with DU145 cells. Assay specificity was confirmed by the fact that pretreatment of cells with neutralizing anti-human uPA monoclonal antibodies, or addition of antibodies at the time of assay, blocked over 95% of the plasminogen-dependent proteolytic activity. Plasminogen-independent proteolysis constituted 30% of the maximal fibronectin degrading activity, and was similar for both NaPA-treated cells and untreated controls.

NaPA in Combination with Suramin

TABLE 11

Malignant Melanoma A375

| Treatment (μg/ml) | Growth (% of control) | Viability (%) |
|---|---|---|
| None | 100 | >95 |
| NaPA 400 | 63.3 | >95 |
| Suramin | | |
| 38 | 78.3 | >95 |
| 75 | 56.8 | >95 |
| 150 | 38.6 | 92 |
| 300 | 26.6 | 82 |
| NaPA (400) | | |
| + Suramin (38) | 45.5 | >95 |
| + Suramin (75) | 30.1 | 94 |
| + Suramin (150) | 21.8 | 92 |

TABLE 12

Prostate Adenocarcinoma PC3

| Treatment (μg/ml) | Growth (% of control) | Viability (%) |
|---|---|---|
| None | 100 | >95 |
| NaPA 800 | 59.6 | >95 |
| Suramin | | |
| 75 | 58.5 | nd |
| 150 | 46.5 | nd |
| 300 | 31.0 | nd |
| NaPA (800) | | |
| + Suramin (75) | 24.2 | 90 |
| + Suramin (150) | 10.9 | 64 |

NaPA was found to significantly potentiate the therapeutic effect of suramin, the only experimental drug known to be active against prostate cancer.

However, drug toxicities have been a major concern. In agreement with previous in vitro studies, we found that toxic doses of suramin (300μg/ml) were needed in order to achieve over 50% inhibition of prostatic DU145 cell growth. This cellular model was used to examine whether NaPA could enhance the activity of suboptimal but less toxic doses of suramin. Results of this examination show that NaPA and suramin act in an additive manner to inhibit DU145 cell proliferation. Moreover, suramin was found to be significantly more active if added to glutamine-depleted medium. Despite significant differences in tumor sensitivities, there was complete growth arrest when DU145 and PC3 cells were treated for 6 d with both NaPA and suramin in glutamine-depleted medium, under conditions in which each treatment alone had only a partial effect. Similarly, Tables 11 and 12 show the effect of combined NaPA and suramin treatment of malignant melanoma A375 cells and prostate adenocarcinoma PC3 cells.

It is known that a disease state characterized by the presence of benign hyperplastic lesions of the prostate exists as a separate disease entity and has been identified in many patients that progress to a diagnosis of prostatic cancer. Based on the above, it is anticipated that NaPA, in addition to being effective in the treatment of prostatic cancer, would be effective in treating patients having benign hyperplastic prostatic lesions.

Further experiments demonstrated that NaPA appears to have broad antitumor activity affecting a wide spectrum of malignancies. The experimental data presented in Table 13 indicate that NaPA 0.4–0.8 mg/ml caused about 50% inhibition of growth in treated adenocarcinoma of the prostate cell lines PC3 and DU145, melanoma A375 and SK MEL 28, lung adenocarcinoma H596 and H661, and astrocytoma U87, U373, and 343. Somewhat higher concentrations (1.0–1.5 mg/ml) were needed to cause a similar inhibition of squamous cell carcinoma A431, breast tumor MCS-7, osteosarcoma KRIB, and fibrosarcoma V7T. Typically, NaPA treatment was associated with growth arrest, induction of differentiation markers, reduced invasiveness in vitro, and loss of tumorigenicity in nude mice.

TABLE 13

Responses to Different Tumor Cell Lines to NaPA Treatment

| # | Tumor Cell Line | % Inhibition by NaPA 0.8 mg/ml[a] |
|---|---|---|
| 1 | Melanoma | |
|  | A375 | ≥70 |
|  | SK MEL 28 | >50 |
| 2 | Prostatic Ca[b] | |
|  | PC3 | ≥50 |
|  | DU145 | ≥50 |
|  | LaNCoP | >50 |
| 3 | Astrocytoma | |
|  | U87 | ≥50 |
|  | U343 | ≥50 |
|  | U373 | ≥50 |
| 4 | Kaposi's Sarcoma KS | ≤40 |
| 5 | Leukemia HL-60 | ≤40 |
| 6 | Leukemia K562 | ≤30 |
| 7 | Breast Cancer MCF-7 | ≤30 |
| 8 | Osteosarcoma | |
|  | KRIB | ≤30 |
|  | HOS | <20 |
| 9 | Fibrosarcoma | |
|  | V7T | ≤30 |
|  | RS485 | ≤30 |
| 10 | Squamous Cancer of Head & Neck A431 | <30 |

[a]Pharmacologically attainable concentration
[b]Carcinoma

Figure 15:
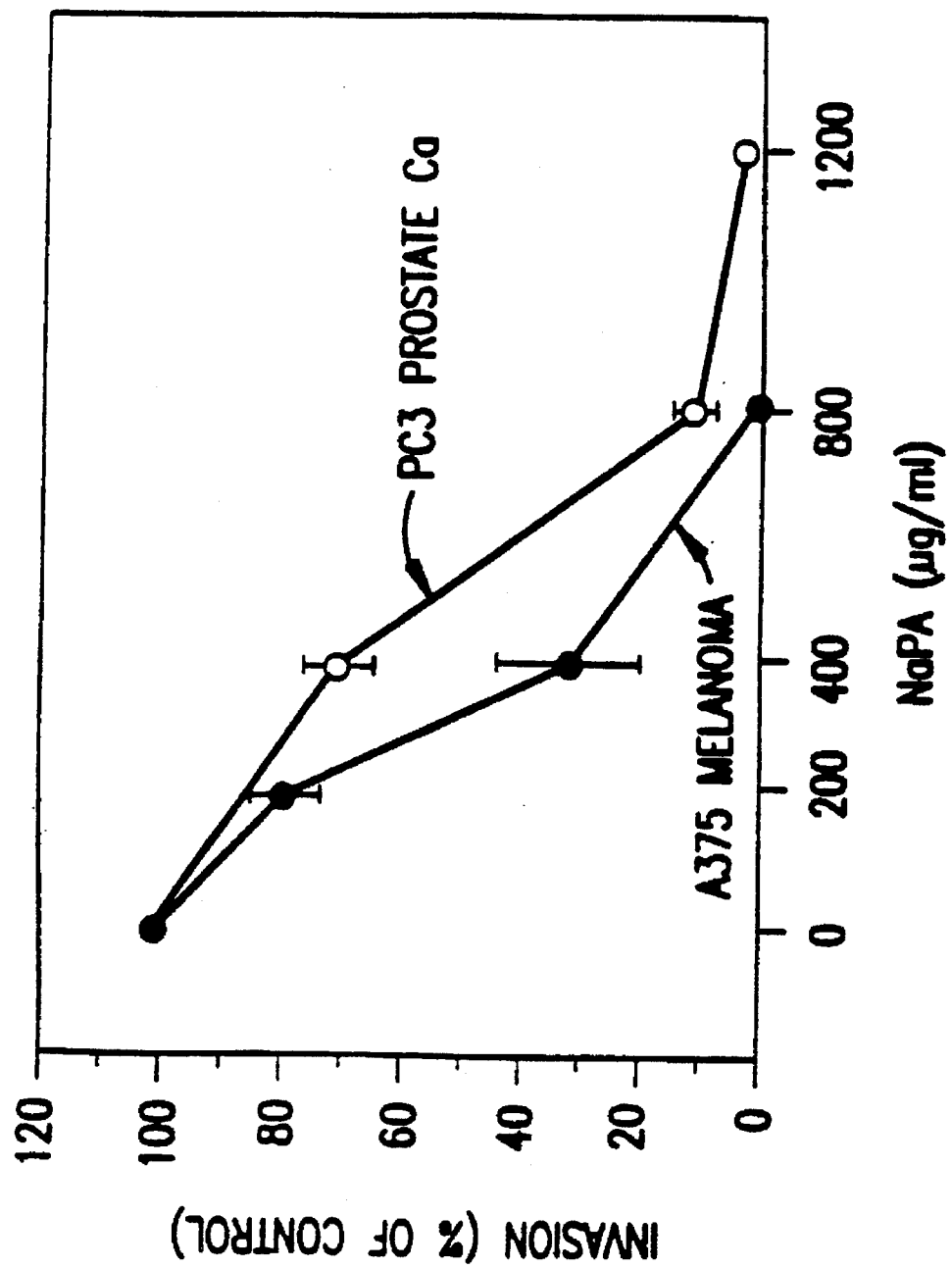
FIG. 15 shows the inhibition of tumor cell invasion by NaPA cells treated in culture for seven (7) days which were harvested and assayed for their invasive properties using a modified Boyden Chamber with a matrigel-coated filter. Results were scored six (6) to twenty-four (24) hours later.

Of major interest in Table 13 are the following:

1–3 Tumor cells show significant response i.e., ≥50% inhibition of proliferation within one week of treatment. Cf. FIG. 15.

4 KS, an HIV-associated disorder, may be more dramatically affected by NaPA in humans, due to inhibition of HIV expression and of essential growth factors released by infected lymphocytes.

5,6 The treated HL-60 promyelocytic leukemic cells undergo terminal differentiation, a desirable outcome of chemotherapy. In the K562 erythroleukemia, NaPA induced reversible erythroid differentiation with no significant growth arrest (<30%); thus the K562 data is of interest with respect to treatment of certain anemias, not cancer.

Less attractive:

7–10 For effective responses, the tumors may require much higher drug concentrations if used alone.

Although some of the malignant cell lines seem more sensitive than others, all were significantly more affected by NaPA when compared to normal or benign cells. For example, NaPA inhibited the growth of malignant osteosarcoma (KRIB) cells more so than benign osteosarcoma-derived HOS cells. A differential effect was seen also in ras-transformed fribrosarcoma V7T, when compared to the parental non-tumorigenic NIH 3T3 cells. As to normal human cells, as much as 2–4 mg/ml of NaPA were needed to cause a significant inhibition of growth to primary human skin FS4 fibroblasts. It should be noted that the treatment was not toxic to either the malignant or the normal cells.

The concentration range found to selectively suppress malignant growth can be readily obtained in the clinical setting without causing significant side effects. Intravenous infusion of NaPA into humans at 250–500 mg/kg/day which results in plasma levels of 600–800 µg/ml has been found to be a well tolerated treatment. Cytotoxicity in tissue culture was observed when the NaPA concentration was as high as 3 mg/ml or higher.

Example 15:

Phase I clinical trials

Patient Population. Patients were eligible for this study if they had advanced solid tumors for which conventional therapy had been ineffective, a Karnofsky performance status greater than 60%, normal hepatic transaminases and total bilirubin, a serum creatinine less than 1.5 mg/dl, and normal leukocyte and platelet counts. All patients signed an informed consent document that had been approved by the National Cancer Institute (NCI) Clinical Research Subpanel. Seventeen patients, 16 men and 1 woman, with a median age of 57 years (range: 36–75) were enrolled between January and June 1993. Disease distribution included progressive, metastatic, hormone-refractory prostate cancer (9 patients), anaplastic astrocytoma or glioblastoma multiform (6 patients), ganglioglioma (1 patient) and malignant pleural mesothelioma (1 patient).

Drug Preparation and Administration. Sodium phenylacetate for injection was prepared from bulk sodium phenylacetate powder supplied by Elan Pharmaceutical Research Co. (Gainesville, Ga.). The finished injectable stock solution was manufactured by the Pharmaceutical Development Service, Pharmacy Department, Clinical Center, NIH, in vials containing sodium phenylacetate at a concentration of 500 mg/ml in sterile water for injection, USP, with sodium hydroxide and/or hydrochloric acid added to adjust the pH to approximately 8.5. Doses of sodium phenylacetate to be infused over 30 minutes to 2 hours were prepared in 150 ml of sterile water for injection, USP. Doses of phenylacetate to be given over 24 hours were prepared similarly to yield a total volume of 1,000 ml and were administered using an infusion pump.

The protocol as originally designed delivered an i.v. bolus dose of phenylacetate (150 mg/kg over 2 hours) on the first day of therapy, to allow for the estimation of pharmacokinetic parameters. This was followed 24 hours later by a CIVI of the drug for the next 14 days. Cycles of two week drug infusions were repeated every 6 weeks. The rate of drug infusion was to be increased in sequential cohorts of at least three patients, and individual patients could escalate from one dose level to the next with sequential cycles of therapy provided they had experienced no drug-related toxicity and their disease was stable or improved.

The protocol underwent several modifications over the 6 month period. First, the size of the initial bolus dose was reduced from 150 to 60 mg/kg i.v. and the bolus infusion duration from 2 hours to 30 minutes, after the first three patients were treated. This change resulted in drug concentrations optimal for estimating the drug's pharmacokinetics (vide infra) within a six hour time period. Second, after the non-linear nature of phenylacetate's pharmacokinetics was recognized (vide infra), the protocol was changed from a fixed dose escalation (dose levels 1 and 2:150 and 250 mg/kg/day, respectively) to a concentration-guided escalation trial (dose levels 3 and 4:200 and 400 µg/ml, respectively). In the latter format each patient was given an i.v. bolus dose of phenylacetate (60 mg/kg over 30 minutes) one week prior to beginning a 14 day CIVI of the drug. The patient-specific pharmacokinetic parameters estimated from the bolus dose were used to calculate an infusion rate that would maintain the serum phenylacetate concentration at the targeted level during the 14 day infusion. Serum drug concentrations were measured weekly, prompting weekining reestimation of individual pharmacokinetics and dosage adjustment (adaptive control with feedback).

Sampling Schedule. With the initial 150 mg/kg i.v. bolus, blood samples were obtained through a central venous catheter at the following timepoints calculated from the beginning of the infusion: 0, 60, 115, 125, 135, 150, 165, 180, 240, 360, 480, and 600 minutes. For the 60 mg/kg bolus given over 30 minutes, blood sampling was performed at 0, 30, 60, 75, 90, 105, 120, 150, 180, 270 and 390 minutes from the beginning of the infusion. At dose levels 1 and 2, blood samples were obtained daily during the CIVI, while at dose levels 3 and 4, blood samples were obtained on days 1, 2, 3, 8, 9 and 10 of the infusion. Twenty-four hour urine collections for the determination of phenylacetate and phenylacetylglutamine excretion were obtained on days 1, 7 and 14 of therapy. Sampling of the CSF was performed only if clinically indicated.

Determination of sodium phenylacetate and phenylacetylglutamine in serum and urine by high performance liquid chromatography (HPLC). Blood was drawn by venipuncture into a Vacutainer® tube free of anticoagulant and was then refrigerated. It was centrifuged at 1,200 g for 10 minutes in a Sorvall® RT 6000D centrifuge (DuPont Co., Wilmington, Del.) at 4° C. Serum was then removed and stored in Nunc Cryotubes (Nunc Co., Denmark) at −70° C. until the day of analysis.

A standard curve was generated by adding known amounts of sodium phenylacetate (Elan Pharmaceutical Research Co., Gainesville, Ga.) and phenylacetylglutamine (a gift from Dr. S. W. Brusilow, Johns Hopkins University, Baltimore) to a commercial preparation of pooled serum (Baxter Healthcare Corporation, Deerfield, Ill.). The standard values spanned the expected range of serum concentrations: 0, 5, 10, 20, 50, 100, 250, 500, 750 and 1,500 µg/ml.

Two hundred microliters of serum were pipetted into a 1.7 ml Eppendorft tube (PGC Scientifics, Gaithersburg, Md.). Protein extraction was carried out by adding 100 µl of a 10% (v/v) solution of perchloric acid (Aldrich Chemical Co., Milwaukee, Wis.). The tube was vortexed and then centrifuged at 4,500 g for 10 minutes. One hundred and fifty microliters of supernatant were transferred to a new 1.7 ml Eppendorf tube and 25 µl of 20% $KHCO_3$ (w/v) was added to neutralize the solution. This was centrifuged at 4,500 g for 10 minutes and 125 µl of supernatant were transferred to an autosampler vial and maintained at 10° C. until HPLC injection. Urine samples were processed in an identical manner after an initial 1:10 dilution with water.

The HPLC system (Gilson Medical Electronics, Middleton, Wis.) was composed of two pumps (305 and 306), an 805 manometric module, an 811C dynamic mixer, a 117 variable wavelength UV detector and a 231 autosampler fitted with a 20 µl injection loop and cooled with a Grey Line model 1200 cooling device. The column was a Waters® (Millipore Corporation, Milford, Mass.) C18 Nova-Pak, 3.9×300 mm, maintained at 60° C. with a Waters® temperature control module. The mobile phase solutions consisted of fifty microliter samples were auto-injected onto a 10 cm cation-ion exchange column integrated into a Beckman Model 6300 Amino Acid Analyzer (Beckman Instruments Inc., Palo Alto, Calif.). The solvent flow rate (2:1 water/ninhydrin) was maintained constant at 0.5 ml/min. Column temperature was raised by 1.5° C. per minute to elute sarcosine, the internal standard. The column was regenerated with lithium hydroxide at 70° C. following each injection. Absorbance was measured at 570 nm and 440 nm following post-column color development with ninhydrin-RX (Beckman Instruments Inc., Palo Alto, Calif.) at 131° C. Beckman System Gold software was used for data acquisition and data management.

Pharmacokinetic Methods. Initial estimates of $V_{max}$ and $K_m$ for phenylacetate were obtained by generating Lineweaver-Burk plots from concentration versus time curves following i.v. bolus doses. These initial parameter estimates were refined by non-linear least squares fitting, using the Nelder-Mead iterative algorithm, as implemented in the Abbottbase® Pharmacokinetic Systems software package (Abbott Laboratories, Abbott Park, Ill., version 1.0).

Statistical Methods. The Student's t-test was used to compare estimates of phenylacette's pharmacokinetic parameters derived from the Lineweaver-Burk plots with those obtained using non-linear given set of dosing and concentration data was quantified by calculating the weighted sum of the errors squared following non-linear least-squares fitting. The standard deviation of the errors was modeled as a function of drug concentration multiplied by the coefficient of variation of the assay. Confidence regions for the parameters were derived from the weighted sum of squares in the model incorporating the induction parameters, and approximate significance levels for testing between the two models were calculated using the F distribution [Draper, N R, Smith H. Applied Regression Analysis. New York, John Wiley and Sons, p. 282, 1966]. The significance levels of individual cycles were analyzed by the Spearman rank correlation method in an attempt to discern whether a relationship existed between time-dependent changes in drug clearance and dose.

Figure 12:
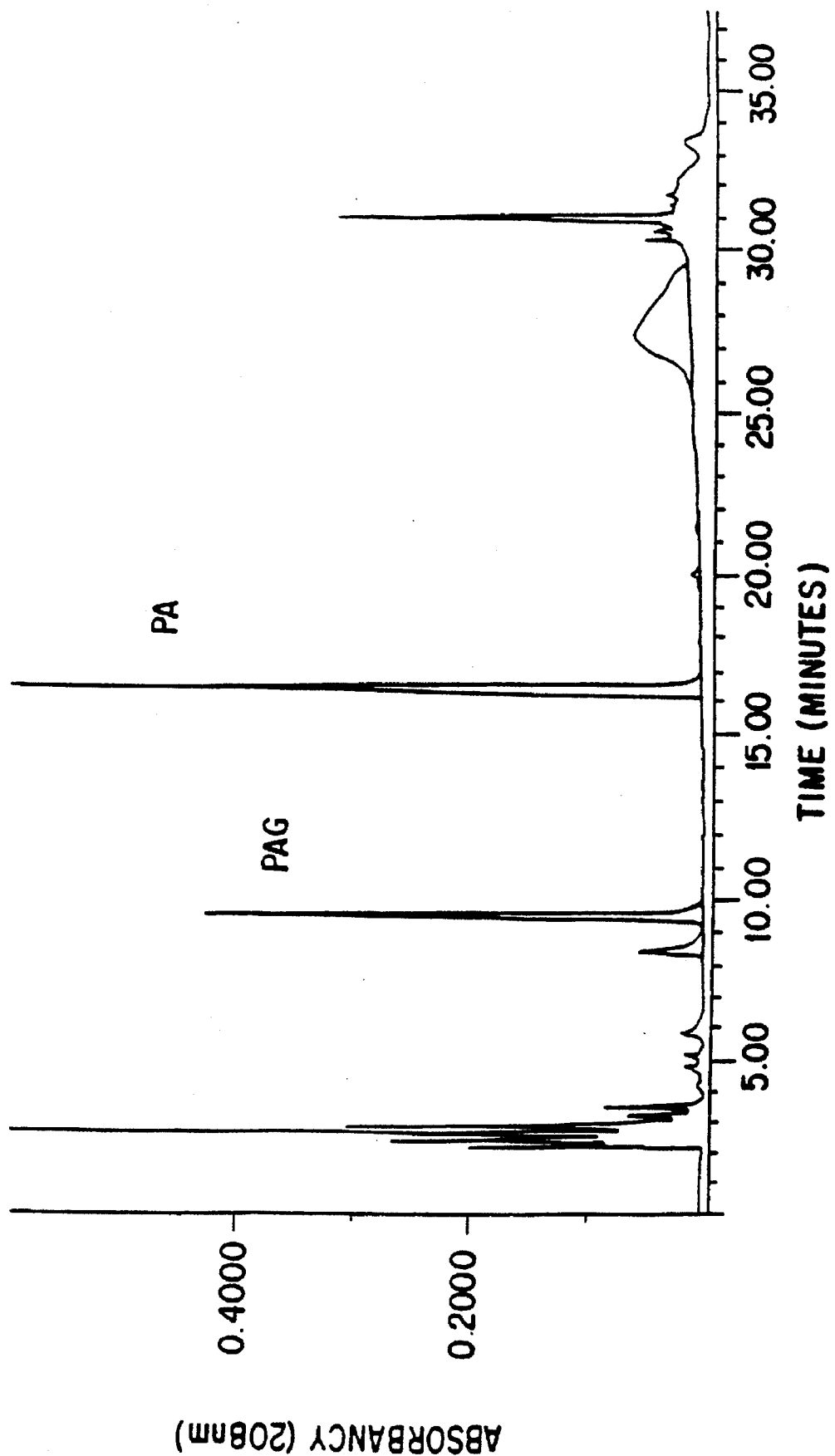
FIG. 12 shows a chromatogram of phenylacetate (PA) and phenylacetylglutamine (PAG). The peaks at 9.8 and 17.1 minutes represent PAG and PA, respectively. Serum concentrations of 250 μg/ml in both instances.
Figure 4:
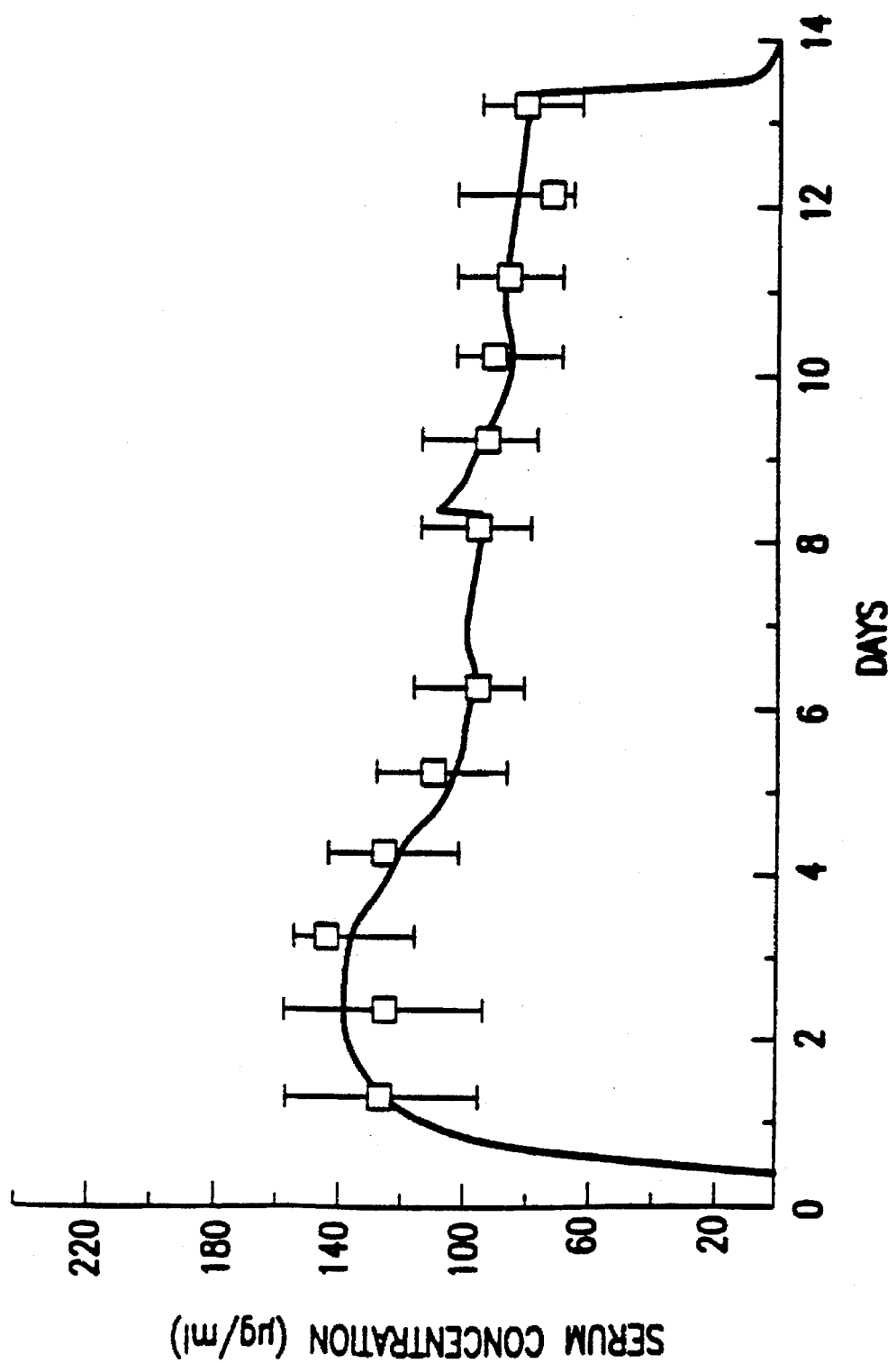

Analytical Assay. The reverse phase HPLC assay allowed both serum phenylacetate and phenylacetylglutamine concentrations to be determined simultaneously from the same sample (see FIG. 12). The lower limit of detection for both compounds in serum and urine was 5 µg/ml, based upon a signal-to-noise ratio of 5:1. The interassay CV for serum concentrations was less than 6% within the range of 40 to 1,000 µg/ml. (Table 14). The lower limit of detection for glutamine was 0.5 µg/ml, with an interassay CV that did not exceed 7%.

Model Specification and Initial Parameter Estimation. FIG. 13 shows representative concentration versus time curves for simultaneously measured serum levels of phenylacetate and pheylacetylglutamine and plasma levels of glutamine following a 150 mg/kg bolus dose of sodium phenylacetate. The post-infusion decline in serum phenylacetate concentration over tim eis linear when plotted on a non-logarithmic scale, consistent with saturable elimination kinetics. While useful for demonstrating a zero-order process, the 150 mg/kg bolus was inadequate for parameter estimation insofar as most of the phenylacetate concentrations obtained over the six-hour sampling period were above $K_m$. In order to generate concentrations both above and below $K_m$, the bolus was changed to 60 mg/kg i.v. over 30 minutes. Visual inspection of the concentration versus time curves following these boluses revealed no evidence of an initial distributive phase, suggesting that a single compartment, open non-linear model should be adequate to describe the drug's pharmacokinetics. Initial estimates (mean±SD) of $K_m$ (90±30 µg/ml), $V_{max}$ (26.0±10 mg/kg/hr) and Vd (22.4±6.8 L) were calculated in 13 patients using the Lineweaver-Burk equation. Refinement of these initial parameter estimates by non-linear least squares fitting of the entire concentration versus time profile for each bolus dose yielded the following estimates: $K_m$=105.1±44.5 µg/ml, $V_{max}$=24.1±5.2 mg/kg/hr and Vd=19.2±3.3 L. The differences between the two methods of estimation were not statistically different, as measured by the Student's t-test (p=0.89).

Induction of Phenylacetate Clearance. In some patients treated at dose levels 1 and 2, we observed a tendency for the serum phenylacetate concentration to decrease with time. An example of this phenomenon is shown in FIG. 14. Considering the 12 cycles of therapy delivered at these levels, a comparison of the serum drug concentration measured on day 2 of CIVI to that observed on day 11 demonstrated a statistically significant decline in concentration with time (Wilcoxon signed rank test, p=0.016). At dose levels 3 and 4, attempts at maintaining targeted serum phenylacetate concentrations using adaptive control with feedback led to variable rates of drug infusion over time, which precluded a simple comparison of drug concentrations at the beginning and end of therapy.

Therefore all cycles of therapy were analyzed at all four dose levels and compared with the performance of the single compartment non-linear model described above with the same model modified to allow $V_{max}$ to increase with time. The formula used to describe this increase was:

$$V_{max,}(t)=V_{max,\ t=0}\times\{1.0+[(IF-1.0)\times(1.0-e^{IR\times t})]\}$$

wherein t is the time elapsed (in hours) since the initiation of therapy, IF is an induction factor representing the maximum-fold increase in $V_{max}$ at infinite time and IR is a first order rate constant (h$^{-1}$) describing the rate at which $V_{max}$ increases over time. Each cycle of therapy (n=21) was evaluated by comparing the difference in the weighted sum of errors squared generated by non-linear least-squares-fitting with each model. The significance of the difference was evaluated using the F test (see statistical methods). In 9 of the 21 cycles, allowing $V_{max}$ to increase with time yielded an improved fit (induction parameters, mean±SD:IF= 1.87±0.37, IR=0.0028±0.003 h$^{-1}$, p≤0.035). The Spearman rank correlation method did not demonstrate a correlation between rate of drug administration and the need to incorporate the two induction parameters into the model (rank correlation coefficient=0.39, p=0.084). The dose rates administered ranged from 450 to 1,850 mg/h.

Review of concomitantly administered medications revealed no association between specific drugs and the occurrence of a time-dependent increase in phenylacetate clearance. In seven patients with primary CNS tumors, treatment with anticonvulsants always antedated the administration of phenylacetate by months to years.

Mechanisms of Phenylacetate Clearance. As shown in FIG. 13, phenylacetate underwent rapid conversion to phenylacetylglutamine. In the three patients who received 150 mg/kg of phenylacetate over 2 hours, the peak serum concentration of phenylacetylglutamine (mean±SD) was 224±81 µg/ml, 325±72 minutes post-infusion. After 60 mg/kg boluses, the peak serum phenylacetylglutamine concentration was 104±33 µg/ml at 86±33 min. The plasma glutamine concentration prior to bolus treatment with phenylacetate was 105±29 µg/ml (mean±SD, n=16), similar to reported values in the literature for normal volunteers. The largest reduction in circulating plasma glutamine levels (46%) was observed in a patient receiving a 150 mg/kg bolus.

The molar excretion of phenylacetylglutamine was determined from 24 hour urine collections. It accounted for 99±23% (n=18) of the dose of phenylacetate administered over the same period of time. The recovery of the free, non-metabolized drug was only 1.5±2.4% of the total administered dose. A strong phenylacetate odor was detectable on patients' clothes and on examiners' hands after physical examination. This suggests that phenylacetate may also be excreted to some extent transdermally.

Distribution of Phenylacetate and Phenylacetylglutamine into the CSF. Clinical circumstances required evaluation of the cerebrospinal fluid in two patients who had metastatic prostate cancer and were free of CNS metastases. The first had reached steady-state phenylacetate and phenylacetylglutamine concentrations of 141 and 199 µg/ml, respectively, the corresponding simultaneous CSF concentrations were 74 and 5 µg/ml, respectively. At the time of simultaneous serum and CSF sampling, the second patient had been off therapy for 6 hours after having reached a serum concentration of phenylacetate of 1044 µg/ml. Measurements in serum and CSF were 781 versus 863 µg/ml for phenylacetate and 374 versus 46 µg/ml for phenylacetylglutamine, respectively.

Clinical Toxicities. No toxicity was associated with bolus administration of the drug. The highest peak serum concentrations were measured after the 150 mg/kg bolus over 2 hours (533±94 µg/ml, mean±SD). Table 15 lists the average serum phenylacetate concentrations per dose level. Although those achieved at dose levels 3 and 4 are close to their target, the large standard deviations reflect our inability to maintain serum phenylacetate concentrations within the desired range, even when using adaptive control with feedback.

Drug-related toxicity was clearly related to the serum phenylacetate concentration. Three episodes of CNS toxicity, limited to confusion and lethargy and often preceded by emesis, occurred in patients treated at dose levels 3 and 4. They were associated with drug concentrations of 906, 1044 and 1285 µg/ml (mean: 950±300 µg/ml), respectively. Symptoms were completely resolved within 18 hours of terminating the drug infusion in all instances, Antitumor Activity. Stabilization of PSA for more than 2 months was noted in 3 of the 9 patients with prostate cancer treated at dose levels 2, 3 and 4 (mean phenylacetate concentration: 234±175 µg/ml). A fourth patient experienced marked improvement in bone pain and was able to substitute a non-steroidal anti-inflammatory drug to his morphine regimen. One patient with glioblastoma multiform has had improvement in performance status (30% on Karnofsky's scale), intellectual function and expressive aphasia of greater than 5 months duration. Although no change in the size of the tumor mass was noted, reduction in peritumoral edema was documented by MRI.

Discussion. Previous descriptions of the pharmacokinetics of phenylacetate have been fragmentary. Simell et al. reported the drug to have first order elimination kinetics with a half-life of 4.2 hours following bolus dose administration 9270 mg/kg) in children [Simell, O, Sipila, I, Rajantie, J, Valle, D L, and Brusilow, S W. Waste nitrogen excretion via amino acid acylation: benzoate and phenylacetate in lysinuric Protein intolerance. *Pediatr. Res.*, 20:1117–1121, 1986]. The failure to recognize the non-linear nature of phenylacetate pharmacokinetics probably resulted from the smaller total doses given to these patients compared to those given in our study. The saturable pharmacokinetics of phenylacetate are consistent with an enzymatic process and our calculations from the 24 hour urinary excretion of phenylacetylglutamine confirm that this is the major route of elimination. Evidence that drug clearance increases with time was derived from the comparison of drug levels on days 2 and 11 of the CIVI, adding another layer of complexity to the pharmacokinetics of phenylacetate. To explain this phenomenon, the potential role of concomitantly administered medications was first considered, but failed to demonstrate any association. Analysis of a the relationship between an increase in drug clearance with time and the rate of drug administration did not reach statistical significance and suffered from the small number of cycles of therapy available for analysis. It should also be noted that, relative to the 14 day period over which it is assessed, $V_{max}$ tended to increase slowly, with an average half-time calculated from the induction rate (IR) of 9.6 days.

As expected for such a small molecule, phenylacetate readily penetrates into the CSF, which may explain the dose-limiting side-effects of the drug, i.e., nausea, vomiting, sedation and confusion.

The results of Table 15 indicate that attempting to maintain serum phenylacetate concentrations at either 200 or 400 µg/ml using adaptive control with feedback was problematic, with drug concentrations that often greatly exceed the level-specific targets. All patients who exhibited CNS toxicity had serum phenylacetate concentrations in excess of 900 µg/ml. In the average patient, the drug must be infused at a rate equal to 75% of $V_{max}$, in order to maintain a constant serum phenylacetate concentration of 400 µg/ml, which is four times greater than $K_m$. Thus, the slightest error in the estimation of individual pharmacokinetics or in the rate of drug infusion results in large changes in drug concentration. Phenylacetate was delivered by CIVI in order to mimic the preclinical conditions that had demonstrated antitumor activity, namely, continuous exposure to concentrations above 475 µg/ml for at least two weeks. Unfortunately, such concentrations cannot be practically maintained.

Figure 16:
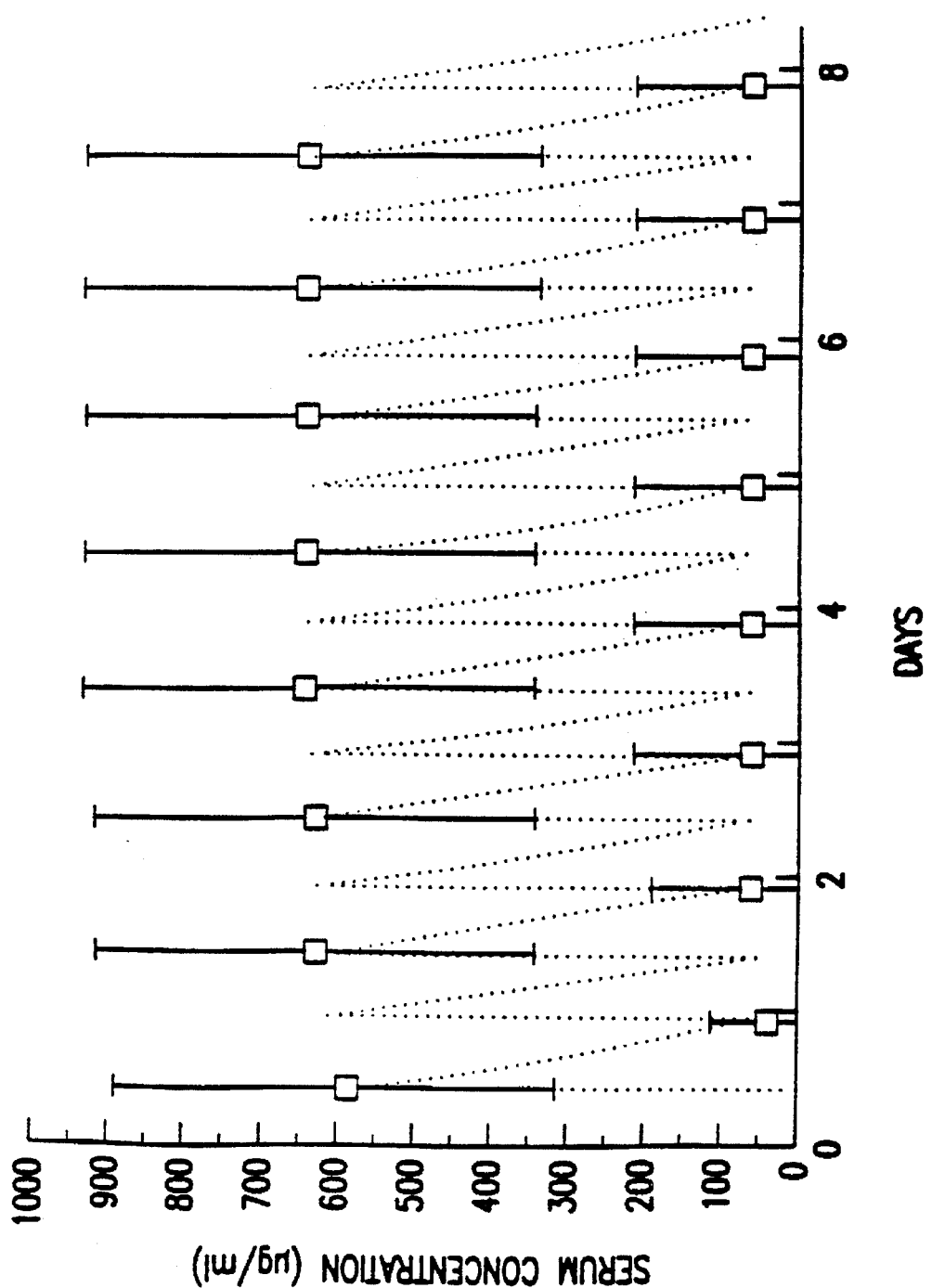

An alternative strategy is to deliver the drug by repeated short infusions. Our limited experience with the 150 mg/kg i.v. boluses suggests that serum phenylacetate concentrations occurring transiently above 500 µg/ml are well tolerated. In addition, the time interval between infusions allows some drug washout to occur, thereby minimizing drug accumulation. A simulated regimen of 200 mg/kg q 12 h (1 hour infusion) is presented in FIG. 16. The simulation assumes that the pharmacokinetic parameters determined from our 17 patients are representative of the cancer population at large and that $V_{max}$ does not change with time. It predicts that a wide range of peak drug concentrations will be present. However, it is possible that these would be sufficiently transient so as not to produce CNS toxicity and the troughs not so prolonged as to abrogate the drug's antitumor activity.

TABLE 14

PA Standard Curve Assay Variability

| PA (μg/ml) | CV (%) | PAG (μg/ml) | CV (%) |
| --- | --- | --- | --- |
| 40 | 2.6 | 40 | 4.6 |
| 400 | 1.7 | 400 | 4.3 |
| 1000 | 3.4 | 1000 | 3.1 |

TABLE 15

PA and PAG Concentrations Per Dose Level During CIVI

| Dose Level | PA dose level | PA* (μg/ml) | PAG* (μg/ml) |
| --- | --- | --- | --- |
| 1 | 150 mg/kg/d | 49 ± 10 | 90 ± 34 |
| 2 | 250 mg/kg/d | 104 ± 40 | 150 ± 63 |
| 3 | 200 μg/ml | 178 ± 85 | 188 ± 55 |
| 4 | 400 μg/ml | 397 ± 244 | 306 ± 51 |

*mean ± SD

Example 16

Effect of NaPA on differentiation of human neuroblastoma cells.

The ability of NaPA to promote the differentiation of human neuroblastoma cells was studied, both alone and in combination with retinoic acid (RA), a known inducer of neuroblastoma differentiation and maturation. In the LA-N-5 cell line, phenylacetate stimulated the differentiation of human neuroblastoma cells as evidenced by dose-dependent inhibition of cell proliferation, neurite outgrowth, increase acetylcholinesterase activity, and reduction of N-myc protein levels. Furthermore, NaPA and RA synergized in inducing LA-N-5 differentiation in that combination treatment resulted in complete cessation of cell growth along with morphologic and biochemical changes indicative of the loss of malignant properties. The combined effects represent a strong differentiation response in neuroblastoma cells, both as to number of responding cells and maturational level achieved. Transient transfection of LA-N-5 cells with a variety of CAT reporter gene plasmids including constructs containing thyroid and RA responsive regulatory elements have suggested that the pathways of action of NaPA and RA may intersect at the nuclear level through activation of common response elements. The synergistic effects, thus, may be mediated by the ability of NaPA to modulate the RA differentiation pathway so as to result in altered transactivation of RA responsive regulatory elements in relevant target genes. These in vitro antineoplastic effects were observed under drug concentrations achievable in humans without significant toxicities.

Section B: Phenylacetate and its Derivatives in the Treatment and Prevention of AIDS The etiology of human acquired immunodeficiency syndrome (AIDS) has been linked to the human immunodeficiency virus (HIV), which is capable of selective infection and suppression of the host immune system. This immune defect renders the human body susceptible to opportunistic infections and cancer development, which are ultimately fatal. The spread of HIV throughout the world is rapid, with no effective therapeutics on hand. It is suggested that NaPA, a nontoxic natural compound capable of glutamine depletion in vivo, can be used in the treatment and prevention of AIDS.

HIV is a retrovirus. The production of retroviruses is dependent on transcriptional activation by the long terminal repeat (LTR) element, and the availability of glutamine (Gln) for translational control. Experimental data obtained with chronically infected cultured cells and animal models indicate that virus replication is specifically inhibited in cells starved for glutamine, but not in those starved for other amino acids (Gloger and Panet (1986); (J. Gen. Virol. 67:2207–2213) Roberts and McGregor, (1991), (J. Gen. Virol 72:2199–305). The results could not be attributed to either an effect on cell cycle or a general inhibition of protein synthesis.

The reason why glutamine depletion leads to virus suppression can be explained as follows. Replication competent murine retroviruses contain an amber termination codon at the junction of gag and pol genes, which can be recognized by amber suppressor tRNA$^{Gln}$. Glutamine is thus essential for the readthrough of viral mRNA transcripts [Yoshinaka et al. (1985); PNAS 82:1618–1622]. Reduction in glutamine concentrations disrupts viral mRNA translational readthrough and protein synthesis, with subsequent inhibition of viral assembly and secondary spread. Although human retroviruses are somewhat different from the murine viruses studied, it has been shown that reduction in the levels of amber suppressor tRNA$^{Gln}$ in human cells infected with HIV causes a significant reduction in the synthesis of viral proteins [Muller et al. Air Research and Human Retroviruses 4:279–286 (1988)]. Such data suggest that agents which can lower glutamine levels in humans are likely to benefit patients infected with HIV. NaPA may be such an agent, since it is known to conjugate to glutamine in humans with subsequent renewed excretion of phenylacetylglutamine. Since NaPA also possesses antitumor activities, the drug is likely to affect Kaposi's sarcomas, the tumors found in as many as 30% of all AIDS patients, as well as lymphomas associated with AIDS.

Example 17

NaPA for treatment of AIDS related disorders

Evidence from experimental model systems in support of the above hypotheses includes:

(a) Preliminary findings with cultured cells indicate that NaPA can inhibit expression of genes controlled by the retroviral LTR; (b) While animal studies have been hindered by the fact that glutamine depletion by NaPA is limited to humans and higher primates, an acceptable animal model (other than primates) involves rodents treated with glutaminase. The expression of retroviral genes is under the control of the long terminal repeat (LTR) element; inhibition of LTR would prevent transcription and synthesis of viral proteins. To examine the effect of NaPA on the retroviral LTR, V7T fibrosarcoma cells carrying an LTR-dependent Ha-ras oncogene were used as a model. Results of Northern blot analysis showed markedly reduced levels of the ras RNA transcription in cells treated with NaPA compared to RNA transcription levels in untreated control cells. The results cannot be explained by a general effect on gene expression, as indicated by the increased expression of the cellular genes collagen and 2'-5' oligo adenylate synthetase (2–5 ASyn). The latter are of particular interest since collagen is a marker of fibroblast differentiation, and 2–5 ASyn is associated with growth control. Taken together, the data indicate the NaPA suppressed the activity of the retroviral LTR, while restoring growth control and differentiation to the host cells. Similarly desirable changes might occur in HIV-infected monocytes and T4 lymphocytes following systemic treatment of afflicted patients with NaPA. Glutaminase is a bacterial enzyme that causes reduction of extracellular (and presumably intracellular) glutamine concentrations. Glutaminase treatment of viremic mice infected with Rouscher murine leukemia virus (RLV) inhibited retroviral replication and the development of splenomegaly, and significantly increased animal survival [Roberts and McGregor J. Gen. Virology 72:29–305 (1991)]. The efficacy of glutaminase therapy compared favorably with AZT, the drug currently used for treatment of AIDS. The results are of particular interest since the RLV serves as a model in the search for anti-HIV drugs (Ruprecht et al., 1986). Unfortunately, however, glutamine depletion by glutaminase in vivo is only transient due to development of neutralizing antibodies to the enzyme. Once this occurs, viral replication can resume, eventually killing the host. NaPA, unlike the bacterial glutaminase, is a natural component of the human body, and thus is less likely to induce the production of neutralizing antibodies; (c) There is clinical evidence for sustained reduction by NaPA of plasma glutamine concentrations. NaPA is currently being used for treatment of hyperammonemia associated with inborn disorders of urea metabolism. Clinical experience indicates that long-term treatment with NaPA effectively reduces glutamine levels. Such treatment is nontoxic and well tolerated even by newborns. In conclusion, NaPA might benefit patients with HIV infection. NaPA could inhibit viral replication through (among other mechanisms) inhibition of LTR and depletion of glutamine, the amino acid required for appropriate processing of viral proteins. If NaPA proves to have anti-HIV activities in humans, it could be used to prevent disease progression in asymptomatic HIV-positive individuals. The lack of toxicity, easy oral administration and relatively low cost uniquely qualify NaPA as a chemopreventive drug. In fact, the drug is so well tolerated by humans that treatment can start just a few hours after birth. In addition, NaPA could be used (alone or in combination with other drugs) in treatment of AIDS-associated disorders including opportunistic infections, HIV encephalopathy, and neoplasia.

Section C: Induction of Fetal Hemoglobin Synthesis in β-Chain Hemoglobinopathy by Phenylacetate and its Derivatives There is considerable interest in identifying nontoxic therapeutic agents for treatment of severe β-chain hemoglobinopathies. Employing the human leukemic K562 cell line as a model, we have explored the cellular responses to NaPA, an amino acid derivative essentially nontoxic to humans. Treatment of cultures with pharmacologically attainable concentrations of NaPA resulted in time- and dose-dependent inhibition of cell proliferation and caused an increase in hemoglobin production. Molecular analysis revealed accumulation of the fetal form of hemoglobin (HbF), which was associated with elevated steady-state levels of gamma globin mRNA. All NaPA effects reversed upon cessation of treatment. Interestingly, addition of NaPA to other antitumor agents of clinical interest, i.e., 5-azacytidine and hydroxyurea, resulted in superinduction of HbF biosynthesis. The results suggest that NaPA, an agent known to be well tolerated by newborns, could be used alone or in combination with other drugs for long-term treatment of some inborn blood disorders.

The pathophysiology of inherited blood disorders such as sickle cell anemia and severe β-thalassemias is based on genetic abnormalities in the β-globin gene which result in deficient or absent β-globin synthesis. The latter prevents the production of hemoglobin and results in ineffective red blood cell production and circulation. Recent data indicate that pharmacological manipulation of the kinetics of cell growth and differentiation might have a beneficial effect in patients with the β-chain hemoglobinopathies, due to the induction of fetal hemoglobin (HbF) synthesis. To date, several antitumor drugs including 5-azacytidine (5AzaC), 5-aza-2'-deoxycytidine (5AzadC), hydroxyurea (HU), vinblastine, and arabinosylcytosine (ara-C) have been shown to increase the production of HbF in experimental models [Dover, Ann NY Acad. Sci. 612:184–190 (199)]. Moreover, there is clinical evidence for 5AzaC and HU activity in severe β-thalassemia and sickle cell anemia, respectively. However, concerns regarding toxic and potential carcinogenic effects of the prevailing antitumor drugs raise the need to identify safe alternatives for long-term treatment of the inborn nonmalignant diseases. The accumulation of fetal hemoglobin in adults is thought to be due to changes in the kinetics of erythroid differentiation rather than a direct effect on the fetal globin genes. According to this hypothesis, other agents that can induce differentiation would also be expected to affect HbF production. The focus here is on the efficacy of a novel nontoxic differentiating agent, NaPA.

As discussed in Section A, Applicant's laboratory has found that NaPA can also affect the maturation (i.e., differentiated state) of various animal and human cell types. The drug caused growth arrest and reversal of malignant properties in a variety of in vitro tumor models including cell lines established from adenocarcinomas of the prostate and lung, malignant melanomas, and astrocytomas. Moreover, NaPA treatment was associated with adipocyte conversion in premalignant mesenchymal C3H 10T1/2 cells, and granulocyte differentiation in promyelocytic leukemia HL-60 cultures. Studies indicated that NaPA, in contrast to the chemotherapeutic differentiating drugs 5AzaC and 5AzadC, may be free of adverse effects such as cytotoxicity and tumor progression.

Indeed, NaPA is well tolerated by humans as indicated by the vast clinical experience with NaPA in the treatment of hyperammonemia in infants with inborn errors of ureagenesis. The clinical experience indicates that acute or long-term treatment with high doses of NaPA is essentially free of adverse effects. The lack of toxicity and the ability to induced cellular differentiation prompted Applicant to examine the effect of NaPA on HbF expression.

Example 18

K562 cells—induction of HbF by treatment with NaPA

The experimental system involved the human leukemic K562 cells, which carry a nonfunctional β-globin gene, but produce low levels of the fetal gamma globin and of HbF. The K562 cell line was originally established from a patient with chronic myelogenous leukemia in the blast cells transformation, and has since been extensively utilized as a model in studies of erythroid differentiation and regulation of the gamma globin gene expression. Applicant has shown that pharmacologically attainable concentrations of NaPA can promote HbF biosynthesis in the human leukemic cells, and can cause superinduction when combined with the other chemotherapeutic agents of interest, 5AzaC and HU.

Cell Culture and reagents. The human leukemia K562 cells were maintained in RPMI 1640 medium supplemented with 10% heat-inactivated fetal calf serum (Gibco), 50 U/ml penicillin, 50 µg/ml streptomycin, and 2 mM L-glutamine unless otherwise indicated. The suspension cultures were kept in exponential growth phase by diluting every 3–5 days with fresh medium, and cell viability was determined by trypan blue exclusion. Phenylacetic acid, 4-hydroxyphenylacetic acid, 3,4-dihydroxyphenylacetic acid, 2,5-dihydroxyphenylacetic acid (Sigma, St. Louis, Mo.) and PAG (a gift from L. Trombetta, Houston, Tex.) were dissolved in distilled water, and brought to pH 7.0 by the addition of NaOH, DON, adivicin, 5AzadC, 5AzaC, and HU (Sigma) were also dissolved in distilled water. All drug stock solutions were stored in aliquots at −20° C. until used.

Determination of Hemoglobin Production. K562 cells were seeded at $1\times10^5$ cells/ml and treated with the drugs for four to seven days prior to assay. Qualitative estimation of hemoglobin production was determined by benzidine staining of intact cells in suspension. The hemoglobin concentration within cells was determined by the protein absorption at 414 nm. Briefly, $1\times10^7$ cells were lysed in 1 ml of lysing buffer (0.12% Tris pH 7.4, 0.8% NaCl, 0.03% Mg-acetate, and 0.5% Np-40), vortexed and incubated on ice for 15 minutes. The lysates were then centrifuged for 15 minutes at 1500 rpm at 4° C., and the absorption of the supernatant monitored between 350 nm and 650 nm using Beckman Du-7 scanning spectrophotometer. The hemoglobin was quantitated using the relationship of 1.0 optical density (OD) at 414 nm corresponding to 0.13 mg/ml hemoglobin as described before.

Northern Blot Analysis and DNA probes. Cytoplasmic RNA was prepared from cultures at logarithmic phase of growth and separated on 1% agarose-formaldehyde gels. Gel electrophoresis, transfer of RNA onto nytran membranes (Schleicher & Schuell), hybridization with radiolabeled DNA probes, and autoradiography (Kodak X-ray film XAR5) were according to established procedures. The probe for gamma globin was a 0.6 Kb EcoRI/HindIII fragment of the human gamma globin gene. Probes were labeled with [$^{32}$P]dCTP (New England Nuclear, Boston, Mass.) using random primed DNA labeling kit (Boehringer Mannheim, West Germany).

Analysis of HbF Protein Synthesis. Newly synthesized proteins were labeled with $^{35}$S-methionine and the HbF immunoprecipitated and analyzed as previously described. Briefly, cells ($1\times10^6$ per point in 1 ml) were first subjected to 1 hr starvation in methionine-free medium, then incubated in the presence of 100 uCi/ml of $^{35}$S-methionine for 2 hrs. The labeled cells were harvested, washed and lysed in a lysing buffer containing 10 mM phosphate buffer pH 7.4, 1% Triton×100, 0.1% SDS, 0.5% deoxycholate, 100 mM NaCl, 0>1% NAN3, 2 mM PMSF, and 10 µg/ml lenpeptin. $1\times10^7$ cpm of TCA precipitable count of cytoextract was incubated with rabbit anti-human HbF (Pharmacia) and protein A Sepharose at 4° C., and the immunoprecipitates were separated by electrophoresis on 12% SDS-polyacrylamide gels.

Figure 17:
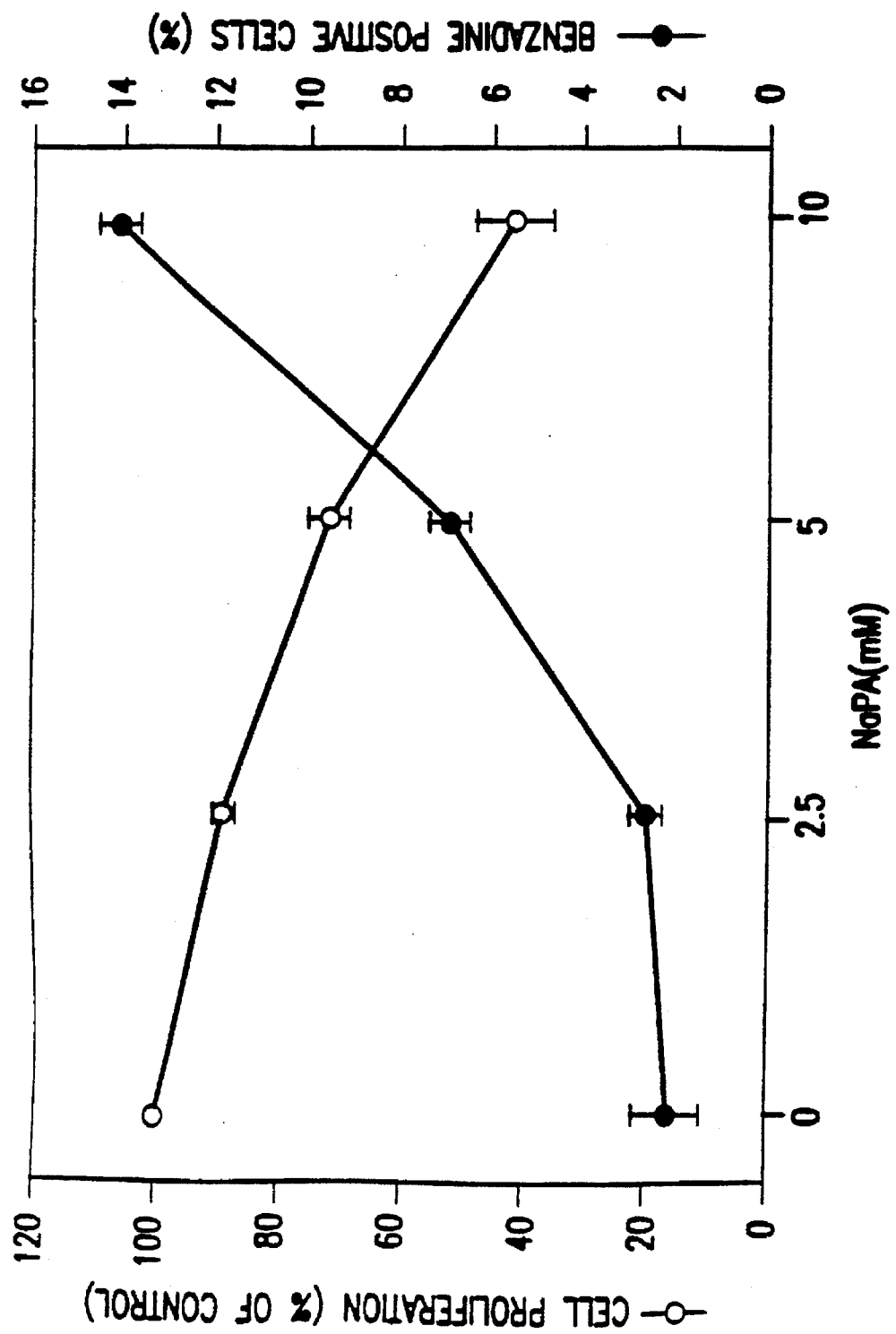
FIG. 17 shows the effect of NaPA on cell growth and differentiation. (o) Total cell number and (•) the fraction of benzidine-positive cells were determined after 4 days of continuous treatment. Data represent means+/−SD (n=4). Cell viability was greater than 95%.

The Effect of NaPA and Analogues on Cell Growth and Differentiation. Treatment of the K562 cultures with NaPA resulted in dose dependent inhibition of cell proliferation, with 1.4 mg/ml causing 50% reduction in cell number after four days of treatment (FIG. 17). No toxicity was observed with doses as high as 2.0 mg/ml. In addition to the cytostatic effect, NaPA also induced erythroid differentiation, as indicated by an increase in the number of benzidine-positive cells (FIG. 17) and confirmed by quantitative analysis of hemoglobin production (Table 16). Similar treatment with PAG, which is the glutamine conjugated form of NaPA, had no significant effect on either cell proliferation or hemoglobin accumulation, suggesting that the changes associated with NaPA treatment are specific and not due to alterations in culture conditions.

The effect of NaPA on cell growth and differentiation could be mimicked by the use of 4-hydroxyphenylacetate (Table 16). This was in marked contrast to the analogues 3,4-dihydroxyphenylacetate and 2,5-dihydroxyphenylacetate, which were highly toxic to the cells (LD50 of 60 and 100 µg/ml, respectively), and did not induce differentiation.

Regulation of Fetal Hemoglobin Production by NaPA. K562 cells normally express low but detectable levels of HbF. Protein analysis employing anti-HbF antibodies revealed significantly increased amounts of HbF in cells treated with NaPA compared to untreated controls; this was associated with elevated steady-state levels of the fetal gamma globin mRNA. The effect of NaPA on HbF production was time and dose dependent, and apparently reversible upon cessation of treatment.

Glutamine Starvation and HbF Production. NaPA treatment of humans can lead to depletion of circulating glutamine due to conjugation to glutamine and formation of PAG, an enzymatic reaction known to take place in the liver and kidney. The in vivo reduction in plasma glutamine was mimicked in vitro by culturing the K562 cells in the presence of lowered glutamine concentrations. Results presented in Table 17 show, in agreement with previous reports, that glutamine starvation alone can affect the growth rate as well as HbF production in the K562 cells. Addition of NaPA to the glutamine-depleted growth medium further augmented the cytostatic and differentiating effects observed. Therefore, the effect of NaPA on erythroid differentiation and HbF production in humans may be even more dramatic than that observed with the in vitro model, due to depletion of circulating glutamine and a direct effect on the erythroid progenitor cells.

Potentiation by NaPA of Erythroid Differentiation induced by Other Chemotherapeutic Drugs. There is considerable interest in the use of 5AzaC, 5AzadC and HU for treatment of sickle cell anemia and β-thalassemia; however, the clinical use of these drugs is often limited by unacceptable toxicities. Combination treatments with nontoxic differentiating agents like NaPA could enhance hemoglobin production while minimizing the adverse effects. Therefore the efficacy of various combinations of NaPA with the other drugs of clinical interest was tested. Results, summarized in Table 18, show that addition of NaPA 800 µg/ml, to low doses of 5AzadC or HU act synergistically to further augment HbF production with no toxic effect to cells. The concentration of HU used in these experiments is comparable to the plasma HU levels measured in sickle cell anemia patients following an oral administration of 25 mg/kg [(Goldberg et al. New England J Med 323:366–372 (1990)]. As to NaPA, pharmacokinetics studies in children with urea cycle disorders indicate that plasma levels of approximately 800 µg/ml can be obtained by infusion with 300–500 mg/kg/day, a treatment well tolerated even by newborns.

Discussion. Chemotherapeutic agents selected for their low cytotoxic/mutagenic potential can be used for induction of fetal hemoglobin in patients with congenital severe anemias such as sickle cell and β-thalassemia. Drug toxicity is an important consideration in view of overall health condition and the variable life-span of patients with these non-malignant blood disorders. Unfortunately, recombinant human erythropoietin, which has proved to be both nontoxic and effective therapy for anemias associated with chronic renal disease, is apparently ineffective in the treatment of sickle cell anemia. The application of other active drugs such as 5AzadC, HU, vinblastine and ara-C has been hindered by concerns regarding their carcinogenic effects. HU is also difficult to use because of the narrow margin between toxicity and the desired effect on increased HbF production

[Dover, et al., Blood 67:735–738 (1986)]. In contrast, NaPA, shown here to affect HbF production, is so well tolerated by humans that treatment can be initiated just a few hours after birth.

Using an in vitro model involving human leukemic K562 cells, it is shown that NaPA can promote the maturation of early erythroid progenitor cells that have an active HbF program. Addition of NaPA to other therapeutic agents currently in clinical use, i.e., 5AzaC, 5AzadC, or HU resulted in superinduction of HbF synthesis. 5AzaC has been shown to be less toxic and more effective than HU in stimulating HbF production. Moreover, 5AzaC, unlike HU, is effective in treatment of both sickle cell anemia and β-thalassemia. Such data are consistent with the interpretation that 5AzaC acts by both perturbation of erythropoiesis and by its effect on DNA methylation. However, while hypomethylation can lead to gene activation and cell differentiation, it can also promote oncogenesis and the evolution of cells with metastatic capabilities. Results obtained with the K562 erythroid progenitor cells indicate that the therapeutic effects of NaPA compare favorably with those of 5AzadC, yet NaPA (unlike the cytosine analog) did not cause tumor progression.

Moreover, NaPA was shown to prevent tumor progression induced by 5AzadC.

The data show that NaPA, used alone or in combination with other drugs is of value in treatment of leukemias and β-chain hemoglobinopathies. In addition to promoting the production of red blood cells expressing HbF through nontoxic mechanisms, NaPA may also minimize the adverse effects of other antitumor drugs currently in clinical use.

TABLE 16

HbF Accumulation in Treated K562 Cells

| Benzidine Treatment (mg/ml) | Positive Cells (%) | fold increase | HbF production (pg/cell) | fold increase |
|---|---|---|---|---|
| None | 2.2 ± 0.8 | 1 | 0.35 ± 0.06 | 1 |
| NaPA | | | | |
| 0.4 | 2.7 ± 0.2 | 1.2 | 0.49 ± 0.02 | 1.4 |
| 0.8 | 7.0 ± 0.3 | 3.2 | 1.15 ± 0.20 | 3.3 |
| 1.6 | 14.6 ± 0.2 | 6.6 | 2.40 ± 0.16 | 6.8 |
| 4HP 1.6 | 14.2 ± 0.5 | 6.45 | ND | |
| PAG 2.6 | 2.1 ± 0.5 | 0.95 | 0.37 ± 0.03 | 1.06 |

TABLE 17

Glutamine Starvation and HbF Production

| | HbF (g/cell) | |
|---|---|---|
| Gln (mM) | Gln starvation alone | plus NaPA (0.8 mg/ml) |
| 2.0 | 0.39 ± 0.04 | 1.0 ± 0.06 |
| 0.5 | 0.56 ± 0.01 | 1.15 ± 0.01 |
| 0.2* | 1.17 ± 0.12 | 1.75 ± 0.22 |
| 0.1* | 1.86 ± 0.40 | 2.22 ± 0.20 |

*The concentration of NaPA used in this study (0.8 mg/ml) is pharmacologically attainable without toxicity. In children such a treatment is expected to cause a drop in circulating glutamine plasma levels to 0.1–0.2 mM. The results presented above indicate that under such conditions HbF production increases 4.5–5.7 fold compared to controls. We propose therefore that the effect of NaPA in children might be more dramatic than that seen under routine culture conditions (i.e., cell growth in medium with 2 mM Gln).

TABLE 18

Potentiation by NaPA of HU's Therapeutic Effect

| Treatment | HbF (pg/cell) |
|---|---|
| None | 0.39 ± 0.04 |
| NaPA (0.8 mg/ml) | 1.64 ± 0.07 |
| HU (50 uM) | 1.00 ± 0.03 |
| HU (50 uM) + NaPA | 5.91 ± 0.6[b] |
| HU (100 uM) | 2.12 ± 0.04 |
| HU (100 uM) + NaPA | 6.71 ± 0.05[b] |

[a]To mimic the effect of NaPA in vivo, treatments involving NaPA were performed in medium supplemented with 0.2 mM Gln (see explanation to Table 17). Control untreated cells and those treated with HU or 5AzadC alone were maintained in growth medium with 2 mM Gln.
[b]The results indicate that NaPA and HU act synergistically to induce HbF Production int he erythroid progenitor cells
Note: Similar results have been obtained for the combination NaPA 0.8 mg/ml and 5AzadC 0.3 uM.

Example 19

HbF induction in nonmalignant and malignant cells

General ability of NaPA and its derivatives to induce production of HbF. The ability of oral administration of sodium 4-phenylbutyrate to increase fetal hemoglobin production was assayed. To do so, the percentage of red cells containing fetal hemoglobin (F cells) was measured by flow-cytometric single-cell immunofluorescent assays in 15 patients (7 females and 8 males) with hereditary urea-cycle disorders who had received sodium 4-phenylbutyrate therapy for 5 to 65 months. In determining the differences in low levels of fetal hemoglobin in persons without anemia, the measurement of the percentage of F cells is more precise than conventional measurements of fetal hemoglobin as a percentage of total hemoglobin. The mean percentage of F cells was significantly higher in the patients than in normal subjects:

| Patient No. | Age yr | Dose of Phenylbutyrate g/kg/day | F Cells* % |
|---|---|---|---|
| 1 | 29 | 0.30 | 9.4 |
| 2 | 11 | 0.67 | 20.4 |
| 3 | 6 | 0.62 | 0.5 |
| 4 | 5 | 0.48 | 6.5 |
| 5 | 2 | 0.58 | 22.7 |
| 6 | 13 | 0.46 | 7.7 |
| 7 | 2 | 0.38 | 11.8 |
| 8 | 11 | 0.41 | 1.9 |
| 9 | 6 | 0.27 | 1.9 |
| 10 | 5 | 0.62 | 2.3 |
| 11 | 6 | 0.65 | 21.1 |
| 12 | 21 | 0.29 | 1.7 |
| 13 | 3 | 0.47 | 7.6 |
| 14 | 6 | 0.64 | 40.5 |
| 15 | 2 | 0.63 | 29.7 |
| Patients, mean ± SE | — | | 12.4 ± 3.1** |
| Normal subjects, mean ± SE | — | | 3.1 ± 0.2 |

*F cells were measured with a flow-cytometric technique that counts the percentage of F cells in a total of 10,000 red cells. The difference between repeated measurements was less than 10 percent.
**P = 0.005 by the Kolmogorov-Smirnov two-sample test for the comparison of the F-cell values in the 15 patients with urea-cycle disorders and the values in 293 normal adults. The percentage of F cells reaches the range of values found in normal adults at about two years of age.

Example 20

In vitro study of sickle cell and beta-thalassemia responses to NaPA/NaPB

An in vitro study was conducted on cells derived from patients with homozygous sickle cell disease or β-thalassemia who had been admitted to the Clinical Center of the National Institutes of Health (NIH) for routine evaluation, or normal blood donors from the Department of Transfusion Medicine (NIH). Approximately 20–25 ml of blood was obtained for erythroid cell cultures. Diagnosis of SS or B-thal was made on the basis of: (1) hemoglobin electrophoresis on alkaline cellulose acetate and on acid citrate sugar; (2) peripheral blood examination; and occasionally (3) DNA and RNA analysis of bone marrow aspirates. When possible, diagnosis was confirmed by family studies. Routine hematologic profiles were performed on a Coulter Model S.

Peripheral blood mononuclear cells were isolated by centrifugation on a gradient of Ficoll-Hypaque and cultured for 7 days (phase I) in alpha-minimal essential medium supplemented with 10% fetal calf serum (FCS) (both from GIBCO, Grand Island, N.Y.), 1 μg/ml cyclosporin A (Sandoz, Basel, Switzerland) and 10% conditioned medium collected from bladder carcinoma 5637 cultures (Myers C D, Katz F E, Joshi G, Millar J L: A cell line secreting stimulating factors for CFU-GEMM culture. Blood 64:152, 1984). In phase II, the non-adherent cells were recultured in alpha-medium supplemented with 30% FCS, 1% deionized bovine serum albumin, $1 \times 10^5 M$ 2-mercaptoethanol, 1.5 mM glutamine (unless otherwise indicated), $1 \times 10^6 M$ dexamethasone, and 1 U/ml human recombinant Epo (Ortho Pharmaceutical Co., Raritan, N.J.). These cultures yielded up to $10^6$ erythroid cells per milliliter of blood. Cell viability was determined by Trypan Blue exclusion. Phenylacetic acid, 4-phenylbutyric acid, p-hydroxyphenylcetic acid, p-chlorophenylacetic acid, and butyric acid (Sigma, St. Louis, Mo.) were dissolved in distilled water and brought to pH 7.0 by the addition of NaOH. 5-Azacytidine and hydroxyurease was obtained from Sigma, and PAG was obtained from S. Brusilow (Johns Hopkins, Baltimore, Md.).

Differentiation was assessed morphologically by preparing cytocentrifuge slides stained with alkaline benzidine and Giemsa. The number of Hb-containing cells was determined using the benzidine-HCl procedure (Orkin S H, Harosi F L, Leder P: Differentiation of erythroleukemic cells and their somatic hybrids. Proc Natl. Acad. Sci USA 72:98, 1975). Hbs were characterized and quantitated by cation exchange high performance liquid chromatography (HPLC) of cell lysates as previously described (Huisman TH: Separation of hemoglobins and hemoglobin chains by high performance liquid chromatography. J Chromatography 418:277, 1987). Total Hb in lysates prepared from a known number of Hb-containing (benzidine-positive) cells was measured using either the tetramethylbenzidine procedure (Sigma kit, Catalog No. 527) or by cation exchange HPLC (measuring total area under chromatogram). Standard Hb solutions (Isolab, Inc., Akron, Ohio) were used for reference. Mean cellular Hb (MCH) was calculated by dividing the total Hb content of the lysate by the number of benzidine-positive cells.

Cytoplasmic RNA was separated on 1% agarose-formaldehyde gels. RNA isolation, gel electrophoresis, transfer onto Nytran membranes (Schleicher & Schuell, Inc., Keene, N.H.), hybridization with radiolabeled DNA probes, and autoradiography (Kodak X-ray film XAR5) were described [Samid D, Yeh A, Presanna P: Induction of erythroid differntiation and fetal hemoglobin production in human leukemic cells treated with phenylacetate. Blood, 80:1576, 1992]. The human globin cDNA probes included JW101 (alpha), JW102 (beta), and a 0.6 kb EcoRI/HindIII fragment of the 3' end of human G-gamma-globin gene. Probes were labeled with [$^{32}$P]dCTP (New England Nuclear, Boston, Mass.) using a random primed DNA labeling kit (Boehringer, Mannheim, Germany).

Figure 18:
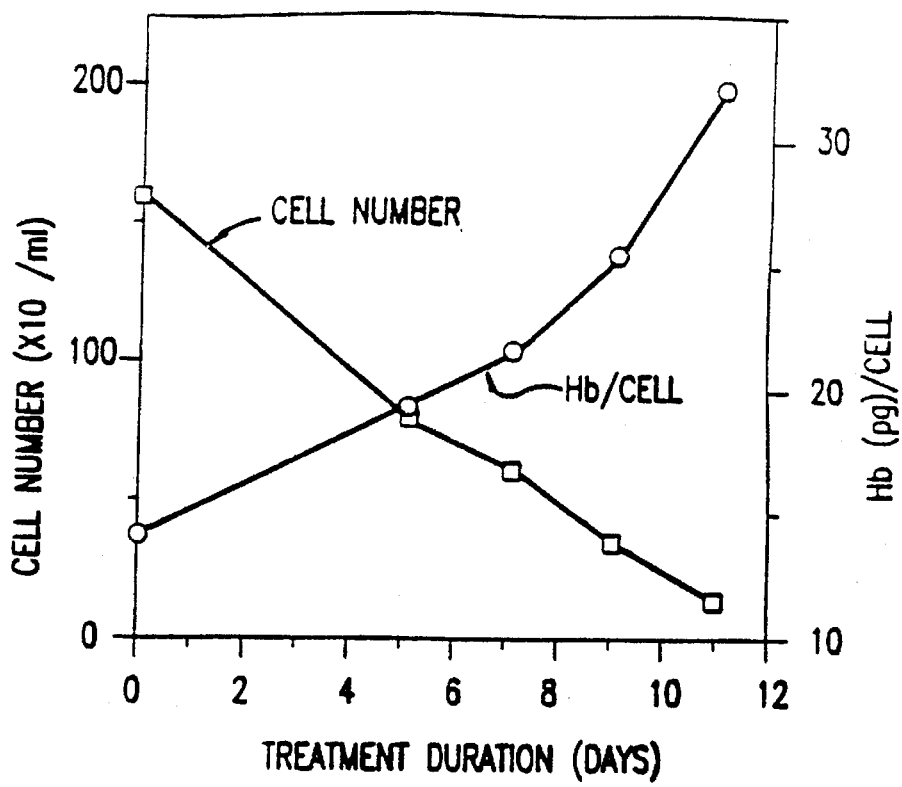
FIGS. 18A and 18B show the time-dependent changes in cell proliferation and Hb production. NaPA (5 mM) was added on days 2, 4, 6, and 8 of phase II cultures derived from normal donorsl, and the cells were analyzed on day 13. Panel A: Nubmer of Hb-containing cells per ml (×10⁻⁴), and the amounts of Hb (pg) per cell (MCH). Panel B: Total Hb (pg) per ml culture, and the proportion of HbF out of total Hb (% HbF). Data points represent the means of four determinations. The deviation of results of each determination from the mean did not exceed 10%. NaPB at 2.5 mM produced comparable effects (not shown). In all cases, cell viability was over 95%.
Figure 18:
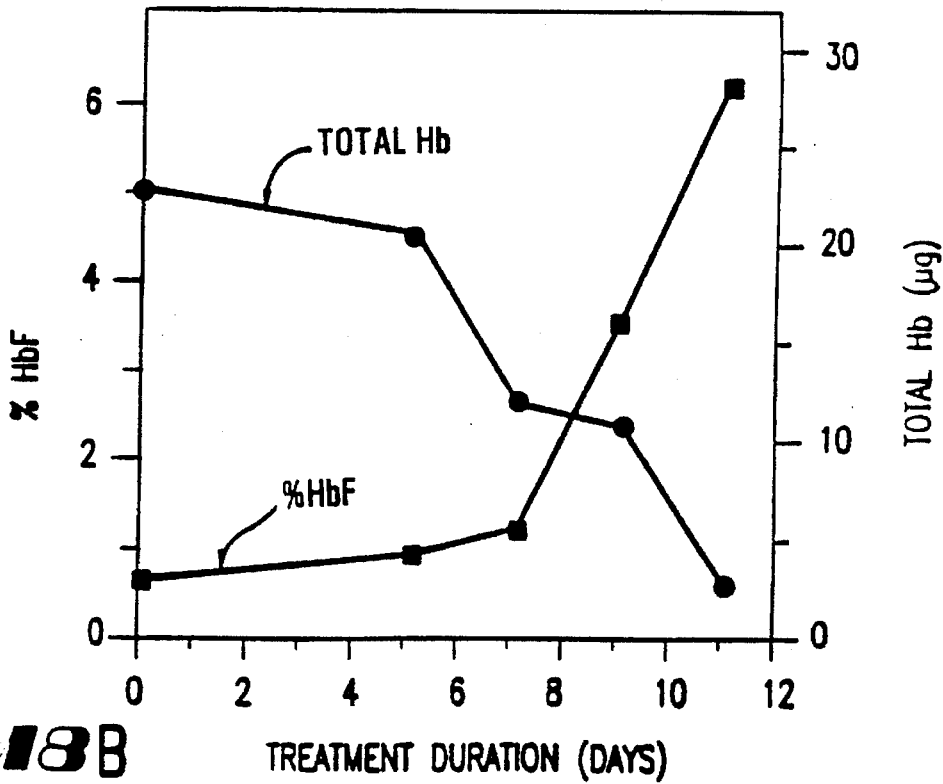
Figure 19:
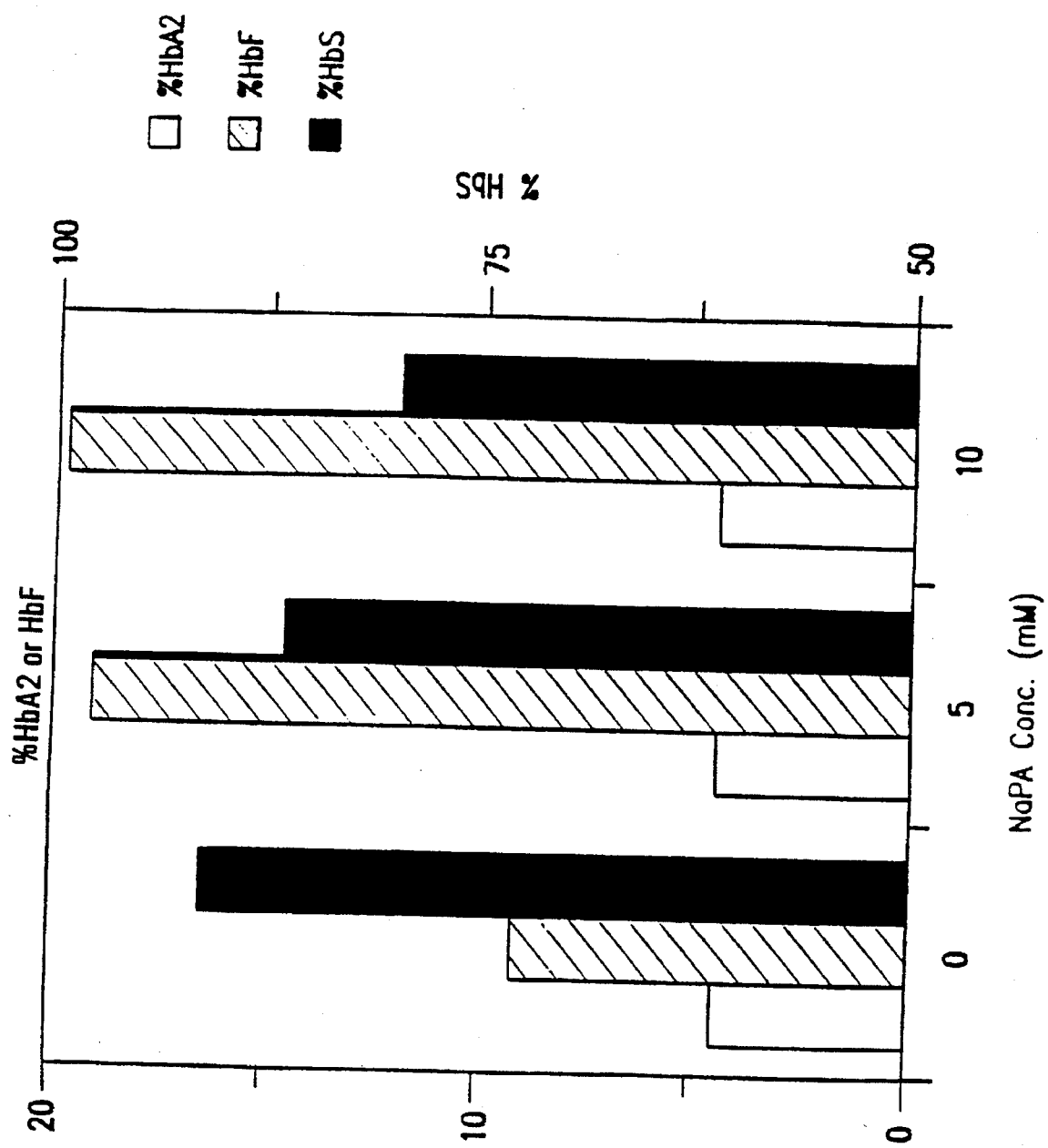
FIG. 19 shows the effect of NaPA on the proportions of Hb species in cultured erythroid precursors derived from a patient with sickle cell anemia. NaPA was added to 7 day phase II cultures. The cells were harvested and lysed on day 13, and the proportions of HbF, HbA$_2$, and HbS were determined following separation on cation exchange HPLC.

Results. Addition of NaPA or NaPB to phase II erythroid cultures resulted in reduced cell proliferation with no apparent change in cell viability. Cytostatis was associated with a decline in total Hb produced per culture; however, both Hb content per cell (MCH) and the proportion of HbF (% HbF) increased upon treatment (FIG. 18). The extent of changes observed was dose- and time-dependent: the earlier the drugs were added during the second phase of growth, the higher was the increase in % HbF, however, cell yields were proportionately decreased. For example, addition of 5 mM NaPA to normal precursors on day 2 caused approximately 90% decrease in cell number along with a 12-fold increase in % HbF, a determined on day 13. When treatment was initiated on day 67, cell number decreased on by 60% compared to controls, and % HbF increased 3.3-fold. In order to obtain sufficient cells for further analysis, subsequent experiments involved the addition of drugs on days 6–7, and cells were harvested on day 13. Under these conditions, results were reproduced in cultures derived from 6 normal donors as well as 4 patients with sickle cell anemia and 4 patients with B-thal. NaPA (5 mM) and NaPB (2.5 mM) caused a significant increase in both MCH(38–100%) and the proportion of HbF produced. In the case of homozygous SS patients, % HbF was elevated 2.0–4.1 fold (mean 3.0) by 4 mM NaPA, and 3.2–5.6 fold (mean 4.0) by 2.5 mM NaPB. The latter was associated with a 12±3% decrease in HbS levels, with no change in $HbA_2$ (FIG. 19).

As in K562 cells, increased HbF production by NaPA or NaPB in primary cultures of normal or SS cells appears to be due to pre-translational regulation of gamma-globin expression. Northern blot analysis showed dose-dependent increase (up to 5 fold) in the steady-state levels of gamma globin mRNA, accompanied by a slight decrease (less than two fold) in the amounts of beta globin transcripts. There was no change in alpha globin expression.

PAG, the end-metabolite of both NaPB and NaPA, is formed by phenylacetate conjugation to glutamine with subsequent excretion in the urine. PAG was found to be inactive on erythroid proliferation and HbF accumulation. Glutamine starvation of the non-malignant erythroid cells had no effect on either cell growth or HbF production, nor did it enhance the efficacy of NaPA.

The effect of NaPA with other drugs was also assayed. When used alone in cultures derived from normal donors (HbF base levels of 0.8–2.0 %), NaPA (5 mM) and hydroxyurease (0.05 mM) increase % HbF by 3.5 and 2.0-fold, respectively; the combination of the two resulted in a 4.7-fold increase in HbF. NaPA also augmented HbF stimulation by butyrate (0.5 mM) (from 3.1 to 7.15-fold), and of 5-Azacytidine (2 uM) (from 2.5 to 6.6-fold). These results indicate that NaPA when added to suboptimal, non-toxic doses of other drugs, can potentlate HbF production with significant cytostasis and no signficant change in cell viability.

As exemplified below in Table 20, combination treatment comprising administration of NaPA (or a pharmaceutically acceptable derivative of phenylacetic acid) simultaneously with hemin, a known stimulator of HbF production, synergistically increases the induction of erythroid differentiation, as indicated by the increase in the number of benzidine positive cells, and HbF production. In K562 cells, the range of increase in the production of HbF with this combination treatment varied from 1.5 to 5 times that produced by treatment with 10 mM PA alone. Further, treatment with NaPB in combination with hemin also resulted in classical synergism. Similar results were also obtained with PB in non-malignant erythroid progenator primary cells. In all cases, treatment with both drugs was maintained for 4–6 days prior to measurement of HbF.

TABLE 20

STIMULATION OF HbF BY NaPA IN COMBINATION WITH HEMIN - K562 MODEL

| $R_x$ | % Benzidine pos. | Hb pg/cell | Viability |
| --- | --- | --- | --- |
| CONTROL | >0.01 | 0.26 | 97 |
| NaPA (10 mM) | 1.6–3.1 | 0.91 | 96 |
| NaPA (10 mM) + H | 25.4–32.6 | 4.03 | 92 |
| NaPA (5 mM) + H | 12.6 | 2.34 | 99 |
| NaPA (2.5 mM) + H | 8.1 | 1.95 | 94 |
| HEMIN (20 µM) | 2.9 | 1.04 | 98 |
| CONTROL | 2.1 | 0.65 | 97 |
| NaPA (2.5 mM) | 2.6 | 0.91 | 97 |
| NaPA (5 mM) | 7.7 | 1.04 | 97 |
| NaPA (10 mM) | 14.3 | nd | 96 |
| HEMIN (20 µM) | 13.8 | 2.34 | nd |
| NaPA (5 mM) + H | 42.3 | 5.2 | 97 |

Section D: Use of Phenylacetic Acid and its Derivatives in Wound Healing

Growth factors, including TGF-α, play a critical role in wound healing and repair processes. Wound healing is a localized process that involves inflammation, wound cell migration and mitosis, neovascularization, and regeneration of the extracellular matrix. Recent data suggest the action of wound cells may be regulated by local production of peptide growth factors which influence wound cells through autocrine and paracrine mechanisms (Schultz et al., *J. Cell Biochem.* 45(4):346 (1991); Schultz et al., *Acta Ophthalmol. Suppl.* (*Copenh*), 202:60 (1992)). Two peptide growth factors which may play important roles in normal wound healing in tissues such as skin, cornea, and the gastrointestinal tract are the structurally related epidermal growth factor (EGF) and TGF-α, whose receptors are expressed by many types of cells including skin keratinocytes, fibroblasts, vascular endothelial cells, and epithelial cells of the gastrointestinal tract. EGF or TGF-α is synthesized by several cells involved in wound healing, including platelets, keratinocytes, activated macrophages and corneal epithelial cells. Healing of a variety of wounds in animals and patients, such as epidermal regeneration of partial thickness burns, dermatome wounds, gastroduodenal ulcers and epithelial injuries to the ocular surface, is enhanced by exogenous treatment with EGF or TGF-α. TGF-α, which is a potent inducer of lysyl oxidase mRNA levels in cultures of human scleral fibroblasts, may be primarily responsible for inducing synthesis of extracellular matrix components after an injury. Furthermore, TGF-α is known to promote anglogenesis.

Figure 20:
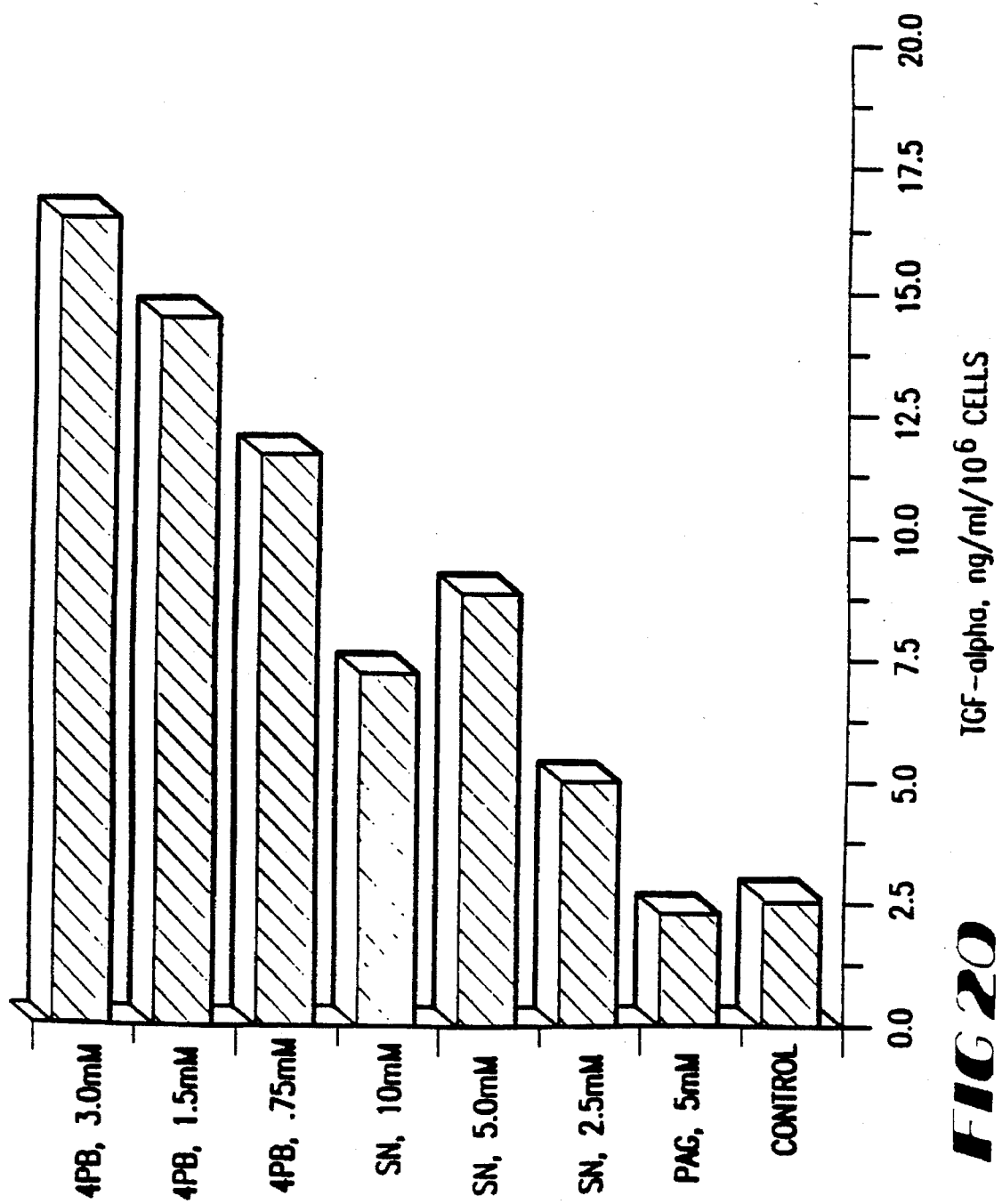
FIG. 20 shows the increased production of TGF-α by human keratinocytes upon treatment with NaPA and NaPB. Epithetial HK5 cells were treated with NaPB (3.0 mM, 1.5 mM, 0.75 mM), NaPB (10 mM, 5.0 mM, 2.5 mM) and PAG (5 mM) continuously for 4 days. Untreated cells served as a control. The amount of TGF-α (ng/ml/10⁶ cells) was measured by using anti-TGF-α antibodies.

The lack of adequate stimulation of growth factors contributes to the nonhealing conditions of many chronic wounds. Poorly healing conditions could markedly benefit from either addition of exogenous TGF-α or stimulation of effector cells to produce TGF-α and related growth factors. It has now been discovered that PA and PB (or a pharmaceutically acceptable derivative) are capable of stimulating production of TGF-α in cells of melanocytic origin; astrocytic lineage (glioblastoma cells); and several normal human epithelial cell types, including keratinocytes (FIG. 20), which are involved in wound healing. Further, treatment with PA and PB enhances collagen-α type 1 expression. Induction TGF-α mRNA expression upon treatment with NaPA and NaPB in human melanoma cells; was observed expression of TGF-α was confirmed following protein analysis. FIG. 20 shows the increased production of the TGF-α protein in human keratinocytes upon exposure to NaPA and NaPB. This increased production of TGF-α is maintained for a few days after which the levels return to approximately pretreatment levels. As discussed below and in FIG. 21, further support for the use these compounds in treating wounds may be found in the enhanced expression of ICAM-1, which is a cellular adhesion molecule/surface antigen, following treatment with NaPB.

Thus, the instant invention provides a method for stimulating the production of TGF-α in cells. Further, wound healing in a human or animal can be enhanced by treatment with a therapeutic amount of phenylacetic acid or a derivative of phenylacetic acid such as NaPA or NaPB, which stimulates the in-situ production of TGF-α. For instance, surface wounds can be treated by topically applying PA, PB or a derivative of either PA or PB to the skin surface, such as in a cream formulation. Likewise, ocular injuries can be treated by application of a PA or PB (or PA/PB derivative) formulation, such as eye drops, to the cornea. Similarly, internal injuries, such as injuries to the gastrointestinal tract, can be treated by administration of oral formulations. Vaginal or anal injuries can also be treated, such as with a suppository containing pharmaceutically effective amounts of PAA or a derivative. The PA/PB or derivative formulations can be administered continuously or, preferably, intermittently, such as one or more doses in daily, weekly or monthly courses. For example topical administration once or twice a day of a composition containing from 0.1 to 10 mM PA, preferably 0.1 to 5.0 mM PA or from 0.1 to 5 mM PB, preferably 0.1 to 2.5 mM PB over the course of a week adequately stimulates wound repair. From the information contained herein, dosage concentrations and amounts for the various administration vehicles can be easily determined. For instance, a topical treatment, such as a cream containing PB, typically will contain approximately 0.5 to 3.0 mM PB or an equipotent (by equipotent it is meant that dosage may be varied among the different phenylacetic acid derivatives so as to achieve the equivalent effect on the subject) dose of a phenylacetic acid derivative. For instance, and without limitation, approximately one-half as much PB in a dose is needed to equal the potency of a similarly indicated PA dose.

Section E: Use of Phenylacetic Acid or its Derivatives in Treatment of Diseases Associated with Interleukin-6

Interleukin-6 (IL-6), which can be produced by monocytes and keratinocytes upon stimulation, is a pleiotropic cytokine that plays a central role in defense mechanisms, including the immune response, acute phase reaction and hematopoiesis. Activation of mature B cells can be triggered by antigen in the fluid phase. When antigen binds to cell membrane IgM in the presence of IL-1 and IL-6, mature virgin B cells differentiate and switch isotypes to IgG, IgA or IgE. Abnormal expression of the IL-6 gene has been suggested to be involved in the pathogenesis and/or symptoms of a variety of diseases, including (1) non-malignant disorders associated with abnormal differentiation programs, autoimmunity and inflammatory processes, e.g., rheumatoid arthritis, Castleman's disease, mesangial proliferation, glomerulonephritis, uveitis, sepsis, autoimmune diseases such as lupus, inflammatory bowel, type I diabetes, vasculitis, and several skin disorders of cell differentiation such as psoriasis and hyperkeratosis; (2) viral diseases such as AIDS and associated neoplasms, e.g., Kaposi's Sarcoma and lymphomas; and (3) other neoplasms, e.g., multiple myeloma, renal carcinoma, Lennert's T-cell lymphoma and plasma cell neoplasms. For instance, significantly increased IL-6 mRNA levels in lesional psoriatic tissue relative to normal tissue and elevated amounts of IL-6 in sera and peripheral blood mononuclear cells of psoriatics compared to samples from atopics or healthy controls have been found (Elder et al., *Arch. Dermatol. Res.*, 284(6):324 (1992); Neuner et al., *J. Invest. Dermatol.*, 97(1):27 (1991)).

It has now been discovered that phenylacetic acid or a derivative of phenylacetic acid, such as NaPA or NaPB, can inhibit the expression of IL-6. For instance, PA inhibits IL-1-induced IL-6 expression in colon carcinoma cells. This reduction in RNA is confirmed by reduction in IL-6 protein. Thus, PA, PB and their derivatives can be used in the treatment of diseases involved with the abnormal overexpression of IL-6.

For instance, treatment twice daily by topical application of either 2 mM NaPB in a mineral oil-based cream or 2 mM napthylacetate and Vitamin $B_1$ in a mineral oil-based cream directly onto the patient's psoriatic lesions resulted in disappearance of the lesions within a week. Similar treatment of a patient with a severe case of psoriasis resulted in the psoriatic lesions resolving in approximately 1–3 weeks. Obviously, the mode of administration and amount of drug can vary depending upon the IL-6-related disease being treated in order to target the drug to the cells in which reduction of IL-6 expression is desired. For example, injection of a 0.1 mM–5 mM PB solution or an equipotent solution containing a pharmaceutically acceptable phenylacetic acid derivative into the joint region may be appropriate for treatment for rheumatoid arthritis whereas other diseases may be more appropriately treated by topical, intravenous or oral delivery. Treatment can be by either continuous or discontinuous treatment, but cessation of the drug, particularly PB, may be accomplished by ramping down the dosage amounts to prevent an overreaction to the cessation of treatment with the drug. Additionally, diseases involving the abnormal overexpression of IL-6 can be treated by administration of an effective amount of phenylacetic acid or a phenylacetic acid derivative, particularly PA or PB, in combination with an effective amount of an anti-inflammatory agent, including various vitamins such as vitamin $B_1$, non-steroidal inflammatory agents and steroidal anti-inflammatory agents. The anti-inflammatory agent can be combined with the phenylacetic acid derivative(s) of this invention in the same dosage form or administered separately by the same or different route as the derivative. An effective amount of the anti-inflammatory agent refers to amounts currently in clinical use for the specific disease state or less.

Section F: Use of Phenylacetic Acid or its Derivatives in the Treatment of AIDS-Associated CNS Dysfunction Hallmarks of central nervous system (CNS) disease in AIDS patients are headaches, fever, subtle cognitive changes, abnormal reflexes and ataxia. Dementia and severe sensory and motor dysfunction characterize more severe disease. Autoimmune-like peripheral neuropathies, cerebrovascular disease and brain tumors are also observed. In AIDS dementia, macrophages and microglial cells of the CNS are the predominant cell types infected and producing HIV-1. However, it has been proposed that, rather than direct infection by HIV-1, the CNS disease symptoms are mediated through secretion of viral proteins or viral induction of cytokines that bind to glial cells and neurons, such as IL-1, TNF-$\alpha$ and IL-6 (Merrill et al., *FASEB J.*, 5(10):1291(1991)). TGF-$\beta$ is a growth factor which is released by many cell types. Among other effects, TGF-$\beta$ is highly chemotactic for macrophages and fibroblasts and stimulates the release of TNF-$\alpha$, TGF-$\alpha$ and, indirectly, a variety of other modulators from macrophages which have been implicated in the initiation of the CNS symptoms of AIDS.

It has now been discovered that phenylacetic acid or a derivative of phenylacetic acid, such as NaPA or NaPB, can inhibit the production of TGF-$\beta 2$. Because TGF-$\beta 2$ is an immunosuppresive factor, this inhibition results in a general improvement of the patient's immune system. Gene expression of TGF-$\beta 2$ in glioblastoma cells was inhibited by both PA and PB. This reduction in RNA leads to reduced TGF-$\beta 2$ protein synthesis. Thus, PA, PB or their derivatives can be used to inhibit the production of TGF-$\beta 2$ in cells, particularly to control or alleviate the CNS symptoms resulting from HIV infection. As discussed above, this treatment also inhibits the production of IL-6, further allowing for alleviation of the CNS symptoms. Amounts of drug and/or regimens of administration effective for inhibiting TGF-$\beta 2$ correspond to those appropriate for treatment or prevention of cancer as given herein, such as in SECTION C.

Section G: Use of Phenylacetic Acid and its Derivatives to Enhance Immunosurveillance Immunosurveillance in an animal such as a human can be enhanced by treatment with PA, PB or their derivatives. Tumor cells are thought to escape attack by the immune system by at least two means. First, many tumors secrete immune suppressive factors that directly reduce immune activity. Additionally, some tumor cells do not express, or have reduced expression of, appropriate surface antigens that allow the immune system to identify outlaw cells. However, the compositions of the instant invention can activate otherwise dormant genes such as fetal globin, perhaps by DNA hypomethylation. Similarly, activation of cancer suppressor genes, dormant antigens and other genes, such as (1) cellular major histocompatibility antigens (MHC Class I and II) or other surface antigens, such as ICAM-1; (2) tumor antigens such as MAGE-1; and (3) viral latent proteins such as EBV's latent membrane protein (which is implicated in numerous diseases such as T-cell neoplasms, Burkitt's lymphoma nasopharyngeal carcinoma, and Hodgkin's disease), may contribute to enhanced immunosurveillance. Thus, neoplastic cells can be treated with PA, PB or their derivatives to provide for expression of cell surface antigens that increase the effectiveness of the immune system by allowing for adequate identification and clearance of the tumor cells by the immune system. Activation of latent viral proteins could also induce a lyric cycle leading to death of the infected cell.

Figure 21:
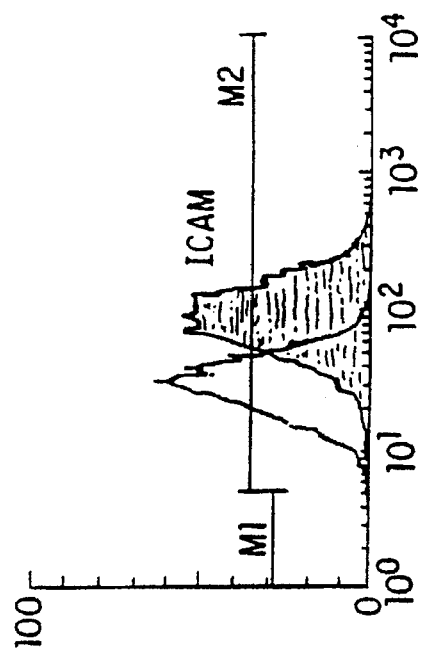
FIG. 21 (A,B,C,D) shows the enhanced expression of the surface antigens W6/32 (MHC class I), DR (MHC class II) and ICAM-1 in melanoma cells treated with NaPB. Melanoma 1011 cells were treated with 2mM PB for 10 days. Treatment was discontinued for 3 days to document the stability of the effect. FACS analysis revealed markedly increased expression of the antigens following treatment (shaded area); the expression of the surface antigens was similar or slightly greater on day 13 than on day 10, indicating that PB induced terminal differentiation.
Figure 21:
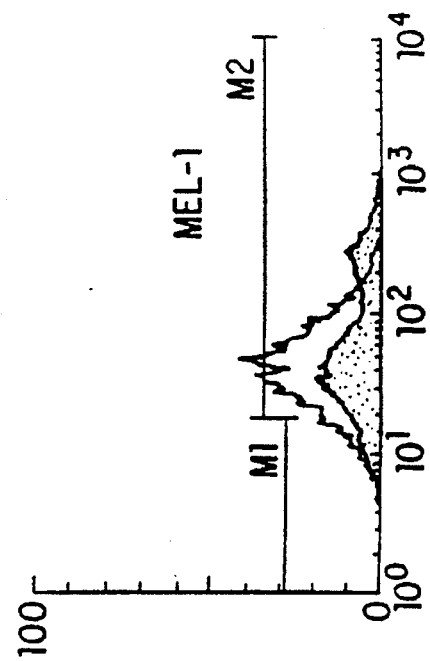
Figure 21:
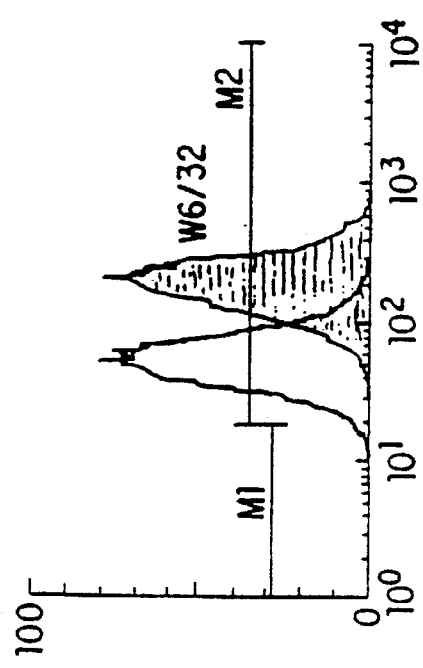
Figure 21:
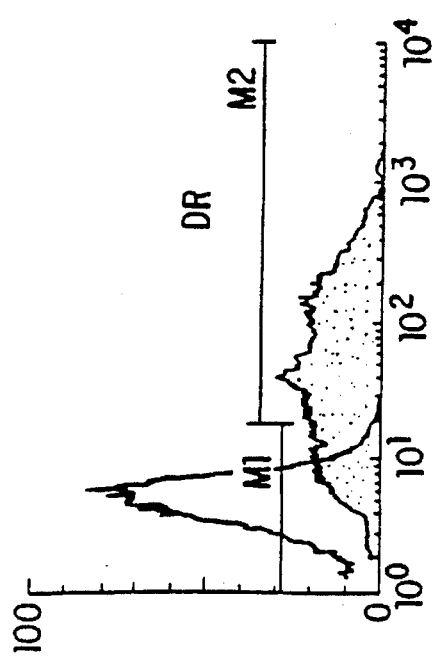

Evidence that the instant phenylacetic acid or phenylacetic acid derivative compositions can activate dormant gene and enhance expression of surface antigens is given by FIG. 21, which shows enhanced expression of MHC Class I, MHC Class II and the adhesion molecule ICAM-1 in melanoma cells that have been treated for 10 days with 2 mM NaPB (e.g., note the shift of the population mean from approximately 50 to 200 for MHC class I).

Furthermore, it has now been discovered that PB induces expression of EBV's latent membrane protein (LMP) in Burkitt's lymphoma cells. Cytoplasmic RNA (20 µg/lane) was isolated from LandisP, RajI and P3HRI Burkitt's lymphoma cell lines, which had been treated with 2 mM PB for four days, and subjected to Northern blot analysis with a specific LMP probe. In all three cell lines, a positive reaction was observed compared to controls (untreated cells), indicating that PB induces the expression of EBV's latent membrane protein. In Burkitt's lymphoma cells both PA and PB cause additional molecular and cellular changes, including cytostasis, decline in myc expression and enhancement of HLA+1.

Because these surface antigens enhance tumor immunogenicity in vivo, treatment of the animal (human) with PA, PB or their derivatives can enhance the effectiveness of the immune system of the individual. Doses of approximately 0.5–3.0 mM PB or equipotent doses of pharmaceutically acceptable phenylacetic acid derivatives may be useful. This treatment can also be combined with conventional immunotherapy treatments and/or antigen targeted, antibody-mediated chemotherapy. While treatment usually is accomplished by a protocol which allows for substantially continuous treatment, discontinuous or pulsed treatment protocols are also effective, especially for cells capable of terminally differentiating upon treatment with PAA or a PAA derivative. For instance, treatment of the melanoma cells given in FIG. 21 for 10 days was sufficient to allow continued enhanced expression of the surface antigens past this 10 day period.

Section H: Method of Monitoring the Dosage Level of Phenylacetic Acid or its Derivatives in a Patient and/or the Patient Response to these Drugs As discussed above, administration of phenylacetic acid or a derivative of phenylacetic acid such as NaPA or NaPB to an animal (human) in amounts and over treatment courses as described herein induce a variety of molecular changes. These molecular traits can be used as biomarkers to either (1) monitor the dosage level of the drug or its bioavailability in the animal and/or (2) serve as a biomarker of the patient response to the drug. For instance, as described above, administration of an effective amount of NaPA or NaPB (or their derivatives) results in a variety of molecular effects, including a) increased levels of fetal hemoglobin in erythrocytes; b) increased production of TGF-α in various cells such as those of melanocytic origin, astrocytic lineage or epithelial cell types; c) inhibition of the production of IL-6; and d) inhibition of the production of TGF-β2. Thus, absolute or relative (before/after treatment) concentrations of a particular biomarker can be determined in an appropriate cell population of the individual to allow monitoring of the dosage level or bioavailability of the drug. Further, this concentration can be correlated or compared with patient responses to develop a patient response scale for a desired treatment goal based upon that biomarker. For instance, the increased amount of fetal hemoglobin can be used to indicate the bioavailability of PA or PB for treatment or prevention of a neoplastic condition as well as indicating the degree of patient response to the drug.

Section I: The Activation of the PPAR by Phenylacetic Acid and its Derivatives

Peroxisomes are cellular organelles that contain enzymes which control the redox potential of the cell by metabolizing a variety of substrates such as hydrogen peroxide. Recent advances in this area reveal that peroxisomes can be proliferated through activation of a nuclear receptor which regulates the transcription of specific genes (Gibson, Toxicol. Lett., 68(1–2):193(1993)). This nuclear receptor has been named the peroxisome proliferator-activated receptor (PPAR) and belongs to the steroid nuclear receptors family that have a major effect on gene expression and cell biology. Binding by peroxisome proliferators such as clofibrate, herbicides, and leukotriene antagonists with PPAR activates the nuclear receptor, which acts as a transcriptional factor, and can cause differentiation, cell growth and proliferation of peroxisomes. Although these agents are thought to play a role in hyperplasia and carcinogenesis as well as altering the enzymatic capability of animal cells, such as rodent cells, these agents appear to have minimal negative effects in human cells, as exemplified by the safety of drugs such as clofibrate (Green, Biochem. Pharm. 43(3):393(1992)).

Figure 22:
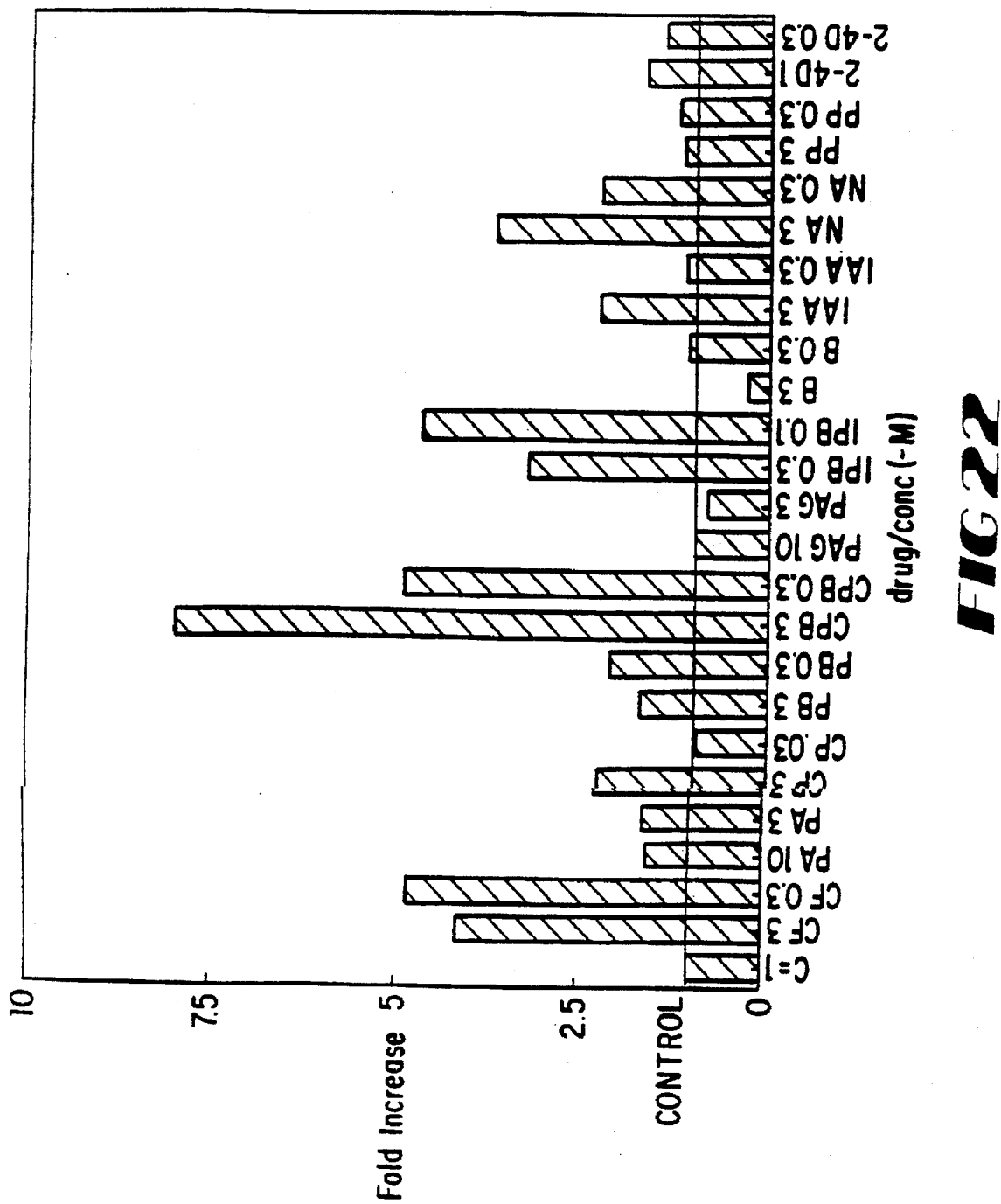
FIG. 22 shows the activation of the Peroxisomal Proliferator Receptor (PPAR) by PA, PB and various phenylacetic acid analogs. The activation is measured by the increased production of the indicator gene for cloramphenicol acetyl transferase (CAT), which is controlled by the response element for acyl-CoA oxidase, relative to the control (C). The experimental details for this activation measurement method can be found in Sher et al., *Biochem.*, 32(21):5598 (1993)). The concentration (in mM) of a particular drug is noted next to the following symbols for the various drugs: CF=clofibrate, PA=phenylacetate, CP=chlorophenylacetate, PB=phenylbutyrate, CPB=chlorophenylbutyrate, PAG= phenylacetylglutamine, IPB=iodophenylbutyrate, B=butyrate, IAA=indole acetic acid, NA=naphthylacetate, PP=phenoxypropionic acid, 2–4D=2,4-dichlorophenoxy acetate.

Peroxisome proliferators typically contain a carboxylic functional group. Therefore, PA, PB and various phenylacetic acid derivatives were tested for their ability to activate the PPAR and compared with known peroxisomal proliferators. As shown in FIG. 22, Clofibrate, a known activator of peroxisosmal proliferation, caused a 4- to 5-fold increase in activation as measured by increased production of the response element for acyl-CoA oxidase, which is the rate limiting enzyme in beta-oxidation and is contained in peroxisomes (Dreyer et al., Biol. Cell, 77(1):67(1993)). PA and PB caused mild activation (double baseline activity), naphthyl acetate was relatively more active (approximately 2.5- to 4-fold increase) while the halogenated analogs of PB were very potent stimulators. Interestingly, butyrate was not a significant peroxisomal proliferation activator.

The peroxisome proliferator-activated receptor has been shown to belong to the same family of nuclear receptors as the retinoid, thyroid and steroid receptors and PPAR is known to interact with RXR, the receptor of 9-cis-retinoic acid (a metabolite of all-trans-retinoic acid). Because the PPAR signaling pathway converges with the 9-cis retinoid receptor signal, it can be anticipated that retinoic acid or the like will significantly enhance the activity of PA or PB or other phenylacetic acid derivatives of this invention. Indeed, enhancement of the induction of HL-60 cell differentiation by NaPA in combination with retinoic acid is discussed above. Additionally, this synergistic response has been confirmed in other tumors, such as neuroblastoma, melanoma and rhabdomyosarcoma cells.

Thus, combination therapy consisting of administration (simultaneously in the same dosage form or simultaneously/sequentially in separate dosage forms) of Vitamin A, Vitamin D, Vitamin C, Vitamin E, B-carotene, or other retinoids and the like with PA, PB or other phenylacetic acid derivatives is encompassed by the instant invention for any of the treatment regimes given herein. Appropriate doses of the phenylacetic acid derivatives include approximately 0.5–10 mM PA, more preferably 0.5–5 mM PA, doses or equipotent doses of a pharmaceutically acceptable phenylacetic acid derivitive. Between 0.1 and 1.0 µM concentrations of the retinoids are expected to be effective. This combination therapy enhances, for instance, the efficacy of treatment with PA, PB or other phenylacetic acid derivatives, taken alone, for cancer, anemia and AIDS treatment, wound healing, and treatment of nonmalignant disorders of differentiation.

Figure 23:
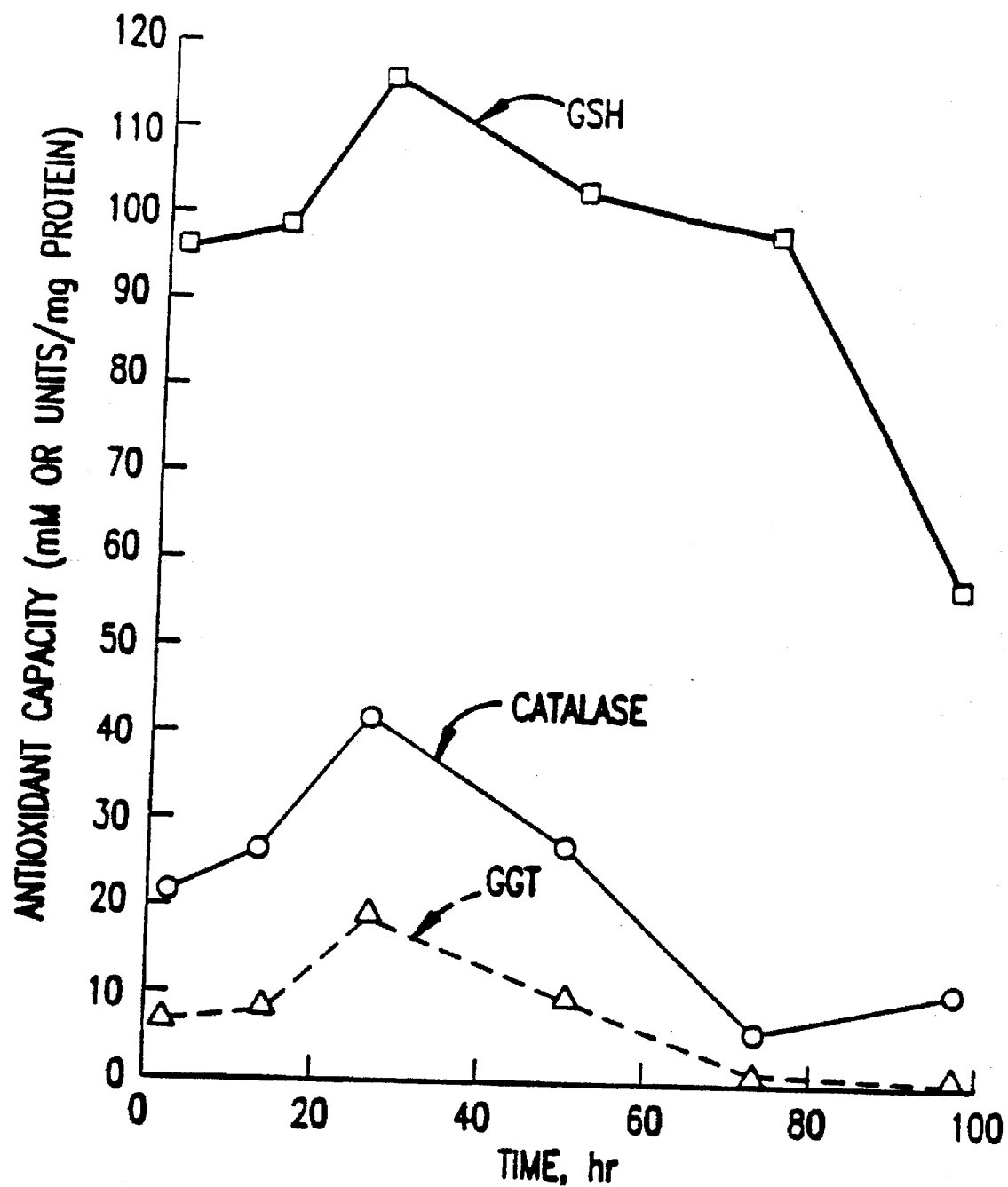
FIG. 23 shows the modulation by phenylbutyrate of glutathione (GSH), gamma-glutamyl transpeptidase (GGT) and catalase activites. The antioxidant capacity (mM or units/mg protein) of the enzymes were measured for up to approximately 100 hours following treatment of prostatic PC3 cells with 2 mM NaPB.

Agents affecting cellular peroxisomes have a major impact on oxidative stress and the redox state of a cell. Thus, further evidence that PA, PB or other phenylacetic acid derivatives activate PPAR can be found by the rapid increase of gamma glutamyl transpeptidase and catalase following cellular exposure to PA or PB as shown in FIG. 23. These antioxidant enzymes, whose activities are increased when peroxisome proliferation has been activated, were increased by 100% 24 hours after administration of sodium phenylbutyrate. This effect was reversed by approximately 48 hours and activity was maintained below control levels through 100 hours. The intracellular level of glutathione followed a similar biphasic pattern with an initial increase (20%) followed by a fall to levels below baseline at 100 h. The rapid induction with subsequent sharp decline of these antioxidant enzymes was observed in numerous tumor types from prostatic, breast and colon adenocarcinomas, osteosarcoma, and brain tumors. Molecular analysis showed changes in the rate of gene transcription of the GSH-related and antioxidant enzymes, which are consistent with activation of PPAR by PA, PB or their analogs.

Figure 24:
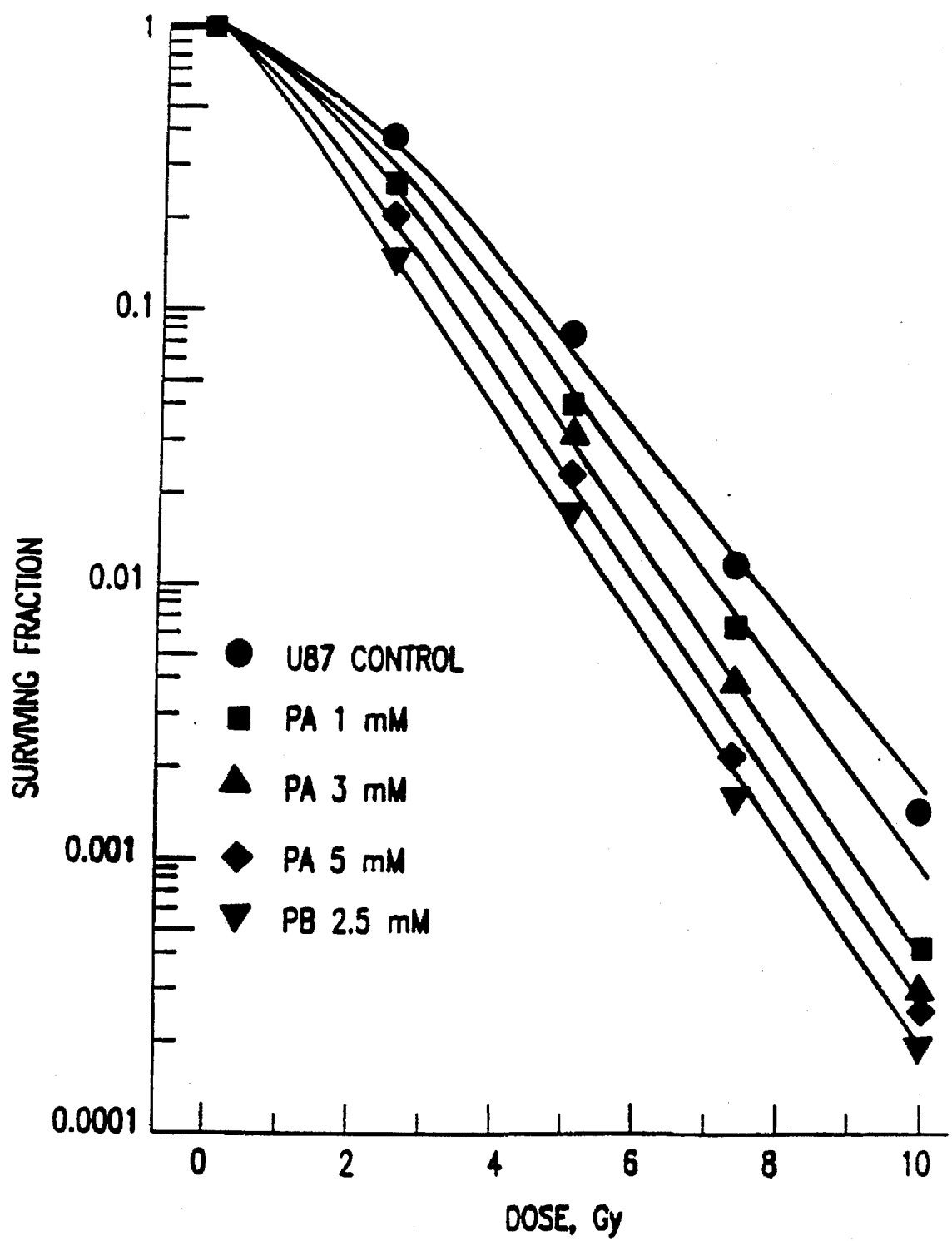
FIG. 24 shows the radiosensitization by PA and PB of human glioblastoma U87 cells by pretreatment for 72 hours with 1, 3 and 5 mM PA and 2.5 mM PB prior to exposure to ionizing radiation (Co⁶⁰ λ-radiaition).

Because peroxisomal enzymes are instrumental in defending against oxidative stress, experiments were undertaken to examine the effects of treatment with PA or PB on cells which were subjected to chemical or radiation stress. Pretreatment of glioblastomas (FIG. 24), breast carcinoma and metastatic prostate cells with a non-toxic dose of PA or PB 72 hours prior to $CO^{60}$ $\lambda$-radiation or treatment with adriamycin demonstrated a significant dose-related increase in cell killing by either modality. The surviving fraction of cells following drug treatment was nearly one tenth the fraction surviving with no pretreatment, which suggests that PA, PB or other like analogs could be used to increase the efficacy of radiation therapy and chemotherapy substantially. As such, the instant invention encompasses combination anti-cancer therapy consisting of administration of an non-toxic effective amount of phenylacetic acid or a pharmaceutically acceptable phenylacetic acid derivative (according to any of the dosage concentration protocols given herein) in combination with radiation therapy, particularly local treatment, or chemotherapy, particularly targeted to the tumor cells. This adjuvant therapy can be administered, for instance, after approximately 24 hours, such as from 24 hours to 120 hours or more, from the initiation of the administration of the derivative.

These results suggest a further consideration of a variety of pathogenic disorders. Inflammatory response to tissue injury, pathogenesis of emphysema, ischemia-associated organ injury (shock), doxorubicin-induced cardiac injury, drug-induced hepatotoxicity, atherosclerosis, and hyperoxic lung injuries are each associated with the production of reactive oxygen species and a change in the reductive capacity of the cell. Although long-term exposure to PA or other phenylacetic acid analogs depletes cellular redox protection systems, short term treatment with PA and the like may have significant implications for treatment of disorders associated with increased reactive oxygen species.

Section J: Use of Phenylacetic Acid and its Derivatives in Treatment of Cancers Having a Multiple-Drug Resistant Phenotype In treating disseminated cancers, systemic treatment with cytotoxic agents is frequently considered the most effective treatment. However, a number of cancers exhibit the ability to resist the cytotoxic effects of the specific antineoplastic drug administered as well as other agents to which the patient's system has never been exposed. In addition, some cancers appear to have multiple drug resistance even prior to the first exposure of the patient to an antineoplastic drug. Three mechanisms have been proposed to explain this phenomenon: P-glycoprotein Multiple Drug Resistance (MDR), MDR due to Topoisomerase Poisons and MDR due to altered expression of drug metabolizing enzymes (Holland et al., *Cancer Medicine*, Lea and Febiger, Philadelphia, 1993, p. 618–622).

P-glycoprotein MDR resistance appears to be mediated by the expression of an energy-dependent pump which rapidly removes cytotoxic agents from the cell. High levels of p-glycoprotein are associated with amplification of the MDR gene and transcriptional activation. Increased expression of p-glycoprotein can also be stimulated by heat shock, heavy metals, other cytotoxic drugs and liver insults, and ionizing radiation in some cell lines from some species. The results are not sufficiently consistent to confirm a causal relationship but are highly suggestive.

Topoisomerases are nuclear enzymes which are responsible for transient DNA strand breaks during DNA replication, transcription and recombination. Cytotoxic agents, such as etoposide, doxorubicin, amsacrine and others are known poisons of topoisomerase II, and cause lethal DNA strand breakage by the formation of stable complexes between the DNA, topoisomerase II and drug. MDR to this type of drug is thought to be caused by changes in the nature and amount of enzymatic activity, which is thought to prevent the formation or effect of the DNA-enzyme-drug complex.

Some cytotoxic agents are able to induce increased metabolic capability which permits rapid elimination of the toxin. Among the enzymes which have been implicated are glutathione S-transferase isozymes (GSTs). These enzymes are responsible for the conjugation of the electrophilic moieties of hydrophobic drugs with glutathione, which leads to detoxification and elimination of the drug.

Figure 25:
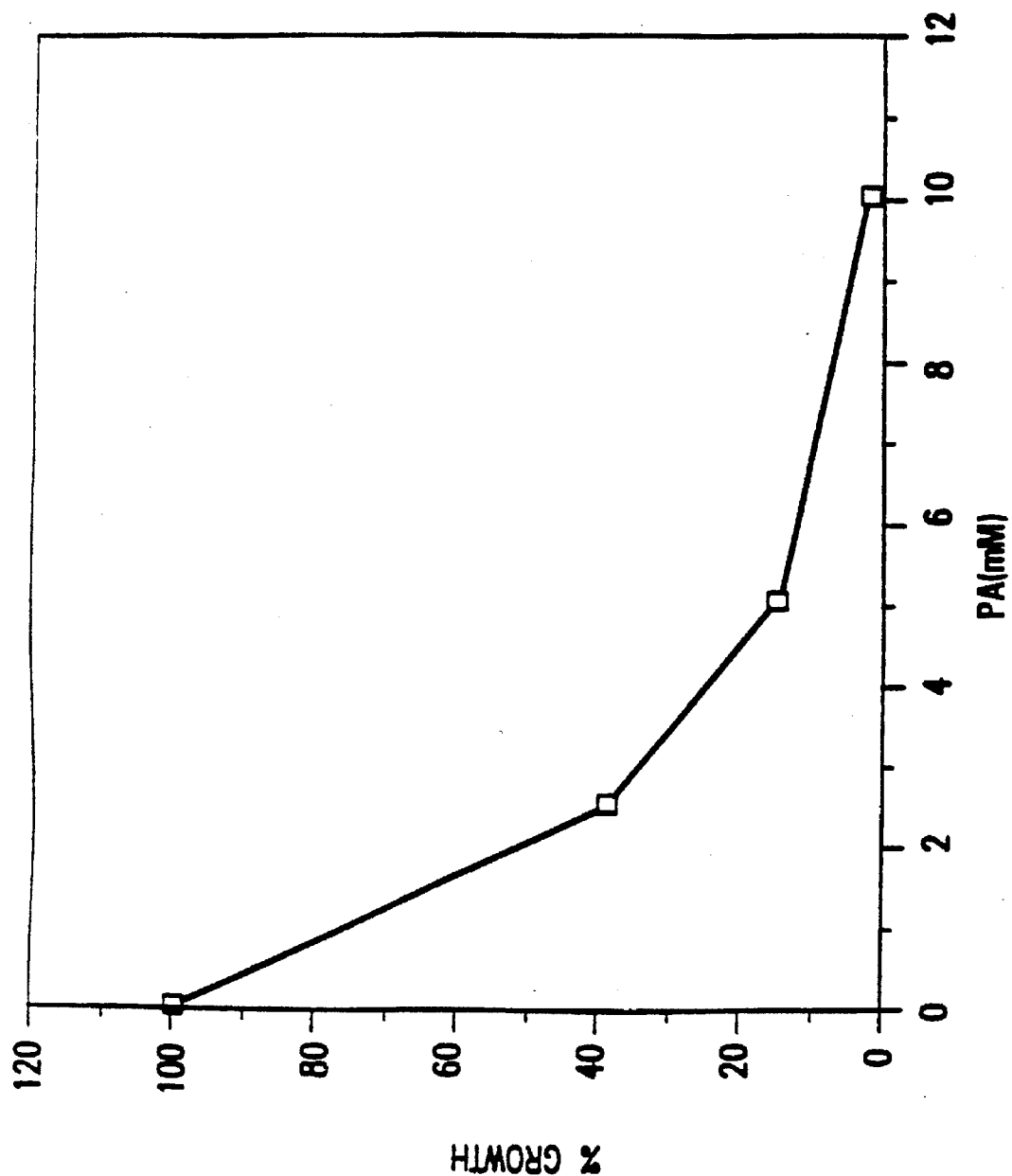
FIG. 25 shows the inhibition of the growth of breast MCF-7 adriamycin-resistant cancer cells by continuous exposure of up to 10 mM PA for 4 days.

As discussed above, PA and other phenylacetic acid analogs have been shown to stimulate the proliferation of peroxisomes which contain some isozymes of GST. Based on that observation, it would be expected that PA and PB would also stimulate MDR. However, as shown in FIG. 25, it has now been discovered that the opposite occurs. Thus, FIG. 25 shows the inhibition by PA of the growth of cells from a line of breast cancer cells that exhibit the MDR phenotype. Up to 10 mM PA in cultures, growth of cells is dramatically inhibited in a dose-dependent manner. Surprisingly, PA and PB are more highly active against adriamycin-resistant breast cancer cells than compared to adriamycin-sensitive cells. This increased sensitivity of the MDR phenotype is reproducible in other tumor models, including those that are resistant to radiation therapy.

Thus, the instant invention provides a method of treating tumor cell populations in a patient that are resistant or able to survive current conventional treatments, particularly tumors having a MDR phenotype, by administration to the patient of non-toxic amounts of PA (such as amounts that provide up to 10 mM PA or an equipotent dose of a pharmaceutically acceptable phenylacetic acid derivative) in the vicinity of the tumor or equivalently effective amounts of phenylacetic acid or a phenylacetic acid analog. PA or other analog dosage protocols similar to those described in relation to the potentiation of differentiation in tumor cells by these phenylacetic acid-related compounds, including the various combination therapies described herein, can be used to treat patients with resistant tumors such as MDR tumors. Long-term (weeks, months) or short-term (day(s)) substantially continuous treatment regimens (including continuous administration or frequent administration of separate doses) as well as pulsed regimens (days, weeks or months of substantially continuous administration followed by a drug-free period) can beneficially be employed to treat patients with MDR tumors.

Section K: Phenylacetate and its Derivatives, Correlation Between Potency and Lipophilicity One potential problem that could hinder the clinical use of phenylacetate is related to the large amounts of drug required to achieve therapeutic concentrations, i.e., over 300 mg/kg/day. Studies were thus undertaken to develop analogs that are effective at lower concentrations. Studies in plants revealed that increasing the lipophilicity of a phenylacetate analogue (as measured by its octanol-water partition coefficient) enhanced its growth-regulatory activity [Muir, R. M., Fujita, T., and Hansch, C. Structure-activity relationship in the auxin activity of mono-substituted phenylacetic acids. *Plant Physiol.*, 42: 1519–1526, 1967.]. Calculated partition coefficient (CLOGP) was used to correlate the predicted lipophilicity with the measured antitumor activity of phenylacetate analogues. For these analogues, enhanced potency in inducing cytostasis and phenotypic reversion in cultured prostate carcinoma, glioblastoma, and melanoma cells was correlated with increased drug lipophilicity.

Cell Cultures. Studies included the following humans tumor cell lines: (a) hormone-refractory prostatic carcinoma PC3, DU145, purchased from the American Type Culture Collection (ATCC, Rockville, Md.); (b) glioblastoma U87, A172 (ATCC); (c) melanoma A375 and mel 1011, provided by J. Fidler (M. D. Anderson, Houston Tex.) and J. Weber (NCI, Bethesda Md.), respectively. Cells were maintained in RPMI 1640 supplemented with 10% heat inactivated fetal calf serum (Gibco Laboratories), antibiotics, and 2 mM L-glutamine. Diploid human foreskin FS4 fibroblasts (ATCC), and human umbilical vein endothelial cells (HUVC) were used for comparison. The HUVC cells, isolated from freshly obtained cords, were provided by D. Grant and H. Kleinman (NIH, Bethesda Md.).

Antitumor Agents. Sodium phenylacetate and phenylbutyrate were from Elan Pharmaceutical corp, Gainvesville Ga. 4-Iodophenylacetate, 4-iodophenylbutyrate and 4-chlorophenylbutyrate were synthesized by the Sandmeyer procedure from the corresponding 4-amino-phenyl-fatty acids. The halogenated products were extracted from the acidic reaction mixtures with diethyl ether which was then taken to dryness. The residue was dissolved in boiling hexane and the crystals that formed on cooling were collected by suction filtration. The product was recrystallized from hexane until the reported melting points were obtained. Amides of phenylacetate and phenylbutyrate were produced by heating the sodium salts with a small excess of thionylchloride followed by the addition of ice-cold concentrated ammonia. The amides were purified by recrystalization from boiling water. The identity of synthesized compounds was verified by melting point determination and by mass spectroscopy. All commercially available derivatives were purchased from Aldrich (Milwaukee, Wis.) or Sigma (St. Louis, Mo.), depending on availability. Tested compounds were all dissolved in distilled water, brought to pH 7.0 by the addition of NaOH as needed, and stored in aliquots at −20° C. till used.

Calculation of Relative Drug Lipophilicities. Estimation of the contribution of lipophilicity to the biological activity of a molecule was based on its calculated logarithm of octanol-water partition coefficient (CLOGP). This was determined for each compound using the BLOGP program of Bodor et al., (BLOGP version 1.0, Center for Drug Discovery, University of Florida) assuming that the degree of ionization is similar for all tested compounds.

Quantitation of Cell Growth and Viability. Growth rates were determined by cell enumeration with a hemocytometer following detachment with trypsin-EDTA, and by an enzymatic assay using 3-[4,5-dimethylthiazol-2-yl]-2,5-diphenyltertrazolium bromide (MTT). These two assays produced essentially the same results. Cell viability was assessed by trypan blue exclusion.

Colony Formation in Semi-Solid Agar. For analysis of anchorage independent growth, cells were harvested with trypsin-EDTA and resuspended at $1.0 \times 10^4$ cells per ml in growth medium containing 0.36% agar (Difco). Two ml of cell suspension were added to 60 mm plates (Costrar) which were pre-coated with 4 ml of solid agar (0.9%). Tested drugs were added at different concentrations, and colonies composed of 30 or more cells were counted after 3 weeks.

Growth on Matrigel. Cells were first treated with drugs in T.C. plastic dishes for 4–6 days, and then replated ($5 \times 10^4$ cells per well) onto 16 mm dishes (Costar, Cambridge, Mass.) coated with 250 ul of 10 mg/ml matrigel, a reconstituted basement membrane (Collaborative Research). Drugs were either added to the dishes or omitted in order to determine the reversibility of effect. Net-like formation characteristic of invasive cells occurred within 12 hours, while invasion into the matrigel was evident after 6–9 days.

Drug Uptake Studies. Cells were plated in 6-well T.C. dishes (Costar) at $5 \times 10^5$ cells per dish. The growth medium was replaced after 24 hrs with 750 ul of fresh medium containing $4.5 \times 10^5$ DPM of either $^{14}$C-phenylacetic acid (3.4 mCi/mmmol, Sigma) or $^{14}$C-naphthylacetic acid (5.4 mCi/mmol, Sigma), and the cultures were incubated for 10–180 minutes at 37° C. Labeling was terminated by placing plates on ice. Cells were then washed twice with 5 ml ice-cold phosphate buffer saline (PBS), detached by scraping, and the radioactivity retained by cells determined using liquid scintillation. Blank values were determined by incubating the radiolabled compounds in an empty dish.

Correlation Between Drug Lipophilicity and Growth-Inhibitory Effect of Phenylacetate and its Analogues. The growth inhibitory effect of these compounds on prostatic carcinoma, glioblastoma, and melanoma cell lines are expressed as $IC_{50}$ and correlated with drug lipophilicity determined using the CLOGP program. As seen in Tables 21 and 22, there is a good correlation between cytostasis and lipophilicity. In agreement with previous observations with phenylacetate (3), the cytostatic effect was selective as higher drug concentrations were needed to significantly affect the proliferation of normal endothelial cells and skin fibroblasts. No cytotoxicity (i.e., decline in cell viability) occurred during 4–6 days of continuous treatment with the tested compounds.

TABLE 21

Phenylacetate and analogues containing alkyl-chain substitutions: Relationship of $IC_{50}$ to CLOGP

| | | $IC_{50}$ (mM) | | | |
|---|---|---|---|---|---|
| Rx | CLOGP | prostate ca. | glioblastoma | melanoma | normal cells |
| α-methoxy-PA | 2.17 | 6 | 5.8 | 6 | ND |
| PA | 2.05 | 5 | 4.3 | 5 | 12 |
| α-methyl-PA | 2.42 | 2.6 | 3.8 | 3.5 | 12 |
| α-ethyl-PA | 2.77 | 2.1 | 2.8 | 2.2 | 9 |
| PB | 2.89 | 1 | 1.8 | 1 | ND |
| 4-chloro-PB | 3.30 | 0.75 | ND | 0.8 | ND |
| 4-iodo-PB | 3.85 | 0.36 | 0.27 | 0.22 | ND |

ND, not determined

TABLE 22

Phenylacetate and analogues containing ring substitutions: Relationship of $IC_{50}$ to CLOGP

| | | $IC_{50}$ (mM) | | | |
|---|---|---|---|---|---|
| Rx | CLOGP | prostate ca. | glioblastoma | melanoma | normal cells |
| 4-hydroxy-PA | 1.78 | 7.5 | 10 | 10 | ND |
| PA | 2.05 | 5 | 4.3 | 5 | 12 |
| 4-fluoro-PA | 2.17 | 2.8 | 4 | 2.5 | ND |
| 2-methyl-PA | 2.43 | 2.5 | ND | ND | ND |
| 3-methyl-PA | 2.45 | 2.1 | ND | ND | ND |

TABLE 22-continued

Phenylacetate and analogues containing ring substitutions: Relationship of $IC_{50}$ to CLOGP

| | | $IC_{50}$ (mM) | | | |
|---|---|---|---|---|---|
| Rx | CLOGP | prostate ca. | glioblastoma | melanoma | normal cells |
| 4-methyl-PA | 2.47 | 2.1 | ND | ND | ND |
| 4-chloro-PA | 2.48 | 1 | 0.9 | 1.2 | 3 |
| 3-chloro-PA | 2.54 | 1.75 | 1.7 | 1.5 | 7 |
| 2-chloro-PA | 2.56 | 2.4 | 2.1 | 2.5 | ND |
| 2,6-dichloro-PA | 2.87 | 1 | 0.8 | 1 | ND |
| 4-iodo-PA | 3.12 | 0.6 | 0.9 | 1.2 | ND |
| 1-naphtylacetate | 3.16 | 0.8 | 0.9 | 0.8 | 2.8 |

ND, not determined

Figure 27A:
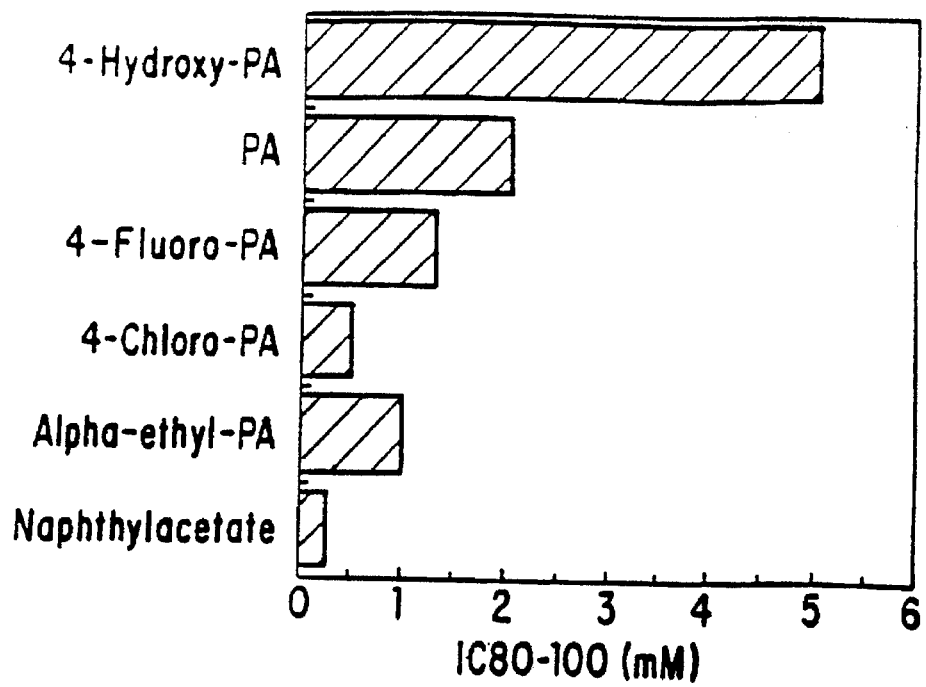
FIGS. 27A and 27B show the phenotypic reversion induced by phenylacetate and selected derivatives. The malignant prostatic PC3 cells were treated as described in "Material and Methods". Data indicates the relative potency of tested compounds in significantly inhibiting PC3 anchorage-independence (A) and completely blocking matrigel invasion (B). Phenylacetate and analogs are presented in an increasing order of CLOGP (top to bottom). CLOGP values are provided in Tables 21 and 22. The effect on anchorage-dependency was confirmed with U87 cells (not shown).
Figure 27B:
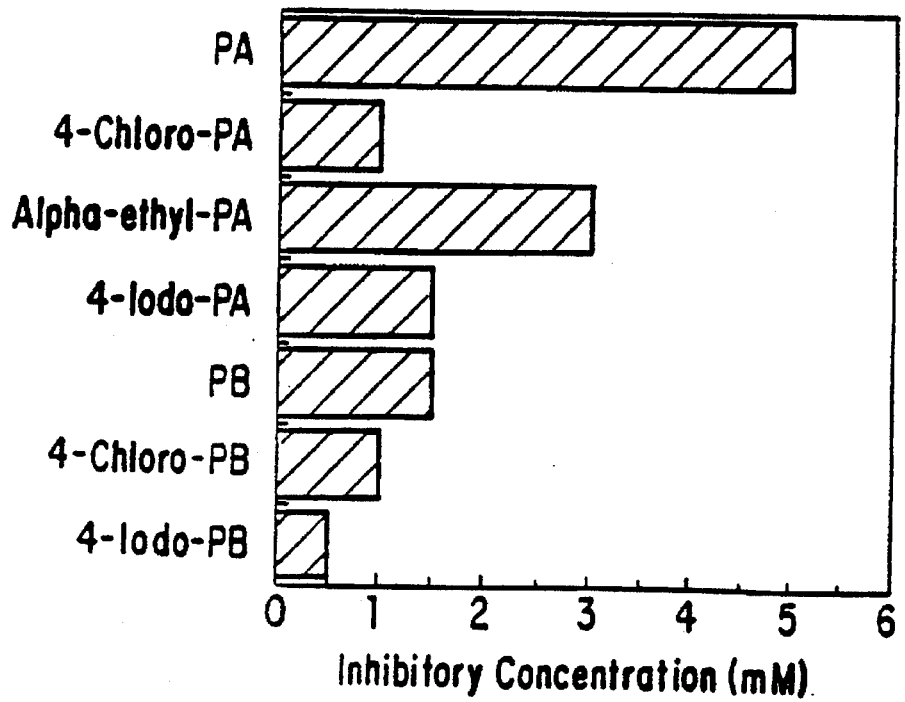

Further analysis of structure-activity relationships was based on the method of Hansch and Anderson used for the correlation of the anesthetic and metabolic effects of barbiturates with their octanol-water partition coefficients [Hansch, C., and Anderson, S. M. The structure-activity relationship in barbiturates and its similarity to that in other narcotics. *J. Med. Chem* 10: 745–753, 1967.]. Adaptation of this method assumes that, if the relationship is simple, it will follow the equation: log 1/C=slope log P+K. Plotting the log $1/IC_{50}$ values obtained with prostatic cells vs drug CLOGP (FIG. 26) shows that the best fit line is described by the equation: log $1/IC_{50}$=0.89 CLOGP+0.55. The slope of this line (0.89) is in the range of values found for the anesthetic potencies of a series of barbiturate analogues. Hansch and colleagues also studied the effect of phenylacetate and its derivatives on plant growth. As shown in FIG. 27, the concentration range and rank order of inhibition of plant growth by phenylacetate analogues are comparable to the inhibition of growth of prostatic cancer cells by this same series of compounds.

While the overall trend of enhanced activity of phenylacetate derivatives with increased lipophilicity is clear, some small deviations occur. For both chloro- and methyl-substitutions, the para position is more potent than the ortho position. In addition, and despite their near equal contributions to lipohilicity, para chloro-substitution was more potent than methyl. In contrast to derivatives containing ring or alpha-carbon substitutions, those with blocked carboxyl groups exhibited a decline in cytostatic activity. The methyl ester of phenylacetate was about half as active than the free acid ($IC_{50}$ in DU145 prostatic cells 8.8 mM versus 4.1 mM for phenylacetate). The amide forms were also less active than the parent compounds in this experimental system, with $IC_{50}$ of 2.0 mM for phenylbutyramide versus 1.2 mM for phenylbutyrate, and 4.8 mM for phenylacetamide versus 4.1 mM for phenylacetate.

Drug Uptake. One possible function of increasing lipophilicity is an increasing ease with which aromatic fatty acids can enter into, and cross the plasma membrane as well as the membranes of other organelles. The rate of phenylacetate uptake by tumor cells was compared that of the more hydrophobic analog, naphthylacetate (Table 22). After 10 minutes, relative to phenylacetate more than twice as much naphthylacetate had entered the glioblastoma U87 cells (uptake of phenylacetic acid was 41% that of naphthylacetic acid) indicating that its movement through the plasma membrane was more than twice as fast as phenylacetate. After 20 minutes, the amount of naphthylacetate taken up by the cells was as only 26% greater than that of phenylacetate and at 180 minutes the intracellular levels of both compounds were nearly equal, suggesting that at this time the more rapid influx of naphthylacetic acid was balanced by an equally rapid efflux. There was little further uptake and the concentration of phenylacetate inside and outside the cells was about equal indicating that these cells do not actively accumulate much aromatic fatty acid.

Phenotypic Reversion. In addition to causing selective cytostasis, phenylacetate induces malignant cells to undergo reversion to a more benign phenotype. The effect of analogs on tumor biology was tested using as a model the hormone-refractory prostatic PC3 cells originally derived from a bone metastasis. PC3 exhibit several growth characteristics in vitro that correlate with their malignant behavior in vivo, including anchorage-independent growth (i.e., colony formation in semi-solid agar), and formation of "net"-like structures when plated on a reconstituted basement membrane (matrigel). The ability of phenylacetate and representative analogs to bring about loss of such properties is summarized in FIG. 27. Similar to the cytostatic effect, drug ability to induce reversion to a non-malignant phenotype was highly correlated with the calculated lipophilicity of the drugs. Of the tested compounds, naphthylacetate, as well as derivatives of phenylbutyrate and phenylacetate with iodo- and chlorine substitutions were found to be the most active on a molar basis. The relative efficacy of the compounds in suppressing anchorage independent growth was confirmed using U87 glioblastoma cells (data not shown).

Discussion. The comparative activity of phenylacetate and its analogues against a number of tumor cell lines suggest that these compounds may form a new class of therapeutic agents whose effectiveness varies with structure. Improved anticancer activity is achieved if factors controlling their action are understood, and toward this end the effects of systematic changes in structure with changes in activity have been compared. The outstanding result is the discovery that: (a) there is a simple relationship between the lipophilicity of a phenylacetate derivative and its activity against human tumor cells, and (b) the relative potency observed with human neoplasms is similar to that documented in plants, indicating that the role of the aromatic fatty acids in growth regulation has been conserved in evolution.

The efficacy of aromatic fatty acids was demonstrated in vitro using tumor cell lines derived from patients with hormone-refractory prostatic carcinoma, glioblastomas, and malignant melanoma. Like phenylacetate, several derivatives containing alpha-carbon or ring substitutions all induced cytostasis and phenotypic reversion at non-toxic concentrations. Changes in tumor biology included reduction in cell proliferation rate and loss of malignant properties such as invasiveness and anchorage-independence. There were, however, significant differences in potency. When compared to phenylacetate, analogs with naphthyl-, halogen- or alkyl-ring, as well as α-carbon alkyl substitutions exhibited increased activity, while those with α-methoxy or hydroxyl replacement at the phenyl ring were less effective. Drug potency was correlated with the degree of calculated lipophilicity, indicating that differences in efficacy may be due in part to the ease with which these agents enter into and cross the lipid bilayer of cell membranes. In agreement, uptake of the more hydrophobic compound, naphthylacetate, was significantly faster than that of phenylacetate. At equilibrium (about 180 minutes for phenylacetate), however, there were no differences in either the total intracellular concentration of both compounds, or the levels inside and outside cells. These results suggest that the rates of drug uptake are balanced by proportional rates of efflux, and that the overall capacity of the cell to retain such compounds is not much greater than that of the extracellular milieu.

Although there is a good correlation between drug potency and lipophilicity (see FIG. 26), small deviations within the phenylacetate-related series may give some clues regarding mechanisms of action. Halogen substitutions para to the alkylcarboxyl group were found to increase potency more than those in the ortho position, suggesting that orientation of the hydrophobic substituent may be important. At the para position, chlorine had a greater impact on efficacy than a methyl group despite nearly equal contributions to CLOGP, indicating that electronegativity may affect growth inhibitory interactions. While $\alpha$-ethylphenylacetic acid, in which the carboxyl group is crowded by the adjacent ethyl group, was more potent than the parent compound, the more lipophilic analog $\alpha$-methoxyphenylacetic acid was less active. The $\alpha$-methoxyphenylacetic acid is a significantly stronger acid, and this greater acidity could be important. Other parameters such as addition of an aromatic ring to phenylacetate, or an increase in the distance between the aromatic nucleus and the carboxyl group did not cause anomalous enhancement or interference in biological activity (naphthylacetate and phenylbutyrate were about as active as would be expected on the basis of their lipophilicity). The importance of a free carboxyl group is unclear. The amide forms of phenylacetate and phenylbutyrate, in which the carboxylic group is blocked, were less cytostatic compared to the parental compounds and failed to induce cell differentiation (unpublished data). Moreover, phenylacetyl-glutamine has no detectable effect on cell growth and maturation. It appears, therefore, that a free carboxyl group may be essential for some aspects of the antitumor activity of phenylacetate and derivatives.

The correlation between partition coefficients and bioactivity of the aromatic fatty acids is reminiscent of that observed for a large number of other lipophilic agents. A survey by Hansch and Anderson revealed that, in a variety of animal tissues, the anesthetic and metabolic effects of barbiturates corresponded well with their hydrophilicity, having an average slope of about 1 compared to a slope of about 0.67 for lipophilic interaction with protein. It was concluded that the critical step in initiating biological activity was entry into the lipid bilayer, probably followed by interaction with membrane proteins. Some of the subsequently identified targets of barbiturates are indeed, membrane proteins and these include the GABA receptor-chloride in neurons, the ATP-$K^+$ pump in pancreatic B-cells, and the G-protein that stimulates PLC activity in leukemic cells.

Despite a wide body of literature implicating phenylacetate and analogs in growth control throughout phylogeny, little is known regarding their mode of action. In plants, phenylacetate and naphtylacetate are endogenous growth hormones (auxins) known to stimulate proliferation at micromolar concentrations, while inhibiting growth at millimolar levels. As growth inhibitors (but not stimulators), the effect of phenylacetate analogues on rapidly developing embryonic plant tissues, like that on human tumor cells, is a simple function of their lipophilicities. These similarities in potency, summarized in FIG. 27, suggest that some of the underlying mechanisms of negative growth control may be similar as well.

There is accumulating evidence indicating that phenylacetate and derivatives may act through multiple mechanisms to alter gene expression and cell biology. At growth inhibitory concentrations, the aromatic fatty acids could alter the pattern of DNA methylation, an epigenetic mechanism controlling the transcription of various eukaryotic genes. Phenylacetate inhibits DNA methylation in plant and mammalian cells, and both phenylacetate and phenylbutyrate were shown to activate the expression of otherwise dormant methylation-dependent genes. DNA hypomethylation per se is not sufficient to induce gene expression. Preliminary findings indicate that phenylacetate, phenylbutyrate and several analogs activate a nuclear receptor that functions as a transcriptional factor; interestingly, the receptor is a member of a steroid nuclear receptor superfamily, the ligands of which are carboxylic acids and include well characterized differentiation inducers such as retinoids.

In addition to affecting gene transcription, the phenyl-fatty acids may interfere with protein post-translational processing by inhibiting the mevalonate (MVA) pathway of cholesterol synthesis. MVA is a precursor of several isopentenyl moieties required for progression through the cell cycle, and of prenyl groups that modify a small let of critical proteins. The latter include plasma membrane G and G-like proteins (e.g., ras) involved in mitogenic signal transduction (molecular weight 20–26 kDa), and nuclear envelope lamins that play a key role in mitosis (44–74 kDa). The aromatic fatty acids can conjugate with coenzyme-A, enter the pathway to chain elongation, and interfere with lipid metabolism in general. Furthermore, compounds such as phenylacetate can assume a conformation resembling mevalonate pyrophosphate and inhibit MVA utilization specifically. It was recently demonstrated that phenylacetate activity against poorly differentiated mammalian tissues (human glioblastoma cells and the developing fetal brain) is associated with inhibition of MVA decarboxylation and a decline in protein isoprenylation. Rapidly developing mammalian and plant tissues are highly dependent upon MVA for cell replication. Inhibition of MVA utilization by phenylacetate-related compounds could thus be responsible in part for their effect documented in such highly divergent organisms.

In conclusion, phenylacetate and analogs appear to represent a new class of pleiotropic growth regulators that might alter tumor cell biology by affecting gene expression at both the transcriptional and post transcriptional levels. Phenylacetate and phenylbutyrate have already been established as safe and effective in treatment of hyperammonemia, and phase I clinical trials in adults with cancer confirmed that millimolar levels can be achieved in the plasma and cerebrospinal fluid with no significant toxicities (discussed herein). However, rather large doses (300 mg/kg/day or more) are required to achieve potentially therapeutic levels. The identified relationship between lipophilicity of commercially available analogs and their antitumor activity in experimental models led us to predict that analogs with greater CLOGPs, e.g., iodo derivatives of phenylacetate and phenylbutyrate, would be highly effective. Indeed, these compounds were found to be the most potent aromatic fatty acids yet tested. With this approach, it should be possible to identify highly effective and safe antitumor agents suitable for clinical application.

Modes of Drug Administration

NaPA (or PAA derivatives) may be administered locally or systemically. Systemic administration means any mode or route of administration which results in effective levels of active ingredient appearing in the blood or at a site remote from the site of administration of said active ingredient.

The pharmaceutical formulation for systemic administration according to the invention may be formulated for intravenous, intramuscular, subcutaneous, oral, nasal, enteral, parenteral or topical administration. In some cases, a combination of types of formulations may be used simultaneously to achieve systemic administration of the active ingredient.

Suitable formulations for oral administration include hard or soft gelatin capsules, dragees, pills, tablets (including coated tablets), elixirs, suspensions, and syrups or inhalations.

Solid dosage forms in addition to those formulated for oral administration include rectal suppositories.

The compounds of the present invention may also be administered in the form of an implant.

Suitable formulations for topical administration include creams, gels, jellies, mucilages, pastes and ointments.

Suitable injectable solutions include intravenous, subcutaneous, and intramuscular injectable solutions. The compounds of the present invention may also be administered in the form of an infusion solution or as a nasal inhalation or spray.

The compounds of the present invention may also be used concomitantly or in combination with selected biological response modifiers, e.g., interferons, interleukins, tumor necrosis factor, glutamine antagonists, hormones, vitamins, as well as anti-tumor agents and hematopoietic growth factors, discussed above.

It has been observed that NaPA is somewhat malodorous. Therefore, it may be preferable to administer this compound in the presence of any of the pharmaceutically acceptable odor-masking excipients or as its precursor phenylbutyrate (or a derivative or analog thereof) which has no offensive odor.

The PAA and its pharmaceutically acceptable derivatives to be used as antitumor agents can be prepared easily using pharmaceutical materials which themselves are available in the art and can be prepared by established procedures. The following preparations are illustrative of the preparation of the dosage forms of the present invention, and are not to be construed as a limitation thereof.

Example 21

Parenteral Solution 1

A sterile aqueous solution for parenteral administration containing 200 mg/ml of NaPA for treating a neoplastic disease is prepared by dissolving 200 g. of sterilized, micronized NaPA in sterilized Normal Saline Solution, qs to 1000 ml. The resulting sterile solution is placed into sterile vials and sealed. The above solution can be used to treat malignant conditions at a dosage range of from about 100 mg/kg/day to about 1000 mg/kg/day. Infusion can be continuous over a 24 hour period.

Example 22

Parenteral Solution 2

A sterile aqueous solution for parenteral administration containing 50 mg/ml of NaPA is prepared as follows:

| Ingredients | Amount |
| --- | --- |
| NaPA, micronized | 50 g. |
| Benzyl alcohol | 0.90% w/v |
| Sodium chloride | 0.260% w/v |
| Water for injection, qs | 1000 ml |

The above ingredients, except NaPA, are dissolved in water and sterilized. Sterilized NaPA is then added to the sterile solution and the resulting solution is placed into sterile vials and sealed. The above solution can be used to treat a malignant condition by administering the above solution intravenously at a flow rate to fall within the dosage range set forth in Example 21.

Example 23

Parenteral Solution 3

A sterile aqueous solution for parenteral administration containing 500 mg/ml of sodium phenylbutyrate is prepared as follows:

| Ingredients | Amount |
| --- | --- |
| Sodium phenybutyrate | 500 g. |
| Dextrose | 0.45% w/v |
| Phenylmercuric nitrate | 0.002% w/v |
| Water for injection, qs | 1000 ml. |

The preparation of the above solution is similar to that described in Examples 21 and 22.

Example 24

Tablet Formulation 1

A tablet for oral administration containing 300 mg of NaPA is prepared as follows:

| Ingredients | Amount |
| --- | --- |
| NaPA | 3000 g. |
| Polyvinylpyrrolidone | 225 g. |
| Lactose | 617.5 g |
| Stearic acid | 90 g. |
| Talc | 135 g. |
| Corn starch | 432.5 g |
| Alcohol | 45 L |

NaPA, polyvinylpyrrolidone and lactose are blended together and passed through a 40-mesh screen. The alcohol is added slowly and the granulation is kneaded well. The wet mass is screened through a 4-mesh screen, dries overnight at 50° C. and screened through a 20-mesh screen. The stearic acid, talc and corn starch is bolted through 60-mesh screen prior to mixing by tubing with the granulation. The resulting granulation is compressed into tablets using a standard 7/16 inch concave punch.

Example 25

Tablet Formulation 2

A tablet for oral administration containing 200 mg of sodium phenylbutyrate is prepared as follows:

| Ingredients | Amount |
| --- | --- |
| Sodium phenylbutyrate | 2240 g. |
| Compressible sugar (Di-Pac) | 934 g. |
| Sterotex | 78 g. |
| Silica gel (Syloid) | 28 g. |

The above ingredients are blended in a twin-shell blender for 15 minutes and compressed on a 13/22 inch concave punch.

Example 26

Intranasal Suspension

A 500 ml sterile aqueous suspension is prepared for intranasal installation as follows:

| Ingredients | Amount |
| --- | --- |
| NaPA, micronized | 30.0 g. |
| Polysorbate 80 | 2.5 g. |
| Methylparaben | 1.25 g. |
| Propylparaben | 0.09 g. |
| Deionized water, qs 500 ml | |

The above ingredients, with the exception of NaPA, are dissolved in water and sterilized by filtration. Sterilized NaPA is added to the sterile solution and the final suspensions are aseptically filled into sterile containers.

Example 27

Ointment

An ointment is prepared from the following ingredients:

| Ingredients | Amount |
| --- | --- |
| NaPA | 10 g. |
| Stearyl alcohol | 4 g. |
| White wax | 8 g. |
| White petrolatum | 78 g. |

The stearyl alcohol, white wax and white petrolatum are melted over a steam bath and allowed to cool. The NaPA is added slowly to the ointment base with stirring.

Example 28

Lotion

| Ingredient | Amount |
| --- | --- |
| Sodium phenylbutyrate | 1.00 g. |
| Stearyl methylcellulose (4,500) Solution (2%) | 25.00 ml |
| Benzalkonium chloride | 0.03 g. |
| Sterile water | 250.00 ml |

The benzalkonium chloride is dissolved in about 10 ml. of sterile water. The sodium phenylbutyrate is dispersed into methylcellulose solution by means of vigorous stirring. The methylcellulose (4,500) used is a high viscosity grade. The solution of benzalkonium chloride is then added slowly while stirring is continued. The lotion is then brought up to the desired volume with the remaining water. Preparation of the lotion is carried out under aseptic conditions.

Example 29

Dusting Powder

| Ingredients | Amount |
| --- | --- |
| NaPA | 25 g. |
| Sterilized absorbable maize starch BP dusting powder | 25 g. |

The dusting powder is formulated by gradually adding the sterilized absorbable dusting powder to NaPA to form a uniform blend. The powder is then sterilized in conventional manner.

Example 30

Suppository, Rectal and Vaginal Pharmaceutical Preparations

Suppositories, each weighing 2.5 g. and containing 100 mg. of NaPA are prepared as follows:

| Ingredients | Amount/1000 |
| --- | --- |
| Suppositories | |
| NaPA, micronized | 100 g. |
| Propylene glycol | 150 g. |
| Polyethylene glycol 4000, qs | 2500 g. |

NaPA is finely divided by means of an air micronizer and added to the propylene glycol and the mixture is passed through a colloid mill until uniformly dispersed. The polyethylene glycol is melted and the propylene glycol dispersion added slowly with stirring. The suspension is poured into unchilled molds at 40° C. Composition is allowed to cool and solidify and then removed from the mold and each suppository is foil wrapped.

The foregoing suppositories are inserted rectally or vaginally for treating neoplastic disease.

It is known that intracellular glutathione plays a major role in detoxification and repair of cellular injury by chemical and physical carcinogens. NaPA treatment of normal or tumor cells markedly induced the activity of intracellular glutathione approximately 2–10-fold depending on growth conditions. Nontoxic agents that can induce glutathione are highly desirable since these are likely to protect cells from damage by a variety of chemical carcinogens and ionizing radiation.

Taken together, the present invention demonstrates that NaPA, NaPB and other PAA derivatives have valuable potential in cancer prevention in case such as high risk individuals, for example, heavy smokers with familial history of lung cancer, inherited disorders of concogene abnormalities (Li-Fraumeni syndrome), individuals exposed to radiation, and patients in remission with residual disease. Furthermore, these compounds can be used in combination with other therapeutic agents, such as chemicals and radiation, to enhance tumor responses and minimize adverse effects such as cytotoxicity and carcinogenesis. The antitumor activity, lack of toxicity, and easy administration qualify NaPA as a preferred chemopreventive drug.

I claim:

1. A method of preventing a neoplastic condition in a subject comprising administering a prophylactic amount of a compound of the formula I:

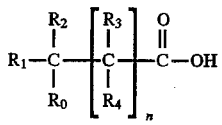

wherein $R_0$ is aryl, phenoxy, substituted aryl or substituted phenoxy;

$R_1$ and $R_2$ are, independently, H, hydroxy, lower alkoxy, lower straight or branched chain alkyl or halogen;

$R_3$ and $R_4$ are, independently, H, lower alkoxy, lower straight or branched chain alkyl or halogen; and n is an integer from 0 to 2;

a pharmaceutically-acceptable salt thereof or a mixture thereof.

2. The method of claim 1, wherein the compound is sodium phenylacetate.

3. The method of claim 1, wherein the compound is sodium phenylbutyrate.

4. The method of claim 1, wherein the compound is administered in combination with an anti-neoplastic agent.

5. The method of claim 1, wherein the prophylactic amount is from 50 to 500 mg/kg/day.

6. The method of claim 1, wherein the prophylactic amount is from 300 to 500 mg/kg/day.

7. The method of claim 1, wherein the prophylactic amount is from 150 to 250 mg/kg/day.

8. The method of claim 1, wherein the neoplastic condition is a neuroblastoma.

9. The method of claim 1, wherein the neoplastic condition is an acute promyelocytic leukemia.

10. The method of claim 1, wherein the neoplastic condition is an acute myelodysplasia.

11. The method of claim 1, wherein the neoplastic condition is an acute glioma.

12. The method of claim 1, wherein the neoplastic condition is prostate cancer.

13. The method of claim 1, wherein the neoplastic condition is breast cancer.

14. The method of claim 1, wherein the neoplastic condition is a melanoma.

15. The method of claim 1, wherein the neoplastic condition is non-small cell lung cancer.

16. The method of claim 14, wherein the anti-neoplastic agent is dimethyl sulfoxide, sodium butyrate, bromodeoxymidine, a retinoid, vitamin D, vitamin A, vitamin $B_{12}$, vitamin C, vitamin E, a terpene, IFN-$\alpha$, hydroxyurea, 5-azacytidine, 5-aza-2'-deoxycytidine, or suramin.

17. The method of claim 1, wherein $R_0$ is aryl or phenoxy, the aryl and phenoxy being unsubstituted or substituted with, independently, one or more halogen, hydroxy or lower alkyl.

18. The method of claim 1, wherein $R_0$ is phenyl, naphthyl, or phenoxy, the phenyl, naphthyl and phenoxy being unsubstituted or substituted with, independently, one or more moieties of halogen, hydroxy or lower alkyl.

19. The method of claim 1, wherein $R_0$ is phenyl, naphthyl, or phenoxy, the phenyl, naphthyl and phenoxy being unsubstituted or substituted with, independently, from 1 to 4 moieties of halogen, hydroxy or lower alkyl of from 1 to 4 carbon atoms;

$R_1$ and $R_2$ are, independently, H, hydroxy, lower alkoxy of from 1 to 2 carbon atoms, lower straight or branched chain alkyl of from 1 to 4 carbon atoms or halogen; and $R_3$ and $R_4$ are, independently, H, lower alkoxy of from 1 to 2 carbon atoms, lower straight or branched chain alkyl of from 1 to 4 carbon atoms or halogen.

20. The method of claim 1, wherein n is 0; $R_0$ is aryl or substituted aryl; $R_1$ and $R_2$ are H, lower alkoxy, or lower alkyl; pharmaceutically-acceptable salts thereof; or mixtures thereof.

21. The method of claim 18, wherein the compound is $\alpha$-methylphenylacetic acid, $\alpha$-ethylphenylacetic acid, $\alpha$-hydroxyphenylacetic acid, $\alpha$-methoxyphenylacetic acid, 1-naphthylacetic acid, 4-chlorophenylacetic acid, 4-iodophenylacetic acid, 4-fluorophenylacetic acid, 3-chlorophenylacetic acid, 2-chlorophenylacetic acid, 2,6-dichlorophenylacetic acid, 2-methylphenylacetic acid, 3-methylphenylacetic acid, 4-methylphenylacetic acid, phenoxypropionic acid, 4-chlorophenylbutyric acid, 4-iodophenylbutyric acid, 4-fluorophenylbutyric acid, 3-chlorophenylbutyric acid, or 2-chlorophenylbutyric acid.

22. The method of claim 1, wherein the compound is administered topically.

23. The method of claim 22, wherein the compound is applied at a concentration of from about 0.1 mM to about 10 mM.

24. The method of claim 1, wherein the compound is administered ocularly.

25. The method of claim 1, wherein the compound is administered orally.

26. The method of claim 1, wherein the compound is administered in the form of a suppository.

27. The method of claim 1, wherein the compound is administered parenterally.

28. The method of claim 1, wherein the compound is administered intermittently.

29. The method of claim 1, wherein the compound is administered continuously.

30. The method of claim 11, wherein the neoplastic condition is prostatic carcinoma, glioma, astrocytoma, adenocarcinoma, melanoma, lymphoma, leukemia, breast cancer, osteosarcoma, fibrosarcoma, squamous cancer, neuroblastoma, non-small cell lung cancer, mesothelioma, multiple myeloma, renal carcinoma, Kaposi's sarcoma, or Lennert's T-Cell lymphoma.

* * * * *